United States Patent [19]

Ghosh et al.

[11] Patent Number: 5,677,272

[45] Date of Patent: Oct. 14, 1997

[54] BLEACHING COMPOSITIONS COMPRISING PROTEASE ENZYMES

[75] Inventors: Chanchal Kumar Ghosh, West Chester; Michael Eugene Burns, Hamilton, both of Ohio; David Neil DiGiulio, Hunt Valley, Md.; Edward Eugene Getty, Cincinnati, Ohio; Richard Timothy Hartshorn, Newcastle Upon the Tyne, England; Alan David Willey, Cincinnati, Ohio; Philip F. Brode, Cincinnati, Ohio; Bobby L. Barnett, Cincinnati, Ohio; Donn N. Rubingh, Cincinnati, Ohio

[73] Assignee: The Procter & Gamble Company, Cincinnati, Ohio

[21] Appl. No.: 322,677

[22] Filed: Oct. 13, 1994

Related U.S. Application Data

[63] Continuation-in-part of Ser. No. 136,626, Oct. 14, 1993, abandoned, and Ser. No. 237,938, May 2, 1994, abandoned.

[51] Int. Cl.[6] .......................... C11D 3/386; C11D 3/395
[52] U.S. Cl. .......................... 510/306; 510/313; 510/320; 510/374; 510/375; 510/392; 510/490; 435/219; 435/220; 435/221; 435/222; 435/223; 435/224; 435/225; 134/42
[58] Field of Search ........................ 252/174.12, 95, 252/DIG. 12; 435/219–225, 263–264; 510/306, 313, 320, 375, 374, 392, 490; 134/42

[56] References Cited

U.S. PATENT DOCUMENTS

| Re. 34,606 | 5/1994 | Estell et al. | 435/222 |
|---|---|---|---|
| 4,634,551 | 1/1987 | Burns et al. | 252/102 |
| 4,686,063 | 8/1987 | Burns et al. | 252/102 |
| 4,760,025 | 7/1988 | Estell et al. | 435/222 |
| 4,844,821 | 7/1989 | Mermelstein et al. | 252/8.7 |

(List continued on next page.)

FOREIGN PATENT DOCUMENTS

| 0251446 | 1/1988 | European Pat. Off. | |
|---|---|---|---|
| 328229 | 6/1989 | European Pat. Off. | C12N 9/50 |
| 398539 | 11/1990 | European Pat. Off. | C12N 9/54 |
| 405902 | 1/1991 | European Pat. Off. | C11D 3/386 |
| 405901 | 1/1991 | European Pat. Off. | C11D 3/386 |
| 571049 | 11/1993 | European Pat. Off. | C12N 15/57 |

(List continued on next page.)

OTHER PUBLICATIONS

Wells et al., *PNAS*, vol. 84 pp. 5167–5771, Aug. 1987.
Wells et al, *TIBS*, H 13, Aug. 1988, pp. 291–297.
Egmons, Engineering Surface Changes in a Subtilisin, 1st International Symposium on Subtilisin Enzymes, Hamburg Sep. 1992.

(List continued on next page.)

*Primary Examiner*—Paul Lieberman
*Assistant Examiner*—Kery A. Fries
*Attorney, Agent, or Firm*—Kim William Zerby; Jerry J. Yetter; Jacobus C. Rasser

[57] ABSTRACT

The invention herein provides bleaching compositions comprising a protease enzyme which is a carbonyl hydrolase variant having an amino acid sequence not found in nature, which is derived by replacement of a plurality of amino acid residues of a precursor carbonyl hydrolase with different amino acids, wherein said plurality of amino acid residues replaced in the precursor enzyme correspond to position +76 in combination with one or more of the following residues: +99, +101, +103, +104, +107, +123, +27, +105, +109, +126, +128, +135, +156, +166, +195, +197, +204, +206, +210, +216, +217, +218, +222, +260, +265, and/or +274, where the numbered positions corresponds to naturally-occurring subtilisin from *Bacillus amyloliquefaciens* or to equivalent amino acid residues in other carbonyl hydrolases or subtilisins (such as *Bacillus lentus* subtilisin) and a bleaching agent.

10 Claims, 18 Drawing Sheets

U.S. PATENT DOCUMENTS

| | | | |
|---|---|---|---|
| 4,914,031 | 4/1990 | Zukowski et al. | 435/222 |
| 4,966,723 | 10/1990 | Hodge et al. | 252/102 |
| 5,069,809 | 12/1991 | Lagerwaard et al. | 252/174.12 |
| 5,118,623 | 6/1992 | Boguslawski et al. | 435/222 |
| 5,155,033 | 10/1992 | Estell et al. | 435/221 |
| 5,182,204 | 1/1993 | Estell et al. | 435/222 |
| 5,185,258 | 2/1993 | Caldwell et al. | 435/220 |
| 5,204,015 | 4/1993 | Caldwell et al. | 252/174.12 |
| 5,260,207 | 11/1993 | Pantoliano et al. | 435/221 |
| 5,324,653 | 6/1994 | van Eekelen et al. | 435/221 |
| 5,336,611 | 8/1994 | van Eekelen et al. | 435/221 |
| 5,340,735 | 8/1994 | Christianson et al. | 435/221 |

FOREIGN PATENT DOCUMENTS

| | | | |
|---|---|---|---|
| WO 88/08028 | 10/1988 | WIPO | C12N 15/00 |
| 8904361 | 5/1989 | WIPO . | |
| WO 89/06279 | 7/1989 | WIPO | C12N 9/50 |
| WO 89/09819 | 10/1989 | WIPO | C12N 9/54 |
| WO 91/00345 | 1/1991 | WIPO | C12N 9/50 |
| WO 91/06637 | 5/1991 | WIPO | C12N 9/48 |
| WO 92/08778 | 5/1992 | WIPO | C11D 3/386 |
| WO 92/11357 | 7/1992 | WIPO | C12N 9/56 |
| WO 92/21760 | 12/1992 | WIPO | C12N 15/57 |
| WO 94/02618 | 2/1994 | WIPO | C12N 15/57 |
| WO 94/10284 | 5/1994 | WIPO | C11D 3/386 |
| WO 94/23053 | 10/1994 | WIPO | C12P 9/56 |
| 9510591 | 4/1995 | WIPO . | |
| 9510615 | 4/1995 | WIPO . | |
| 9510592 | 9/1995 | WIPO . | |

OTHER PUBLICATIONS

Arnold, F. *TIBTECH* vol. 8, pp. 244–248, Sep. 1990.

Biological Abstracts (9):AB–385 No. 95173, Owers et al., "Enhanced stability of sutilisin by three point mutations"(Jan. 15, 1991).

Bott, R. et al., "Using Structural Comparison as a Guide in Protein Engineering", Annals of the New York Academy of Sciences, vol. 672, pp. 10–19 (Nov. 30, 1992).

Graycar, Thomas P. et al., "Altering the Proteolytic Activity of Subtilisin through Protein Engineering", Annals of the New York Academy of Sciences, vol. 672, pp. 71–79 (1992).

Siezen, Roland J. et al., "Homology Modelling and Protein Engineering Strategy of Subtilases, the Family of Subtilisin–Like Serine Proteinases", Protein Engineering, vol. 4, No. 7, pp. 719–737 (1991).

Stauffer, C. E. et al., "The Effect on Subtilisin Activity of Oxidizing a Methionine Residue", The Journal of Biological Chemistry, No. 19, vol. 244, pp. 5333–5338 (Oct. 10, 1965).

Pantoliano, Michael W. et al., "Large Increases in General Stability of Subtilisin BPN' through Incremental Changes in the Free Energy of Unfolding", Biochemistry 28:7205–7213 (Jun. 21, 1989).

Polgar, Laszio et al., "Analytical Evidence for the Chemical Transformation of the Essential Serine–221 to Cysteine–221", Biochimica et Biophysica Acta, 667:351–354 (1981).

Svendsen, I.B., "Chemical Modifications of the Subtilisins with Special Reference to the Binding of Large Substrates", Carlsberg Res. Commun., vol. 41, No. 5 pp. 237–291 (1976).

Wells, James A., "Designing Substrate Specificity by Protein Engineering of Electrostatic Interactions", Proc. Natl. Acad. Sci. USA, vol. 84, pp. 1219–1223 (Mar. 1987).

U.S. application No. 08/237,939, Brode et al., filed May 5, 994.

U.S. application No. 08/322,676, Baeck et al., filed Oct. 1994.

U.S. application No. 08/394,011, Brode et al., filed Mar. 1995.

U.S. application No. 08/397,329, Brode et al., filed Mar. 1995.

U.S. application No. 08/400,068, Brode et al., filed Mar. 1995.

U.S. application No. 08/479,786, Digiulio et al., filed Oct. 1993.

```
                          -1 | 1                                          10
         His Bal Ala His Ala Tyr Ala Gln Ser Val Pro Tyr Gly Val Ser Gln Ile Lys Ala Pro Ala LEu His Ser Gln
     399 CAC GTA GCA CAT GCA TAC GCG CAG TCC GTG CCT TAC GGC GTA TCA CAA ATT AAA GCC CCT GCT CTG CAC TCT CAA 20                                    30                                    40
         Gly Tyr Thr Gly Ser Asn Val Lys Val Ala Val Ile Asp Ser Gly Ile Asp Ser Ser His Pro Asn Leu Lys Val
     474 GGC TAC ACT GGA TCA AAT GTT AAA GTA GCG GTT ATC GAC AGC GGT ATC GAT TCT TCT CAT CCT GAT TTA AAG GTA

Pro Asn             60 Asp
         Ala Gly Gly Ala Ser Met Val Pro Ser Glu Thr Asn Pro Phe Gln Asp Asn Asn Ser His Gly Thr His Val Ala
     549 GCA GGC GGA GCC AGC ATG GTT CCT TCT GAA ACA AAT CCT TTC CAA GAC AAC AAC TCT CAC GGA ACT CAC GTT GCC

Ser Ala 90
         Gly Thr Val Ala Ala Leu Asn Asn Ser Ile Gly Val Leu Gly Val Ala Pro Ser Ala Ser Leu Tyr Ala Val Lys
     624 GGC ACA GTT GCG GCT CTT AAT AAT TCA ATC GGT GTA TTA GGC GTT GCG CCA AGC GCA TCA CTT TAC GCT GTA AAA

Asp Ala 100                                    110
         Val Leu Gly Ala Asp Gly Ser Gly Gln Tyr Ser Trp Ile Ile Asn Gly Ile Glu Trp Ala Ile Ala Asn Asn Met
     699 GTT CTC GGT GCT GAC GGT TCC GGC CAA TAC AGC TGG ATC ATT AAC GGA ATC GAG TGG GCG ATC GCA AAC AAT ATG 120                                   130                                   140
         Asp Val Ile Asn Met Ser Leu Gly Gly Pro Ser Gly Ser Ala Ala Leu Lys Ala Ala Val Asp Lys Ala Val Ala
     774 GAC GTT ATT AAC ATG AGC CTC GGG GGA CCT TCT GGT TCT GCT GCT TTA AAA GCG GCA GTT GAT AAA GCC GTT GCA

Ser Thr 160
         Ser Gly Val Val Val Val Ala Ala Ala Gly Asn Glu Gly Ser Ser Gly Ser Ser Ser Thr Val Gly Tyr Pro Gly
     849 TCC GGC GTA GTC GTT GCG GCA GCC GGT AAC GAA GGC TCC AGC GGC AGC TCA AGC ACA GTG GGC TAC CCT GGT
```

FIG-1B

```
       170                                              180                                        190
     Lys Tyr Pro Ser Val Ile Ala Val Gly Ala Val Asp Ser Ser Asn Gln Arg Ala Ser Phe Ser Ser Val Gly Pro
 924 AAA TAC CCT TCT GTC ATT GCA GTT GGC GCT GTT GAC AGC AGC AAC CAA AGA GCA TCT TTC TCA AGC GTA GGA CCT 200                                        210
     Glu Leu Asp Val Met Ala Pro Gly Val Ser Ile Gln Ser Thr Leu Pro Gly Asn Lys Tyr Gly Ala Tyr Asn Gly
 999 GAG CTT GAT GTC ATG GCA CCT GGC GTA TCT ATC CAA AGC ACG CTT CCT GGA AAC AAA TAC GGG GCG TAC AAC GGT 220                                              230                                        240
     Thr Ser Met Ala Ser Pro His Val Ala Gly Ala Ala Leu Ile Leu Ser Lys His Pro Asn Trp Thr Asn Thr
1074 ACG TCA ATG GCA TCT CCG CAC GTT GCC GGA GCG GCT TTG ATT CTT TCT AAG CAC CCG AAC TGG ACA AAC ACT

250 Gln                                         260
     Gln Val Arg Ser Ser Ser Leu Glu Asn Thr Thr Lys Leu Gly Asp Ser Phe Tyr Tyr Gly Lys Gly Leu Ile Asn
1149 CAA GTC CGC AGC AGT AGT TTA GAA AAC ACC ACT AAA CTT GGT GAT TCT TTG TAC TAT GGA AAA GGG CTG ATC AAC 270            275
     Val Gln Ala Ala Ala Gln OC            TERM
1224 GTA CAA GCG GCA GCG CAG TAA  AACATAAAAACCGGCCTTGGCCCCGCCGGGTTTTTATTATTTTTCCTCCTCCGGATGTTCAATCCGCTCC

1316 ATAATCGACGGATGGCTCCCTCTGAAAATTTTAACGAGAAACGGGGTTGACCCGGCTCAGTCCCGTAACGGCCAACTCCTGAAACGTCTCAATCGCCG

1416 CTTCCCGGTTTCCGGTCAGCTCAATGCCATAACGGTCGGGGGGGCGGTTTTCCTGATACCGGGAGACGGGCATTCGTAATCGGATC
```

FIG.-1C

CONSERVED RESIDUES IN SUBTILISINS FROM *BACILLUS AMYLOLIQUEFACIENS*

Comparison of subtilisin sequences from:

B.amyloliquefaciens
B.subtilis
B.licheniformis
B.lentus

```
161 SSTVGYPGKYPSVIAVGAVDSSNQRASFSSVGPELDVMAA
    SSTVGYPAKYPSTIAVGAVDSSNSRASFSSAGSEELVMAA
    STNTIGYPAKYDSVIAVGATDNNRASFSSVGAEVMAA
    ****ISYPARYANAMAVGATDQNNRASFSQYGAGLDIVA

201 PGVSIQSTLPGNKYGAYNGTSMASPHVAGAAALILSKKHPN
    PGVSIQSTLPGGTYGAYNGTSMATPHVAGAAALILSKKHPT
    PGAGVVSTYPTNTYATLNGTSMASPHVAGAAALILSKKHPN
    PGVNVQSTYPGSTYASLNGTSMATPHVAGAAALVKQKNPS

241 WTNTQVRSSLENTTTKLGDSFYYGKGLINVQAAAAQ
    WTNAQVRDRLESTATYLGNSFYYGKGLINVQAAAAQ
    LSASQVRNRLSSTATYLGSSFYYGKGLINVEAAAAQ
    WSNVQIRNHLKNTATSLGSTNLYGSGLVNAEAATR
```

FIG 3/B

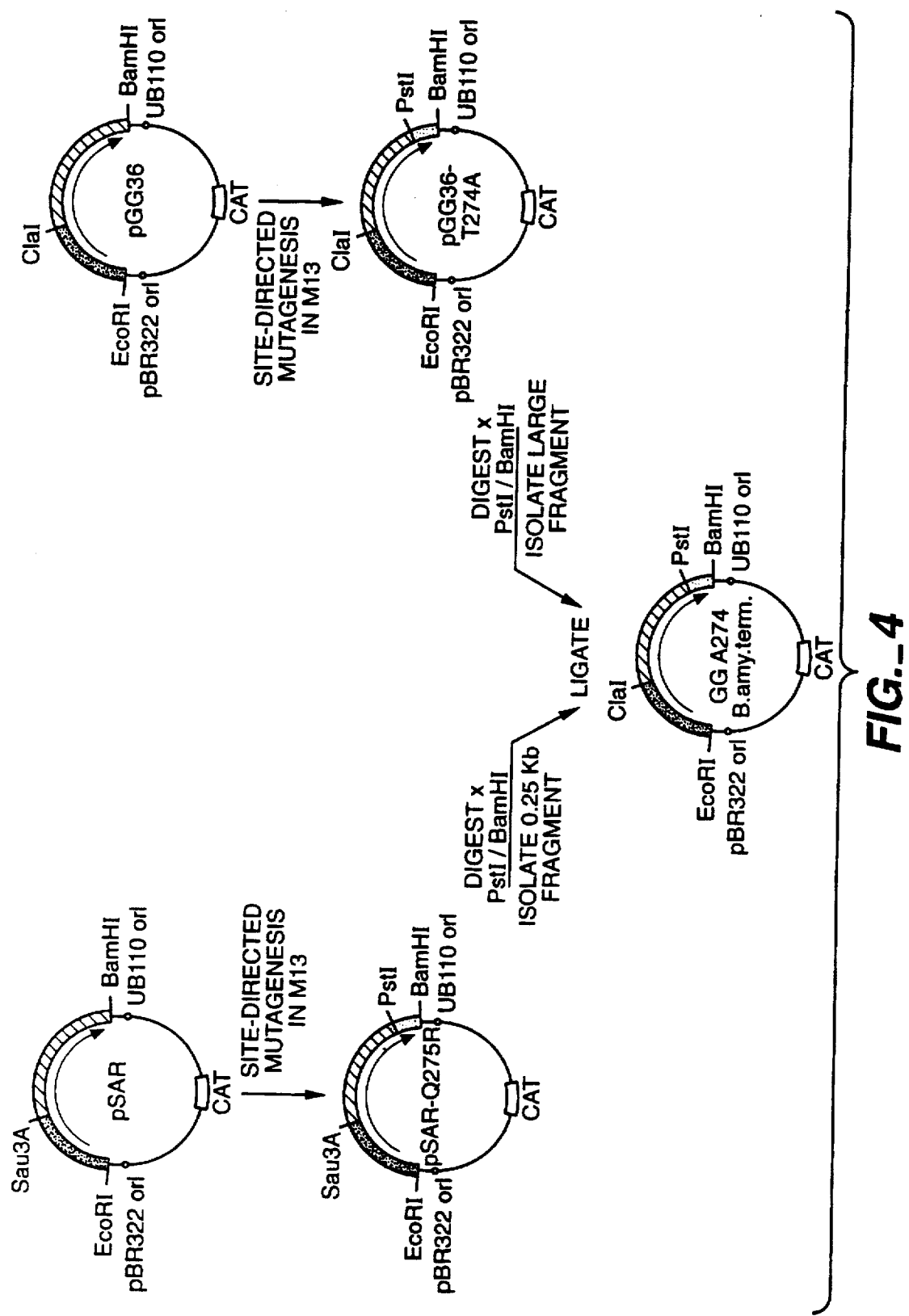
FIG._4

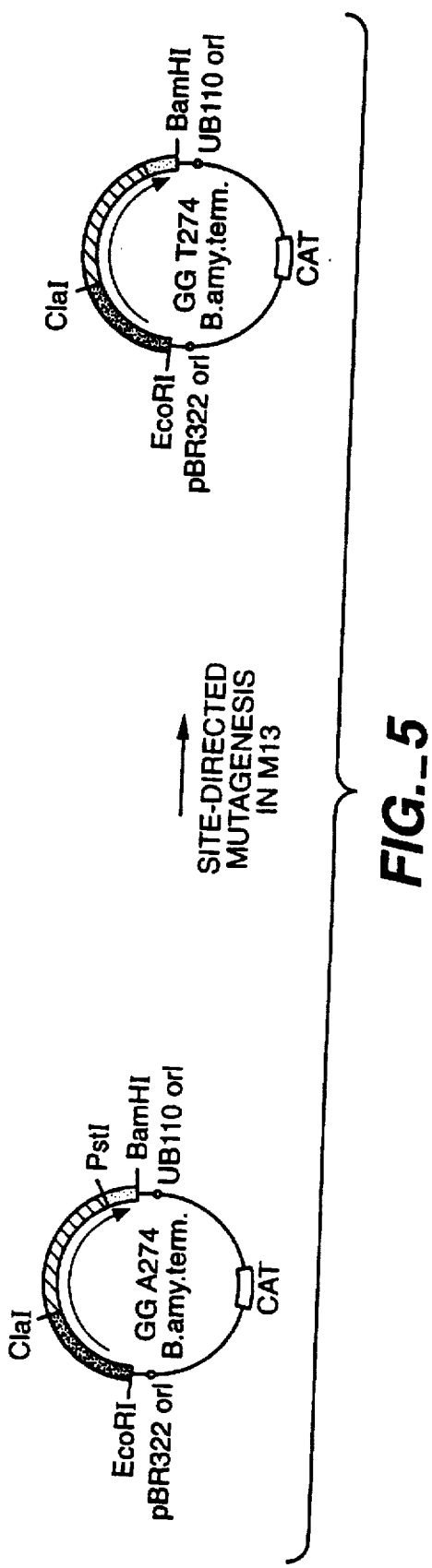
FIG._5

```
10                              30                               50
ATGAAGAAACCGTTGGGGAAAATTGTCGCAAGCACCGCACTACTCATTTCTGTTGCTTTT
MetLysLysProLeuGlyLysIleValAlaSerThrAlaLeuLeuIleSerValAlaPhe 70                              90                              110
AGTTCATCGATCGCATCGGCTGCTGAAGAAGCAAAAGAAAAATATTTAATTGGCTTTAAT
SerSerSerIleAlaSerAlaAlaGluGluAlaLysGluAlaLysTyrLeuIleGlyPheAsn 130                             150                             170
GAGCAGGAAGCTGTCAGTGAGTTTGTAGAACAAGTAGAGGCAAATGACGAGGTCGCCATT
GluGlnGluAlaValSerGluPheValGluGlnValGluAlaAsnAspGluValAlaIle 190                             210                             230
CTCTCTGAGGAAGAGGAAGTCGAAATTGCTTCATGAATTTGAAACGATTCCTGTT
LeuSerGluGluGluGluValGluIleLeuLeuLeuHisGluPheGluThrIleProVal 250                             270                             290
TTATCCGTTGAGTTAAGCCCAGAAGATGTGGACGCGCTTGAACTCGATCCAGCGATTTCT
LeuSerValGluLeuSerProGluAspValAspAlaLeuGluLeuAspProAlaIleSer 310                             330                             350
TATATTGAAGAGGATGCAGAAGTAACGACAATGGCCGCAATCAGTGTCCCATGGGAATTAGC
TyrIleGluGluAspAlaGluValThrThrMetAlaGlnSerValProTrpGlyIleSer 370                             390                             410
CGTGTGCAAGCCCCCAGCTGCCCATAACCGTGGATTGACACAGGTTCTGTGTAAAAGTTGCT
ArgValGlnAlaProAlaAlaHisAsnArgGlyLeuThrGlyLeuSerGlyValLysValAla
```

FIG._6A

```
                    430                              450                                470
GTCCTCGATACAGGTATTTCCACTCATCCAGACTTAAATATTCGTGGTGGCGCTAGCTTT
ValLeuAspThrGlyIleSerThrHisProAspLeuAsnIleArgGlyGlyAlaSerPhe 490                              510                                530
GTACCAGGGGAACCATCCACTCAAGATGGAATGGGACATGGCACGCCGGGACG
ValProGlyGluProSerThrGlnAspGlyAsnGlyHisGlyThrHisValAlaGlyThr 550                              570                                590
ATTGCTGCTTTAAACAATTCGATTGGCGTTCTTGGCGTAGCGCCGAGCGCCGGAACTATAC
IleAlaAlaLeuAsnAsnSerIleGlyValLeuGlyValAlaProSerAlaGluLeuTyr 610                              630                                650
GCTGTTAAAGTATTAGGGGCGAGCGGTTCGGTTCAGCTCGATTGCCCAAGGATTG
AlaValLysValLeuGlyAlaSerGlySerValSerSerIleAlaGlnGlyLeu 670                              690                                710
GAATGGGCAGGGAACAATGGCATGCACGTTGCTAATTTGAGTTTAGGAAGCCCTTCGCCA
GluTrpAlaGlyAsnAsnGlyMetHisValAlaAsnLeuSerLeuGlySerProSerPro 730                              750                                770
AGTGCCACACTTGAGCAAGCTGTTAATAGCGCGACTTCTAGAGGCGTTCTTGTTGTAGCG
SerAlaThrLeuGluGlnAlaValAsnSerAlaThrSerArgGlyValLeuValValAla 790                              810                                830
GCATCTGGAATTCAGGTGCAGGCTCAATCAGCTATCCGGCCCGTTATGCGAACGCAATG
AlaSerGlyAsnSerGlyAlaGlySerIleSerTyrProAlaArgTyrAlaAsnAlaMet
```

FIG._6B

850
GCAGTCGGGAGCTACTGACCAAAACAACCGGCCAGCTTTCACAGTATGGCGCAGGG
AlaValGlyAlaThrAspGlnAsnAsnArgAlaSerPheSerGlnTyrGlyAlaGly

910
CTTGACATTGTCGCACCAGGTGTAAACGTGCAGAGCACATACCCAGTTCAACGTATGCC
LeuAspIleValAlaProGlyValAsnValGlnSerThrTyrProGlySerThrTyrAla

970
AGCTTAAACGGTACATCGATGGCTACTCCTCATGTTGCAGGTGCAGCCCTTGTTAAA
SerLeuAsnGlyThrSerMetAlaThrProHisValAlaGlyAlaAlaLeuValLys

1030
CAAAAGAACCCATCTTGGTCCAATGTACAAATCCGCAATCATCTAAAGAATACGGCAACG
GlnLysAsnProSerTrpSerAsnValGlnIleArgAsnHisLeuLysAsnThrAlaThr

1090
AGCTTAGGAAGCACGAACTTGTATGGAAGCGGACTTGTCAATGCAGAAGCGGCAACACGC
SerLeuGlySerThrAsnLeuTyrGlySerGlyLeuValAsnAlaGluAlaAlaThrArg

870
GCCAGTCGGGAGCTACTGACCAAAACAACCGGCCAGCTTTCACAGTATGGCGCAGGG

| *FIG._6A* |
| *FIG._6B* |
| *FIG._6C* |

*FIG._6*

```
                    10                         30                                50
ATGAAGAAACCGTTGGGAAAATTGTCGCAAGCACCGCACTACTCATTCTGTTGCTTT
MetLysLysProLeuGlyLysIleValAlaSerThrAlaLeuLeuIleSerValAlaPhe 70                         90                               110
AGTTCATCGATCGCATCGGCTGCTGAAGAAGCAAAAGAAAAATATTTAATTGGCTTTAAT
SerSerIleAspArgIleAlaAlaGluGluAlaLysGluLysTyrLeuIleGlyPheAsn 130                        150                               170
GAGCAGGAAGCTGTCAGTGAGTTTGTAGAACAAGTAGAGGCAAATGACGAGGTCGCCATT
GluGlnGluAlaValSerGluPheValGluGlnValGluAlaAsnAspGluValAlaIle 190                        210                               230
CTCTCTGAGGAAGAGGAAGTCGAAATTGAATTGCTTCATGAATTGAAACGATTCCTGTT
LeuSerGluGluGluGluValGluIleGluLeuLeuHisGluPheGluThrIleProVal 250                        270                               290
TTATCCGTTGAGTTAAGCCCAGAAGATGTGGACGCGCTTGAACTCGATCCAGCGATTTCT
LeuSerValGluLeuSerProGluAspValAspAlaLeuGluLeuAspProAlaIleSer 310                        330                               350
TATATTGAAGAGGATGCAGAAGTAACGACAATGGCGCAATCAGTGCCATGGGAATTAGC
TyrIleGluGluAspAlaGluValThrThrMetAlaGlnSerValProTrpGlyIleSer 370                        390                               410
CGTGTGCAAGCCCCAGCTGCCCATAACCGTGGATTGACAGGTTCTGTGTAAAGTTGCT
ArgValGlnAlaProAlaAlaHisAsnArgGlyLeuThrGlySerGlyValLysValAla
```

FIG._7A

```
                                          470
         430
GTCCTCGATACAGGTATTCCACTCCATCCAGACTTAAATATTCGTGGTGGCGCTAGCTTT
ValLeuAspThrGlyIleSerThrHisProAspLeuAsnIleArgGlyGlyAlaSerPhe 490                              530
GTACCAGGGGAACCATCCACTCAAGATGGGAATGGCACGCATGTGGCCGGGACG
ValProGlyGluProSerThrGlnAspGlyAsnGlyThrHisValAlaGlyThr 550                              590
ATTGCTGCTTTAGACAACTCGATTGGCGTTCTTGGCGTAGCCCGAGCCGGGAACTATAC
IleAlaAlaLeuAspAsnSerIleGlyValLeuGlyValAlaProSerAlaGluLeuTyr 610                              650
GCTGTTAAAGTATTAGGGGCGAGCGGTTCAGGCGCCATCAGCTCGATTGCCCAAGGATTG
AlaValLysValLeuGlyAlaSerGlySerGlyAlaIleSerSerIleAlaGlnGlyLeu 670                              710
GAATGGGCAGGGAACAATGGCATGCACGTTGCTAATTTGAGTTTAGGAAGCCCTTCGCCA
GluTrpAlaGlyAsnAsnGlyMetHisValAlaAsnLeuSerLeuGlySerProSerPro 730                              770
AGTGCCACACTTGAGCAAGCTGTTAATAGCGGACTTCTAGAGGCGGTTCTTGTTGTAGCG
SerAlaThrLeuGluGlnAlaValAsnSerAlaThrSerArgGlyValLeuValValAla 790                              830
GCATCTGGGAATTCAGGTGCAGGCTCAATCAGCTATCCGGCCCGTTATGCGAACGCAATG
AlaSerGlyAsnSerGlyAlaGlySerIleSerTyrProAlaArgTyrAlaAsnAlaMet
```

*FIG._7B*

```
                    850                              870                              890
GCAGTCGGAGCTACTGACCAAAACAACAACCGGCGCCAGCTTTCACAGTATGGCGCAGGG
AlaValGlyAlaThrAspGlnAsnAsnArgAlaSerPheSerGlnTyrGlyAlaGly
                    910                              930                              950
CTTGACATTGTCGCACCAGGTGTAAACGTGCAGAGCACATACCCAGTTCAACGTATGCC
LeuAspIleValAlaProGlyValAsnValGlnSerThrTyrProGlySerThrTyrAla
                    970                              990                              1010
AGCTTAAACGGTACATCGATGGCTACTCCTCATGTTGCAGGTGCAGCCCTTGTTAAA
SerLeuAsnGlyThrSerMetAlaThrProHisValAlaGlyAlaAlaLeuValLys
                    1030                             1050                             1070
CAAAAGAACCCATCTTGGTCCAATGTACAAATCCGAATCATCTAAAGAATACGGCAACG
GlnLysAsnProSerTrpSerAsnValGlnIleArgAsnHisLeuLysAsnThrAlaThr
                    1090                             1110                             1130
AGCTTAGGAAGCACGAACTTGTATGGAAGCGGACTTGTCAATGCAGAAGCGGCAACACGC
SerLeuGlySerThrAsnLeuTyrGlySerGlyLeuValAsnAlaGluAlaAlaThrArg
```

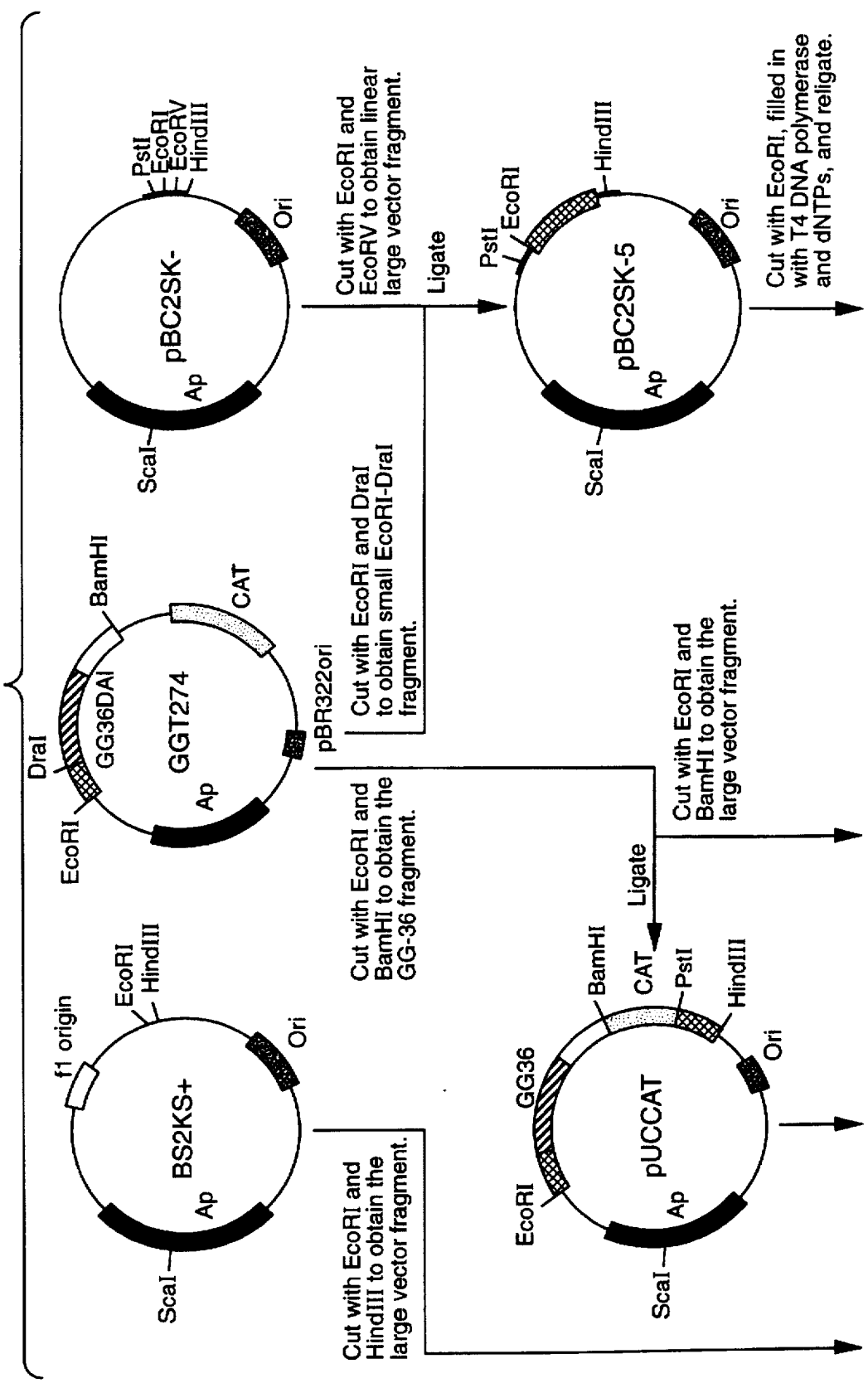
FIG._8A

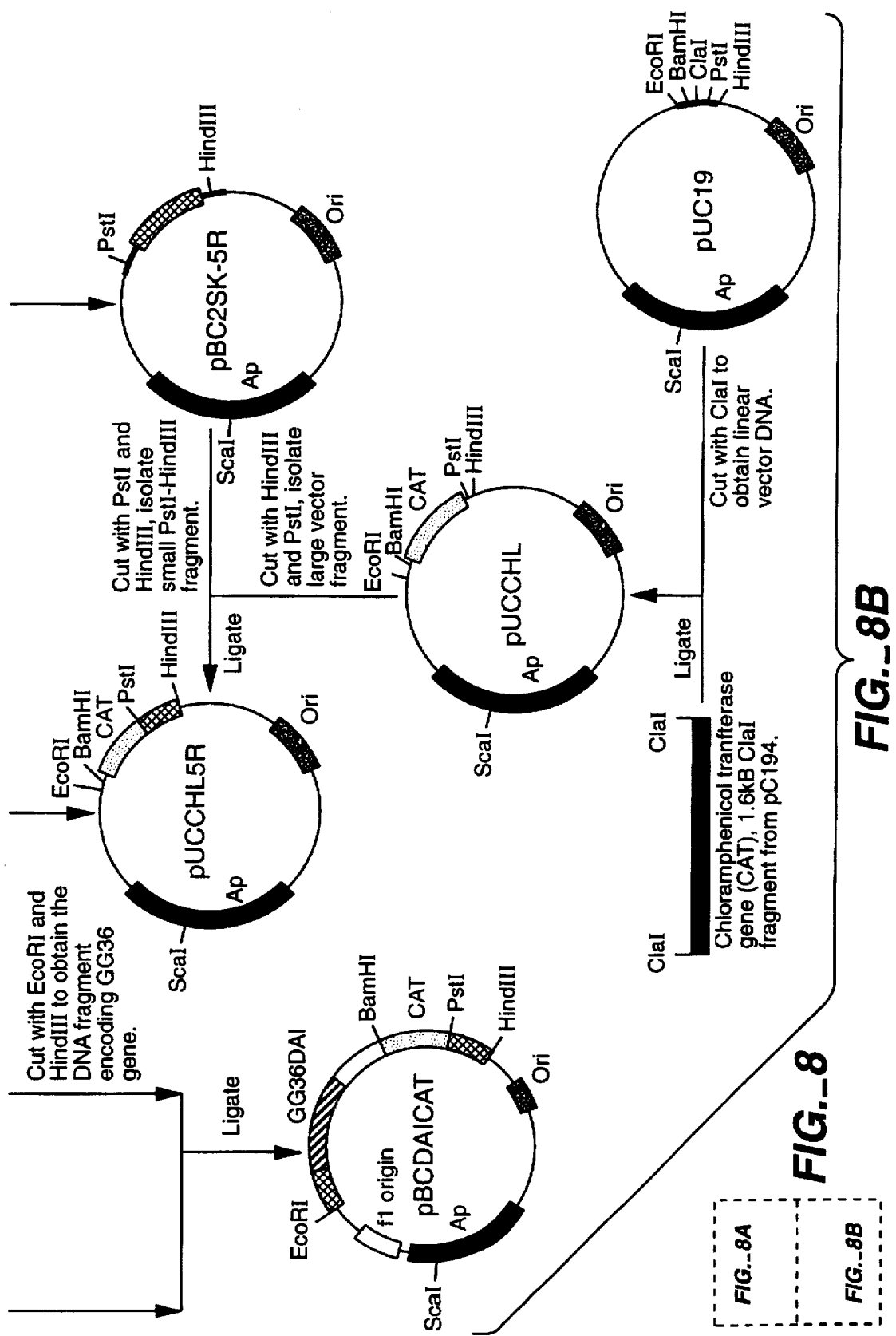
FIG._8B
FIG._8

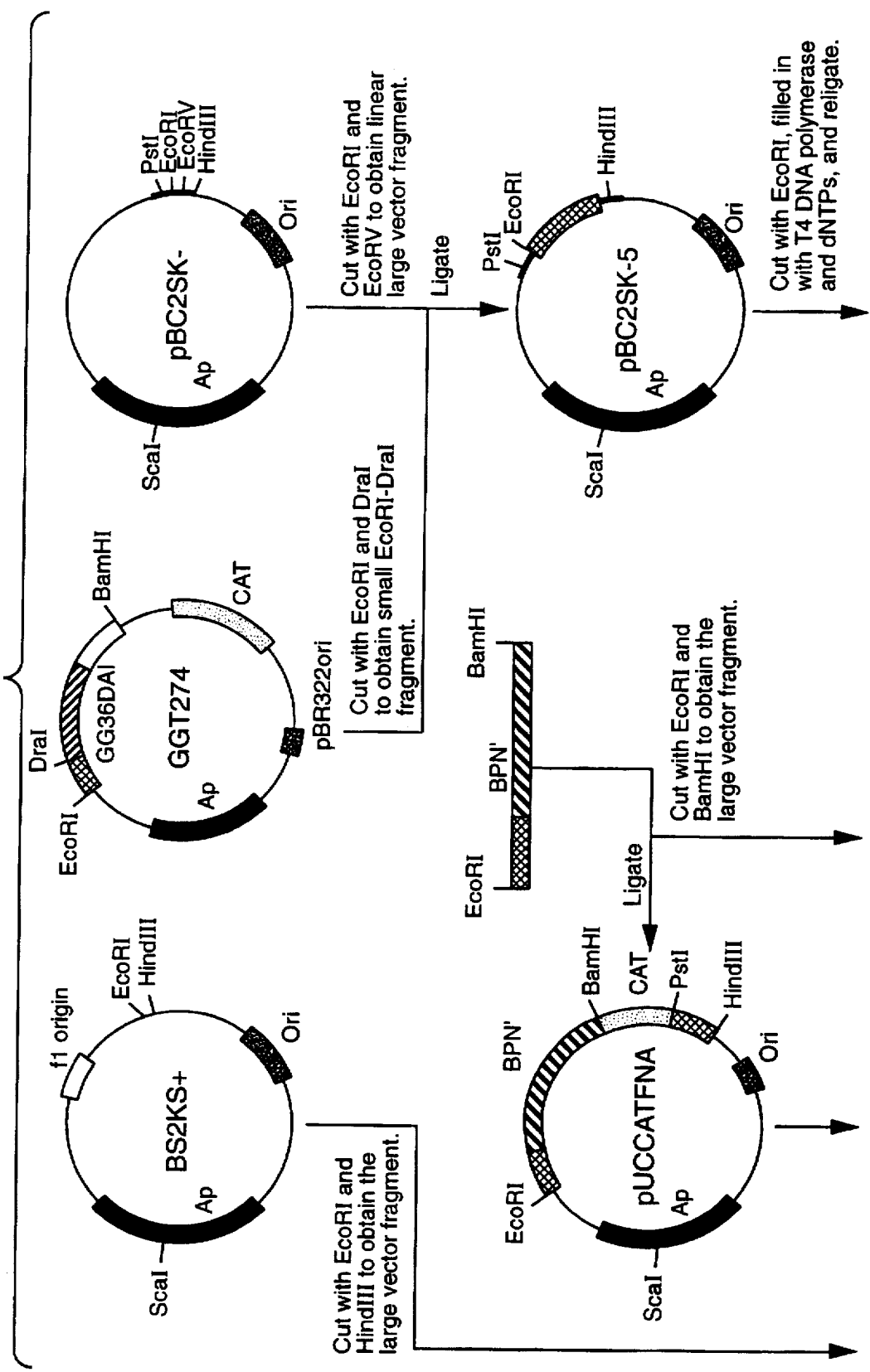
FIG._9A

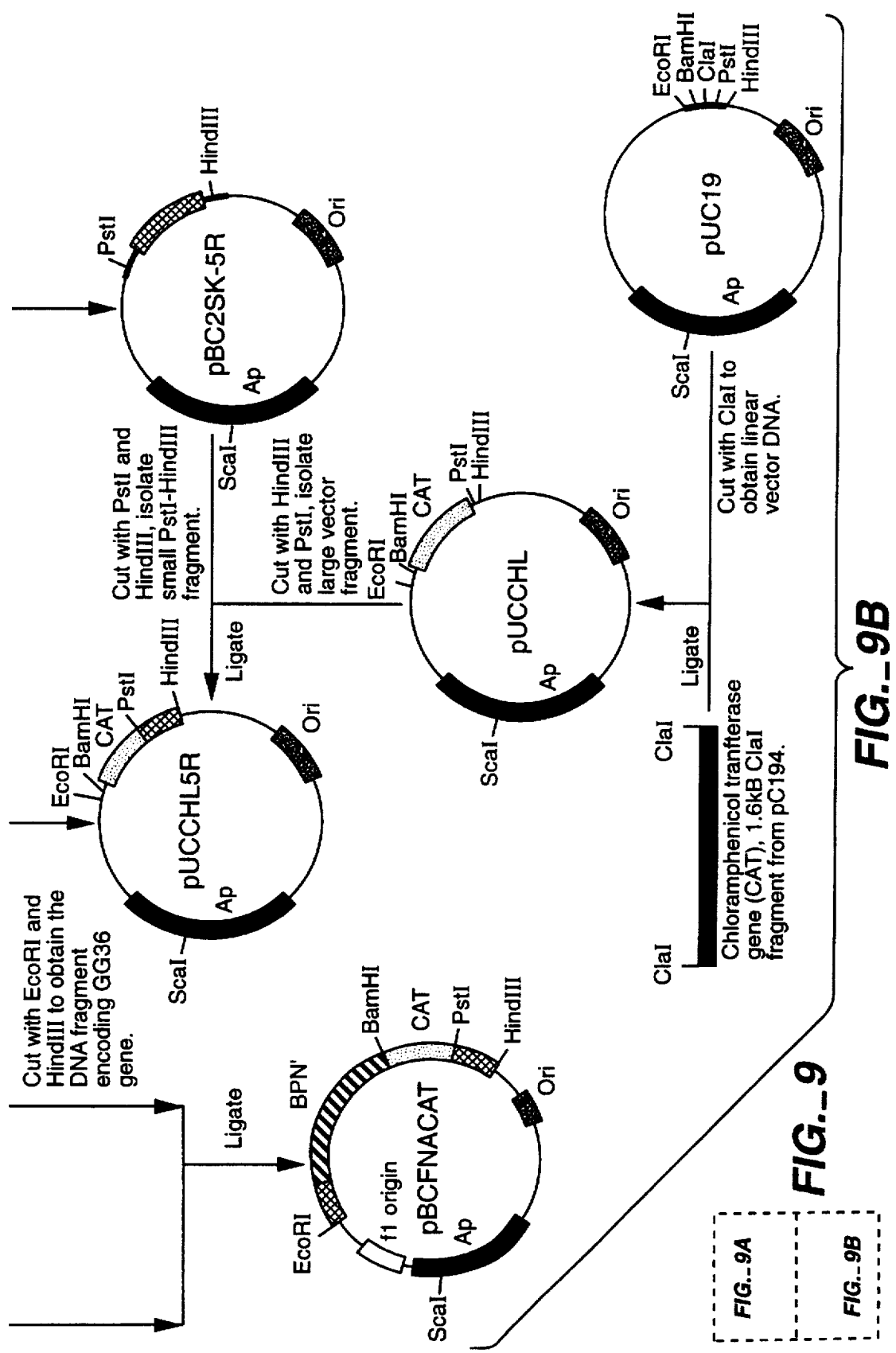

BLEACHING COMPOSITIONS COMPRISING PROTEASE ENZYMES

This application is a continuation-in-part application of U.S. application Ser. No. 08/136,626 filed Oct. 14, 1993, now abandoned and U.S. application Ser. No. 08/237,938, filed May 2, 1994, now abandoned both incorporated herein by reference in their entirety.

FIELD OF THE INVENTION

The present invention relates to bleaching compositions, especially laundry detergents, and methods which employ one or more protease enzymes which are carbonyl hydrolase variants and a bleaching system with one or more bleaching agents, especially bleach activators.

BACKGROUND OF THE INVENTION

Various types of enzymes have long been conventionally used in laundry detergents to assist in the removal of certain stains from fabrics. These stains are typically associated with lipid and protein soils. The enzymes, however, have proven less effective against other types of soils and stains.

It has also long been known that peroxygen bleaches are effective for stain and/or soil removal from fabrics, but that such bleaches are temperature dependent. At a laundry liquor temperature of 60° C., peroxygen bleaches are only partially effective. As the laundry liquor temperature is lowered below 60° C., peroxygen bleaches become relatively ineffective. As a consequence, there has been a substantial amount of industrial research to develop effective bleaching systems.

By the present invention, it has been discovered that the combination of novel protease enzymes which are carbonyl hydrolase variants and bleaching agents, especially bleach activators, provide effective stain removal and/or dingy cleanup benefits. It is therefore an object of the present invention to provide bleaching compositions, especially laundry detergent compositions, having improved stain removal and/or dingy cleanup benefits and/or fabric cleaning benefits and/or bleaching properties.

These and other objects of the present invention will be apparent from the detailed description hereinafter.

BACKGROUND ART

U.S. Pat. No. 4,634,551, Burns et al, issued Jan. 6, 1987, discloses amido peroxyacid bleaching compounds and their precursors which are employed in the present invention. See also, U.S. Pat. No. 4,852,989, Burns et al, issued Aug. 1, 1989. U.S. Pat. No. 5,069,809, Lagerwaard et al, issued Dec. 3, 1991 discloses the combination of NOBS bleach activators with LIPOLASE, lipase enzymes. See E.P. Patent 341,947, Lagerwaard, et al, published Nov. 15, 1989 for a discussion of the compatibility problems of lipase enzymes with certain bleaching systems. U.S. Pat. No. 4,545,784, Sanderson, issued Oct. 8, 1985, discloses the absorption of activators onto sodium perborate monohydrate.

SUMMARY OF THE INVENTION

The invention herein provides bleaching compositions comprising:

(a) an effective amount of protease enzyme which is a carbonyl hydrolase variant having an amino acid sequence not found in nature, which is derived by replacement of a plurality of amino acid residues of a precursor carbonyl hydrolase with different amino acids, wherein said plurality of amino acid residues replaced in the precursor enzyme correspond to position +76 in combination with one or more of the following residues: +99, +101, +103, +104, +107, +123, +27, +105, +109, +126, +128, +135, +156, +166, +195, +197, +204, +206, +210, +216, +217, +218, +222, +260, +265, and/or +274, where the numbered positions corresponds to naturally-occurring subtilisin from *Bacillus amyloliquefaciens* or to equivalent amino acid residues in other carbonyl hydrolases or subtilisins (such as *Bacillus lentus* subtilisin); and (b) a bleaching agent which either is an organic peroxyacid or is a combination of a bleach activator and a peroxygen compound capable of yielding hydrogen peroxide that can react with the activator to form an organic peroxyacid in situ in a bleaching solution formed from the composition; and (c) one or more cleaning composition materials compatible with the protease enzyme and bleaching agent.

The invention also encompasses a method for cleaning fabrics comprising contacting, preferably with agitation, said fabrics with an aqueous liquor containing said bleaching compositions. The method can be carried out at temperatures below about 60° C. but, of course, is quite effective at laundry temperatures up to the boil. The aqueous laundry liquor preferably comprises at least about 300 ppm of conventional detergent ingredients, as well as at least about 25 ppm of bleach activator and at least about 25 ppm of bleaching compound. Preferably, said aqueous liquor comprises from about 900 ppm to about 20,000 ppm of the conventional detergent ingredients, from about 100 ppm to about 25,000 ppm of bleaching compound and from about 100 ppm to about 2,500 ppm of said bleach activator.

The conventional detergent ingredients employed in said method comprise from about 1% to about 99.8%, preferably from about 5% to about 80%, of a detersive surfactant. Optionally, detersive compositions can also comprise from about 5% to about 80% of a detergent builder. Other optional detersive ingredients are also encompassed by the fully-formulated detergent/bleach compositions provided by this invention.

All percentages, ratios and proportions are by weight, unless otherwise specified. All documents cited are incorporated herein by reference.

BRIEF DESCRIPTION OF THE DRAWINGS

FIGS. 1A-C, depict the DNA and amino acid sequence for *Bacillus amyloliquefaciens* subtilisin and a partial restriction map of this gene (Seq. ID No.6).

FIG. 2 depicts the conserved amino acid residues among subtilisins from *Bacillus amyloliquefaciens* (BPN)' and *Bacillus lentus* (wild-type).

FIGS. 3A and 3B depict the amino acid sequence of four subtilisins. The top line represents the amino acid sequence of subtilisin from *Bacillus amyloliquefaciens* subtilisin (also sometimes referred to as subtilisin BPN') (Seq. ID No.7). The second line depicts the amino acid sequence of subtilisin from *Bacillus subtilis* (Seq. ID No.8). The third line depicts the amino acid sequence of subtilisin from *B. licheniformis* (Seq. ID No.9). The fourth line depicts the amino acid sequence of subtilisin from *Bacillus lentus* (also referred to as subtilisin 309 in PCT WO89/06276) (Seq. ID No.10). The symbol * denotes the absence of specific amino acid residues as compared to subtilisin BPN'.

FIG. 4 depicts the construction of plasmid GGA274.

FIG. 5 depicts the construction of GGT274 which is an intermediate to certain expression plasmids used in this application.

FIGS. 6A and 6B depict the DNA and amino acid sequence of subtilisin from *Bacillus lentus* (Seq. ID No. 11). The mature subtilisin protein is coded by the codons beginning at the codon GCG (334-336) corresponding to Ala.

FIGS. 7A and 7B depict the DNA and amino acid sequence of a preferred embodiment of the invention (N76D/S103A/V104I) (Seq. ID No. 12). The DNA in this figure has been modified by the methods described to encode aspartate at position 76, alanine at position 103 and isoleucine at position 104. The mature subtilisin variant protein is coded by the codons beginning at the codon GCG (334-336) corresponding to Ala.

FIG. 8 depicts the construction of vector pBCDAICAT.

FIG. 9 depicts the construction of vector pUCCATFNA.

DETAILED DESCRIPTION OF THE INVENTION

Figure 1A:
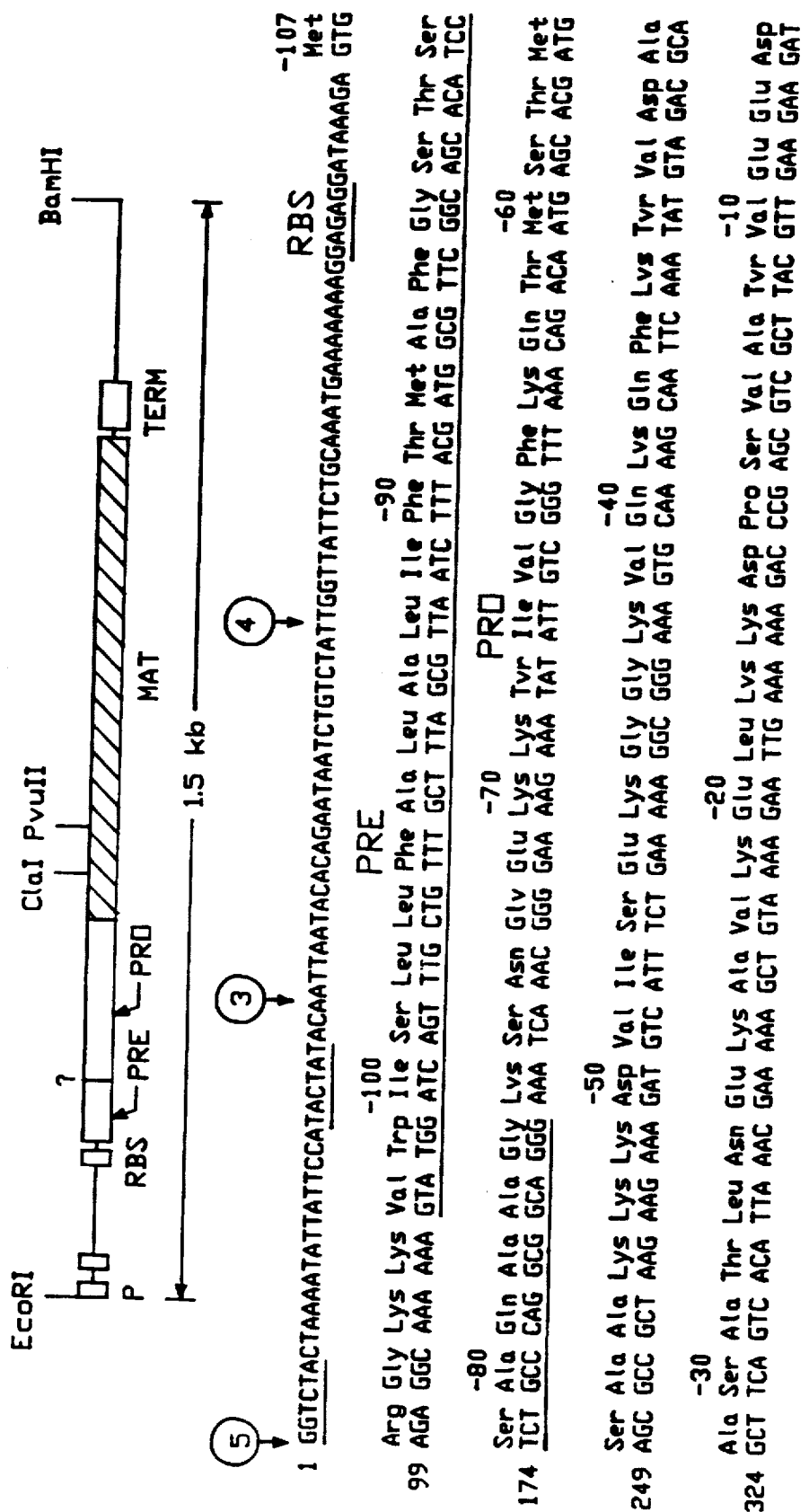

The bleaching compositions employed in the present invention provide effective and efficient cleaning of fabrics which thereby removes stains and/or soils from the fabrics. The bleaching systems in combination with the protease enzyme are particularly efficient at removing most types of soils from the fabrics, including protein and lipid soils, dingy soils, and heavy soil loads, especially from nucleophilic and body soils.

The protease enzymes, bleaching agents (including peroxyacids and bleaching systems) and cleaning composition materials useful herein, including preferred levels, are described in detail hereinafter.

(1) Bleaching Agent

The bleaching compositions herein contain a bleaching agent, which preferably comprises from about 0.5 to about 20 wt. % of the composition. The bleaching agent is either a substantially insoluble, preferably solid, organic peroxyacid, or a bleaching system comprising a bleach activator and a peroxygen bleaching compound capable of yielding hydrogen peroxide, or a combination of both. The peracid which is in the composition, or which is formed by the combination of activator and peroxygen compound, preferably has a corresponding carboxylic acid that has a Hydrophilic-Lipophilic Balance ("H.L.B.") value which ranges from about 3 to about 6.5. Therefore, a method that can be used to characterize the preferred peroxyacids (from activators or as preformed peroxyacids) which are useful in the present invention is the "H.L.B. Scale" such as that described in Davies, J. T., *Proc 2nd Internat. Congr. Surface Activity* 1,. 426, Butterworths, London (1957), incorporated herein by reference. Such an H.L.B. Scale (Hydrophilic-Lipophilic Balance) has been used in the study of surface-active agents (surfactants) as a means to relate the distribution of a surface-active agent between a hydrophilic (water-like) and a lipophilic (oil-like) phase. In this manner, H.L.B. values can be used as an indication of the lipophilic (hydrophobic) character of the active bleaching species in the wash (i.e., the ability of the peroxyacid to partition out of the wash liquor and concentrate at the soil/fabric interface).

Set forth hereinafter in Table A are H.L.B. values which have been calculated for selected peroxyacids (as the corresponding carboxylic acids). The equation used to calculate the H.L.B. values can be set forth as:

*HLB*=Sum (Hydrophilic Group Numbers)–Sum (Hydrophobic Group Numbers)+7.

The values for the Hydrophilic Group Numbers am [—C(O)OH &—N(H)C(O)—=2.1] and the values for the Hydrophobic Group Numbers are [aliphatic/aromatic carbon= 0.475 & aliphatic carbon atoms between polar groups are ½ the value of an aliphatic carbon in a hydrocarbon chain= (0.475)/2]. For reference, an H.L.B. value>7 indicates that the material is preferentially water soluble and an H.L.B. value<7 indicates increasing surface-activity and hydrophobicity.

TABLE A

H.L.B. Value Provided by Various Peroxyacids

| Activator/Preformed Peroxyacid | Abbreviation | Peroxyacid | H.L.B. Corresponding Carboxylic Acid |
|---|---|---|---|
| Tetra Acetyl Ethylene Diamine | TAED | $CH_3C(O)OOH$ | 8.6 |
| DiPeroxyDodecane Dioic Acid | DPDDA | $HOO(O)C(CH_2)_{10}-C(O)OOH$ | 6.5 |
| Nonyl Amide of Peroxy Succinic Acid | NAPSA | $CH_3(CH_2)_8N(H)-C(O)(CH_2)_2C(O)-OOH$ | 6.4 |
| BenzoylOxyBenzene Sulfonate | BOBS | $C_6H_5C(O)OOH$ | 6.3 |
| Nonyl Amide of Peroxy Adipic Acid | NAPAA | $CH_3(CH_2)_8N(H)-C(O)(CH_2)_4C(O)-OOH$ | 6.0 |
| NonanoylOxyBenzene Sulfonate | NOBS | $CH_3(CH_2)_7C(O)-OOH$ | 5.3 |
| DecanoylOxyBenzene Sulfonate | DOBS | $CH_3(CH_2)_8C(O)-OOH$ | 4.8 |
| PerLauric Acid | PLA | $CH_3(CH_2)_{10}C-(O)OOH$ | 3.9 |

As noted hereinbefore, a preferred range of H.L.B. values (of the corresponding carboxylic acid) for the peroxyacids of the present invention (whether added directly or generated in situ) ranges from about 3.0 to about 6.5. A more preferred range of H.L.B. values (as the carboxylic acid) for the peroxyacids useful in the present invention (whether added directly or generated in situ) range from about 4.0 to 6.5. The most preferred range of H.L.B. values (as the carboxylic acid) for the peroxyacids of the present invention (whether added directly as generated in situ) ranges from about 4.0 to about 6.0.

(a) Peroxyacid

The present invention encompasses detergent compositions comprising an effective amount of the protease enzyme and a bleaching system comprising at least about 0.1%, preferably from about 0.1% to about 50%, by weight, of a substantially insoluble organic peroxyacid. The peroxyacid useful herein preferably comprises from about 0.5 to about 20, more preferably from about 1 to about 10, most preferably from about 2 to about 7, wt. % of the composition.

Preferred organic peroxyacids are selected from the group consisting of 4-nonylamino-4-oxoperoxybutyric acid; 6-(nonyl-amino)-6-oxoperoxycaproic acid; 1,12-diperoxydodecanedioic acid; heptyl sulfonylperpropionic acid; decylsulphonyl perpropionic acid; and heptyl-octyl-, nonyl-, decyl-sulphonylperbutyric acid; and mixtures thereof.

Of the organic peroxyacids, amidoperoxyacids (amide substituted peroxycarboxylic acids) are preferred. Suitable amidoperoxyacids for use herein are described in U.S. Pat. Nos. 4,634,551 and 4,686,063, both Burns et al., issued Jan. 6, 1987 and Aug. 11, 1987, respectively, both incorporated herein by reference. Suitable amidoperoxyacids are of the formula:

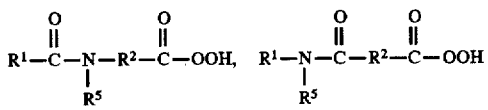, 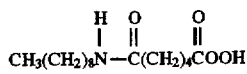

wherein $R^1$ is an alkyl, aryl, or alkaryl group containing from about 1 to about 14 carbon atoms (preferably $R^1$ is an alkyl group containing from about 6 to about 12 carbon atoms), $R^2$ is an alkylene, arylene or alkarylene group containing from about 1 to about 14 carbon atoms (preferably $R^2$ is an alkylene group containing from about 1 to about 6 carbon atoms), and $R^5$ is H or an alkyl, aryl, or alkaryl group containing from about 1 to about 10 carbon atoms (preferably $R^5$ is H). More preferably, $R^1$ is an alkyl group containing from about 8 to about 10 carbon atoms, and $R^2$ is an alkylene group containing from about 2 to about 4 carbon atoms Also suitable for use herein are peroxyfumarates, which are described in U.S. Pat. No. 4,852,989, Burns et al., issued Aug. 1, 1989, incorporated herein by reference, and sulfone peroxyacids (sulfone peroxycarboxylic acids), which are described in U.S. Pat. Nos. 4,758,369, 4,824,591, and 5,004,558, all Dryoff et al., issued Jul. 19, 1988, Apr. 25, 1989, and Apr. 2, 1991, respectively, all incorporated herein by reference.

Example I of U.S. Pat. No. 4,686,063 contains one description of the synthesis of NAPSA, from column 8, line 40 to column 9, line 5, and NAPAA, from column 9, line 15 to column 9, line 65. At the end of the amidoperoxyacid synthesis, the reaction is quenched with water, filtered, washed with water to remove some excess sulfuric acid (or other strong acid with which the peroxyacid was made), and filtered again.

The amidoperoxyacid wet cake thus obtained can be contacted with a phosphate buffer solution at a pH between about 3.5 and 6, preferably between about 4 and 5, according to U.S. Pat. No. 4,909,953, Sadlowski et al., issued Mar. 20, 1990, which is incorporated herein by reference.

Other agents for storage stabilization or exotherm control can be added to the amidoperoxyacid before incorporation into the final product. For example, boric acid, an exotherm control agent disclosed in U.S. Pat. No. 4,686,063, Burns, issued Aug. 11, 1987 and incorporated herein, can be mixed with the amidoperoxyacid (which has been washed in phosphate buffer) in about a 2:1 peracid:boric acid ratio. The phosphate buffer washed amidoperoxyacid can also be mixed with appropriate amounts of dipicolinic acid and tetrasodium pyrophosphate, a chelating stabilization system. Chelants can optionally be included in the phosphate buffer before contact with the wet cake.

The wet cake is preferably made up of particles with an average particle diameter of from about 0.1 to about 260 microns, preferably from about 10 to about 100 microns, and most preferably from about 30 to about 60 microns. Small particle size NAPAA crystals are desired herein. See U.S. Pat. No. 5,055,218, Getty et al., issued Oct. 8, 1991, which is incorporated herein by reference.

NAPAA filter cake herein is preferably washed twice in phosphate buffer. It has been found that two successive phosphate buffer washes lend optimal stability to NAPAA.

Particulate (solid), organic peroxyacids with a theoretical AvO (available oxygen) of between about 3 and about 12, most preferably between 5 and 7, are preferred.

Most preferred for use herein is NAPAA. Another name for the nonylamide of peroxyadipic acid ("NAPAA") is 6-(nonylamino)-6-oxoperoxycaproic acid. The chemical formula for NAPAA is:

$$CH_3(CH_2)_8N(H)-C(O)(CH_2)_4C(O)OOH$$

The molecular weight of NAPAA is 287.4.

Detergent compositions and bleaching compositions containing NAPAA provide extremely effective and efficient surface bleaching of textiles. Stains and/or soils are removed from the textiles. These compositions are particularly effective at removing dingy soils from textiles.

NAPAA's polar amide or substituted amide moiety results in a peroxyacid which has a very low vapor pressure and thus possesses a low odor profile as well as excellent bleaching performance. It is believed that the polarity of the amide group results in a reduction of vapor pressure of the peroxyacid, and an increase in melting point.

NAPAA can be used directly as a bleaching agent. It has a reduced vapor pressure and a good odor profile in laundry applications.

NAPAA can be prepared by, for example, first reacting NAAA (monononyl amide of adipic acid), sulfuric acid, and hydrogen peroxide. The reaction product is quenched by addition to ice water followed by filtration, washing with distilled water, and final suction filtration to recover the wet cake. Washing can be continued until the pH of the filtrate is neutral.

It is also preferred that the NAPAA pH (10% solids in water) be between about 4.2 and 4.8. Surprisingly, this pH results in more thermally stable particles.

(b) Bleaching Systems—Bleach Activator and Peroxygen Bleaching Compound
  (i) Bleach Activators The bleach activator for the bleaching systems useful herein preferably has the following structure:

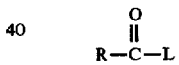

wherein R is an alkyl group containing from about 5 to about 18 carbon atoms wherein the longest linear alkyl chain extending from and including the carbonyl carbon contains from about 6 to about 10 carbon atoms and L is a leaving group, the conjugate acid of which has a pKa in the range of from about 4 to about 13, preferably from about 6 to about 11, most preferably from about 8 to about 11.

L can be essentially any suitable leaving group. A leaving group is any group that is displaced from the bleach activator as a consequence of the nucleophilic attack on the bleach activator by the perhydroxide anion. This, the perhydrolysis reaction, results in the formation of the percarboxylic acid. Generally, for a group to be a suitable leaving group it must exert an electron attracting effect. This facilitates the nucleophilic attach by the perhydroxide anion.

The L group must be sufficiently reactive for the reaction to occur within the optimum time frame (e.g., a wash cycle). However, if L is too reactive, this activator will be difficult to stabilize. These characteristics are generally paralleled by the pKa of the conjugate acid of the leaving group, although exceptions to this convention are known.

Preferred bleach activators are those of the general formula:

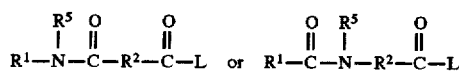

wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is selected from the group consisting of:

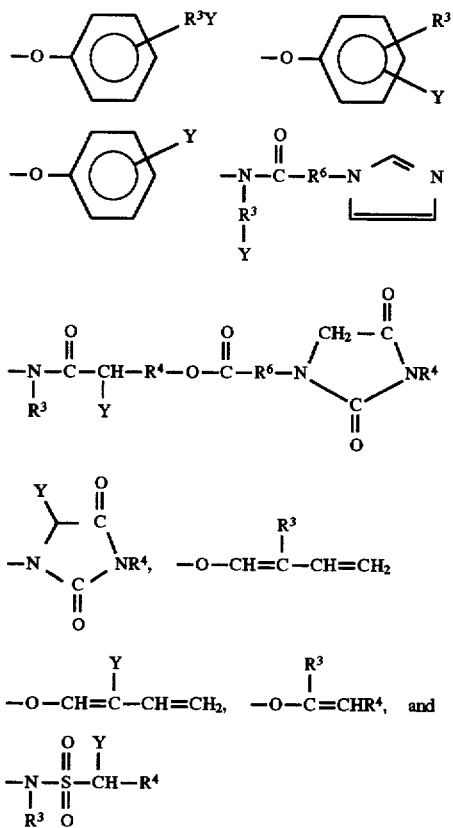

wherein $R^6$ is an alkylene, arylene, or alkarylene group containing from about 1 to about 14 carbon atoms, $R^3$ is an alkyl chain containing from about 1 to about 8 carbon atoms, $R^4$ is H or $R^3$, and Y is H or a solubilizing group. Y is preferably selected from the group consisting of —$SO_3$—M+, —COO—M+, —$SO_4$—M+, (—N+$R'_3$)X— and O←N ($R'_3$), wherein R' is an alkyl chain containing from about 1 to about 4 carbon atoms, M is a cation which provides solubility to the bleach activator and X is an anion which provides solubility to the bleach activator. Preferably, M is an alkali metal, ammonium or substituted ammonium cation, with sodium and potassium being most preferred, and X is an anion selected from the group consisting of halide, hydroxide, methylsulfate and acetate anions. More preferably, Y is —$SO_3$—M+ and —COO—M+. It should be noted that bleach activators with a leaving group that does not contain a solubilizing group should be well dispersed in the bleach solution in order to assist in their dissolution. Preferred is:

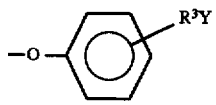

wherein $R^3$ is as defined above and Y is —$SO_3$—M+ or —COO—M+ wherein M is as defined above.

Especially preferred bleach activators are those wherein $R^1$ is a linear alkyl chain containing from about 6 to about 12 carbon atoms, $R^2$ is a linear alkylene chain containing from about 2 to about 6 carbon atoms, $R^5$ is H, and L is selected from the group consisting of:

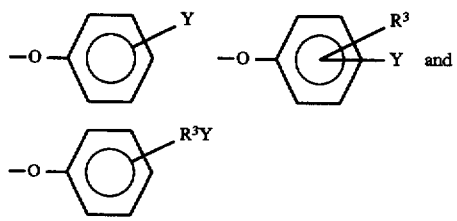

wherein $R^3$ is as defined above, Y is —$SO_3$—M+ or —COO—M+ and M is as defined above.

A preferred bleach activator is:

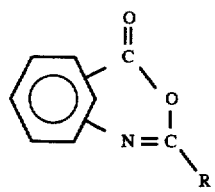

wherein R is H, alkyl, aryl or alkaryl. This is described in U.S. Pat. No. 4,966,723, Hodge et al., incorporated by reference herein.

Preferred bleach activators are:

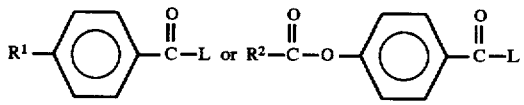

wherein $R^1$ is H or an alkyl group containing from about 1 to about 6 carbon atoms and $R^2$ is an alkyl group containing from about 1 to about 6 carbon atoms and L is as defined above.

Preferred bleach activators are also those of the above general formula wherein L is as defined in the general formula, and $R^1$ is H or an alkyl group containing from about 1 to about 4 carbon atoms.

Even more preferred are bleach activators of the above general formula wherein L is as defined in the general formula and $R^1$ is a H.

More preferred bleach activators are those of the above general formula wherein R is a linear alkyl chain containing from about 5 to about 9 and preferably from about 6 to about 8 carbon atoms and L is selected from the group consisting of:

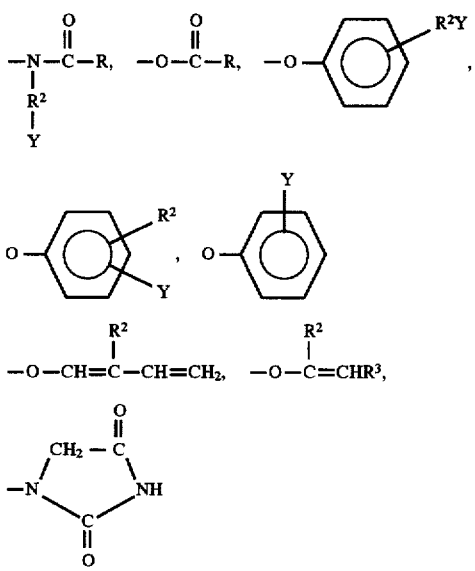

wherein R, R², R³ and Y are as defined above.

Particularly preferred bleach activators are those of the above general formula wherein R is an alkyl group containing from about 5 to about 12 carbon atoms wherein the longest linear portion of the alkyl chain extending from and including the carbonyl carbon is from about 6 to about 10 carbon atoms, and L is selected from the group consisting of:

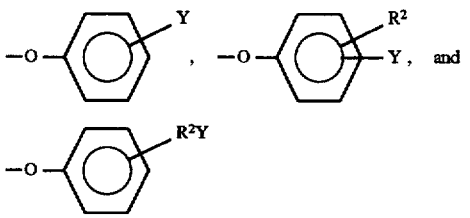

wherein R² is an alkyl chain containing from about 1 to about 8 carbon atoms, and Y is —SO—₃M+ or —COO—M+ wherein M is an alkali metal, ammonium or substituted ammonium cation.

Especially preferred bleach activators are those of the above general formula wherein R is a linear alkyl chain containing from about 5 to about 9 and preferably from about 6 to about 8 carbon atoms and L is selected from the group consisting of:

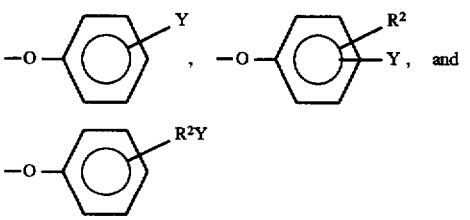

wherein R² is as defined above and Y is —SO—₃M+ or —COO—M+ wherein M is as defined above.

The most preferred bleach activators have the formula:

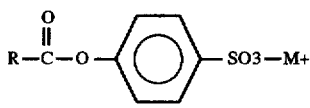

wherein R is a linear alkyl chain containing from about 5 to about 9 and preferably from about 6 to about 8 carbon atoms and M is sodium or potassium.

Preferably, the bleach activator herein is sodium nonanoyloxybenzenesulfonate (NOBS) or sodium benzoyloxybenzenesulfonate (BOBS).

Further particularly preferred for use in the present invention bleaching compositions are the following bleach activators which are particularly safe for use with machines having natural rubber parts. This is believed to be the result of not producing oily diacylperoxide (DAP) species by the perhydrolysis reaction of these amido acid-derived bleach activators, but rather forming insoluble crystalline solid DAP's. These solids are believed to not form a coating film and thus natural rubber parts are not exposed to DAP's for extended periods of time. These preferred bleach activators are members selected from the group consisting of:

a) a bleach activator of the general formula:

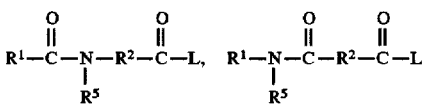

or mixtures thereof, wherein $R^1$ is an alkyl, aryl, or alkaryl group containing from about 1 to about 14 carbon atoms, $R^2$ is an alkylene, arylene or alkarylene group containing from about 1 to about 14 carbon atoms, $R^5$ is H or an alkyl, aryl, or alkaryl group containing from about 1 to about 10 carbon atoms, and L is a leaving group;

b) benzoxazin-type bleach activators of the general formula:

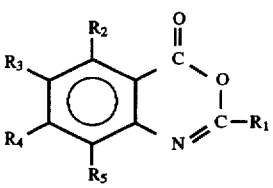

wherein $R_1$ is H, alkyl, alkaryl, aryl, arylalkyl, and wherein $R_2$, $R_3$, $R_4$, and $R_5$ may be the same or different substituents selected from H, halogen, alkyl, alkenyl, aryl, hydroxyl, alkoxyl, amino, alkylamino, $COOR_6$ (wherein $R_6$ is H or an alkyl group) and carbonyl functions;

c) N-acyl caprolactam bleach activators of the formula:

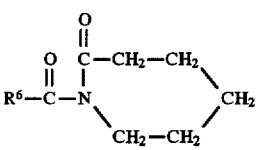

wherein $R^6$ is H or an alkyl, aryl, alkoxyaryl or alkaryl group containing from 1 to 12 carbons; and d) mixtures of a), b) and c).

Preferred bleach activators of type a) are those wherein $R^1$ is an alkyl group containing from about 6 to about 12 carbon atoms, $R^2$ contains from about 1 to about 8 carbon atoms, and $R^5$ is H or methyl. Particularly preferred bleach activators are those of the above general formulas wherein $R^1$ is an alkyl group containing from about 7 to about 10 carbon atoms and $R^2$ contains from about 4 to about 5 carbon atoms.

Preferred bleach activators of type b) are those wherein $R_2$, $R_3$, $R_4$, and $R_5$ are H and $R_1$ is a phenyl group.

The preferred acyl moieties of said N-acyl caprolactam bleach activators of type c) have the formula $R^6$—CO— wherein $R^6$ is H or an alkyl, aryl, alkoxyaryl, or alkaryl group containing from 1 to 12 carbons, preferably from 6 to 12 carbon atoms. In highly preferred embodiments, $R^6$ is a member selected from the group consisting of phenyl, heptyl, octyl, nonyl, 2,4,4-trimethylpentyl, decenyl and mixtures thereof.

Amido Derived Bleach Activators—The bleach activators of type a) employed in the present invention are amide substituted compounds of the general formulas:

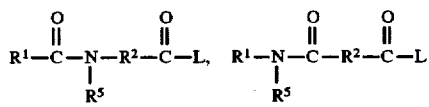

or mixtures thereof, wherein $R^1$, $R^2$ and $R^5$ are as defined above and L can be essentially any suitable leaving group. Preferred bleach activators are those of the above general formula wherein $R^1$, $R^2$ and $R^5$ are as defined for the peroxyacid and L is selected from the group consisting of:

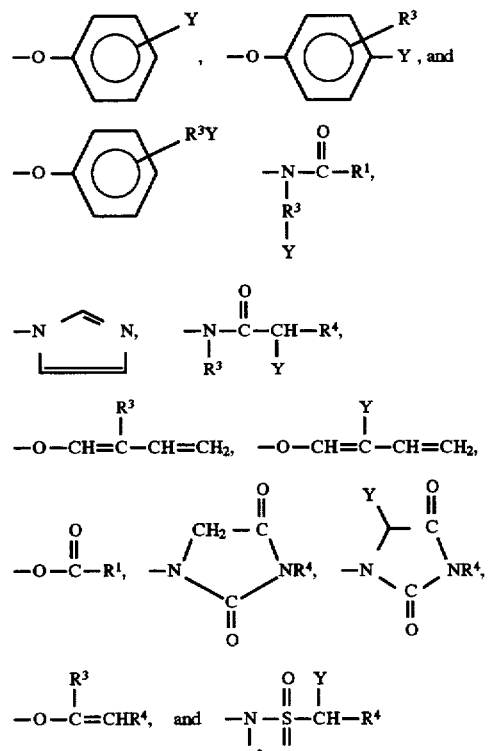

and mixtures thereof, wherein $R^1$ is an alkyl, aryl, or alkaryl group containing from about 1 to about 14 carbon atoms, $R^{13}$ is an alkyl chain containing from 1 to about 8 carbon atoms, $R^4$ is H or $R^3$, and Y is H or a solubilizing group.

The preferred solubilizing groups are —$SO_3^-M^+$, —$CO_2^-M^+$, —$SO_4^-M^+$, —$N^+(R^3)_4X^-$ and $O<N(R^3)_3$ and most preferably—$SO_3^-M^+$ and —$CO_2^-M^+$ wherein $R^3$ is an alkyl chain containing from about 1 to about 4 carbon atoms, M is a cation which provides solubility to the bleach activator and X is an anion which provides solubility to the bleach activator. Preferably, M is an alkali metal, ammonium or substituted ammonium cation, with sodium and potassium being most preferred, and X is a halide, hydroxide, methylsulfate or acetate anion. It should be noted that bleach activators with a leaving group that does not contain a solubilizing groups should be well dispersed in the bleaching solution in order to assist in their dissolution.

Preferred bleach activators are those of the above general formula wherein L is selected from the group consisting of:

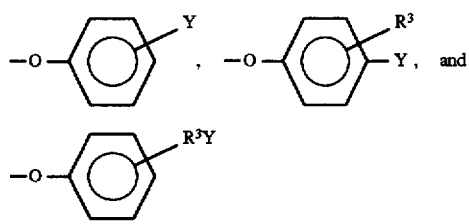

wherein $R^3$ is as defined above and Y is —$SO_3^-M^+$ or —$CO_2^-M^+$ wherein M is as defined above.

Another important class of bleach activators, including those of type b) and type c), provide organic peracids as described herein by ring-opening as a consequence of the nucleophilic attack on the carbonyl carbon of the cyclic ring by the perhydroxide anion. For instance, this ring-opening reaction in type c) activators involves attack at the caprolactam ring carbonyl by hydrogen peroxide or its anion. Since attack of an acyl caprolactam by hydrogen peroxide or its anion occurs preferably at the exocyclic carbonyl, obtaining a significant fraction of ring-opening may require a catalyst. Another example of ring-opening bleach activators can be found in type b) activators, such as those disclosed in U.S. Pat. No. 4,966,723, Hodge et al, issued Oct. 30, 1990.

Benzoxazin-type Bleach Activators—Such activator compounds disclosed by Hodge include the activators of the benzoxazin-type, having the formula:

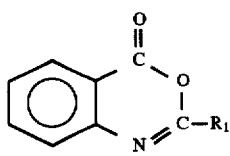

including the substituted benzoxazins of the type

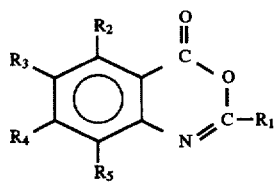

wherein $R_1$ is H, alkyl, alkaryl, aryl, arylalkyl, and wherein $R_2$, $R_3$, $R_4$, and $R_5$ may be the same or different substituents selected from H, halogen, alkyl, alkenyl, aryl, hydroxyl, alkoxyl, amino, alkyl amino, $COOR_6$ (wherein $R_6$ is H or an alkyl group) and carbonyl functions.

A preferred activator of the benzoxazin-type is:

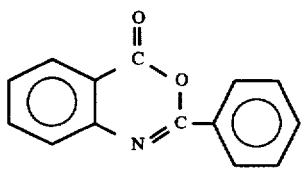

When the activators are used, optimum surface bleaching performance is obtained with washing solutions wherein the pH of such solution is between about 8.5 and 10.5 and preferably between 9.5 and 10.5 in order to facilitate the perhydrolysis reaction. Such pH can be obtained with substances commonly known as buffering agents, which are optional components of the bleaching systems herein.

N-Acyl Caprolactam Bleach Activators—The N-acyl caprolactam bleach activators of type c) employed in the present invention have the formula:

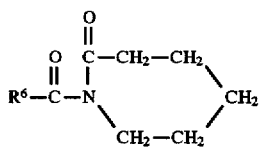

wherein $R^6$ is H or an alkyl, aryl, alkoxyaryl, or alkaryl group containing from 1 to 12 carbons. Caprolactam activators wherein the $R^6$ moiety contains at least about 6, preferably from 6 to about 12, carbon atoms provide hydrophobic bleaching which affords nucleophilic and body soil clean-up, as noted above. Caprolactam activators wherein $R^6$ comprises from 1 to about 6 carbon atoms provide hydrophilic bleaching species which are particularly efficient for bleaching beverage stains. Mixtures of hydrophobic and hydrophilic caprolactams, typically at weight ratios of 1:5 to 5:1, preferably 1:1, can be used herein for mixed stain removal benefits.

Highly preferred N-acyl caprolactams are selected from the group consisting of benzoyl caprolactam, octanoyl caprolactam, nonanoyl caprolactam, 3,5,5-trimethylhexanoyl caprolactam, decanoyl caprolactam, undecenoyl caprolactam, and mixtures thereof. Methods for making N-acyl caprolactams are well known in the art.

Contrary to the teachings of U.S. Pat. No. 4,545,784, the bleach activator is preferably not absorbed onto the peroxygen bleaching compound. To do so in the presence of other organic detersive ingredients could cause safety problems.

The bleach activators of type a), b) or c) will comprise at least about 0.1%, preferably from about 0.1% to about 50%, more preferably from about 1% to about 30%, most preferably from about 3% to about 25%, by weight of bleaching system or detergent composition.

The preferred amido-derived and caprolactam bleach activators herein can also be used in combination with rubber-safe, enzyme-safe, hydrophilic activators such as TAED, typically at weight ratios of amido-derived or caprolactam activators:TAED in the range of 1:5 to 5:1, preferably about 1:1.

The bleaching mechanism generally, and the surface bleaching mechanism in particular, are not completely understood. However, it is generally believed that the bleach activator undergoes nucleophilic attack by a perhydroxide anion, which is generated from the hydrogen peroxide evolved by the peroxygen bleach, to form a peroxycarboxylic acid. This reaction is commonly referred to as perhydrolysis.

When the activators are used, optimum surface bleaching performance is obtained with washing solutions wherein the pH of such solution is between about 8.5 and 10.5 and preferably between 9.5 and 10.5 in order to facilitate the perhydrolysis reaction. Such pH can be obtained with substances commonly known as buffering agents, which are optional components of the bleaching systems herein.

(ii) The Peroxygen Bleaching Compound

The peroxygen bleaching systems useful herein are those capable of yielding hydrogen peroxide in an aqueous liquor. These compounds are well known in the art and include hydrogen peroxide and the alkali metal peroxides, organic peroxide bleaching compounds such as urea peroxide, and inorganic persalt bleaching compounds, such as the alkali metal perborates, percarbonates, perphosphates, and the like. Mixtures of two or more such bleaching compounds can also be used, if desired.

Preferred peroxygen bleaching compounds include sodium perborate, commercially available in the form of mono-, tri-, and tetrahydrate, sodium pyrophosphate peroxyhydrate, urea peroxyhydrate, sodium percarbonate, and sodium peroxide. Particularly preferred are sodium perborate tetrahydrate, sodium perborate monohydrate and sodium percarbonate. Percarbonate is especially preferred because it is very stable during storage and yet still dissolves very quickly in the bleaching liquor. It is believed that such rapid dissolution results in the formation of higher levels of percarboxylic acid and, thus, enhanced surface bleaching performance.

Highly preferred percarbonate can be in uncoated or coated form. The average particle size of uncoated percarbonate ranges from about 400 to about 1200 microns, most preferably from about 400 to about 600 microns. If coated percarbonate is used, the preferred coating materials include mixtures of carbonate and sulphate, silicate, borosilicate, or fatty carboxylic acids.

The peroxygen bleaching compound will comprise at least about 0.1%, preferably from about 1% to about 75%, more preferably from about 3% to about 40%, most preferably from about 3% to about 25%, by weight of bleaching system or detergent composition.

The weight ratio of bleach activator to peroxygen bleaching compound in the bleaching system typically ranges from about 2:1 to 1:5. Preferred ratios range from about 1:1 to about 1:3.

The molar ratio of hydrogen peroxide yielded by the peroxygen bleaching compound to the bleach activator is greater than about 1.0, more preferably greater than about 1.5, and most preferably from about 2.0 to about 10. Preferably, the bleaching compositions herein comprise from about 0.5 to about 20, most preferably from about 1 to about 10, wt. % of the peroxygen bleaching compound.

The bleach activator/bleaching compound systems herein are useful per se as bleaches. However, such bleaching systems are especially useful in compositions which can comprise various detersive adjuncts such as surfactants, builders and the like.

(2) Protease Enzymes:

The invention includes protease enzymes which are non-naturally-occurring carbonyl hydrolase variants having a different proteolytic activity, stability, substrate specificity, pH profile and/or performance characteristic as compared to the precursor carbonyl hydrolase from which the amino acid sequence of the variant is derived. The precursor carbonyl hydrolase may be a naturally-occurring carbonyl hydrolase or recombinant hydrolase. Specifically, such carbonyl hydrolase variants have an amino acid sequence not found in nature, which is derived by replacement of a plurality of amino acid residues of a precursor carbonyl hydrolase with different amino acids. The plurality of amino acid residues of the precursor enzyme correspond to position +76 in combination with one or more of the following residues +99, +101, +103, +104, +107, +123, +27, +105, +109, +126, +128, +135, +156, +166, +195, +197, +204, +206, +210, +216, +217, +218, +222, +260, +265, and/or +274, where the numbered position corresponds to naturally-occurring subtilisin from *Bacillus amyloliquefaciens* or to equivalent amino acid residues in other carbonyl hydrolases or subtilisins, such as *Bacillus lentus* subtilisin.

The carbonyl hydrolase variants which are protease enzyme useful in the present invention compositions comprise replacement of amino acid residue +76 in combination with one or more additional modifications. Preferably the variant protease enzymes useful for the present invention comprise the substitution, deletion or insertion of amino acid residues in the following combinations: 76/99; 76/101; 76/103; 76/104; 76/107; 76/123; 76/99/101; 76/99/103; 76/99/104; 76/101/103; 76/101/104; 76/103/104; 76/104/107; 76/104/123; 76/107/123; 76/99/101/103; 76/99/101/104; 76/99/103/104; 76/101/103/104; 76/103/104/123; 76/104/107/123; 76/99/101/103/104; 76/99/103/104/123; 76/99/101/103/104/123; 76/103/104/128; 76/103/104/260; 76/103/104/265; 76/103/104/197; 76/103/104/105; 76/103/104/135; 76/103/104/126; 76/103/104/107; 76/103/104/210; 76/103/104/126/265; and/or 76/103/104/222. Most preferably the variant enzymes useful for the present invention comprise the substitution, deletion or insertion of an amino acid residue in the following combination of residues: 76/99; 76/104; 76/99/104; 76/103/104; 76/104/107; 76/101/103/104; 76/99/101/103/104 and 76/101/104 of *B. amyloliquefaciens* subtilisin.

Variant DNA sequences encoding such carbonyl hydrolase or subtilisin variants are derived from a precursor DNA sequence which encodes a naturally-occurring or recombinant precursor enzyme. The variant DNA sequences are derived by modifying the precursor DNA sequence to encode the substitution of one or more specific amino acid residues encoded by the precursor DNA sequence corresponding to positions 76, 99, 101, 103, 104, 107, 123, 27, 105, 109, 126, 128, 135, 156, 166, 195, 197, 204, 206, 210, 216, 217, 218, 222, 260, 265 and/or 274, in *Bacillus amyloliquefaciens* or any combination thereof. Although the amino acid residues identified for modification herein are identified according to the numbering applicable to *B. amyloliquefaciens* (which has become the conventional method for identifying residue positions in all subtilisins), the preferred precursor DNA sequence useful for the present invention is the DNA sequence of *Bacillus lentus* as shown in FIG. 6 (Seq. ID No. 11).

These variant DNA sequences encode the insertion or substitution of the amino acid residue 76 in combination with one or more additional modification. Preferably the variant DNA sequences encode the substitution or insertion of amino acid residues in the following combinations: 76/99; 76/101; 76/103; 76/104; 76/107; 76/123; 76/99/101; 76/99/103; 76/99/104; 76/101/103; 76/101/104; 76/103/104; 76/104/107; 76/104/123; 76/107/123; 76/99/101/103; 76/99/101/104 76/99/103/104; 76/101/103/104; 76/103/104/123; 76/104/107/123; 76/99/101/103/104; 76/99/103/104/123; 76/99/101/103/104/123; 76/103/104/128; 76/103/104/260; 76/103/104/265; 76/103/104/197; 76/103/104/105; 76/103/104/135; 76/103/104/126; 76/103/104/107; 76/103/104/210; 76/103/104/126/265; and/or 76/103/104/222. Most preferably the variant DNA sequences encode for the modification of the following combinations of residues: 76/99; 76/104; 76/99/104; 76/103/104; 76/104/107; 76/101/103/104; 76/99/101/103/104 and 76/101/104. These recombinant DNA sequences encode carbonyl hydrolase variants having a novel amino acid sequence and, in general, at least one properly which is substantially different from the same property of the enzyme encoded by the precursor carbonyl hydrolase DNA sequence. Such properties include proteolytic activity, substrate specificity, stability, altered pH profile and/or enhanced performance characteristics.

The protease enzymes useful herein encompass the substitution of any of the nineteen naturally occurring L-amino acids at the designated amino acid residue positions. Such substitutions can be made in any precursor subtilisin (procaryotic, eucaryotic, mammalian, etc.). Thoughout this application reference is made to various amino acids by way of common one- and three-letter codes. Such codes are identified in Dale, J. W., (1989), *Molecular Genetics of Bacteria*, John Wiley & Sons, Ltd., Appendix B.

Preferably, the substitution to be made at each of the identified amino acid residue positions include but are not limited to: substitutions at position 76 including D, H, E, G, F, K, P and N; substitutions at position 99 including D, T, N, Q, G and S; substitutions at position 101 including G, D, K, L, A, E, S and R; substitutions at position 103 including Q, T, D, E, Y, K, G, R, S, and A; substitutions at position 104 including all nineteen naturally-occurring amino acids; substitutions at position 107 including V, L, M, Y, G, E, F, T, S, A, N and I; substitutions at position 123 including N, T, I, G, A, C, and S; substitutions at position 27 including K, N, C, V and T; substitutions at position 105 including A, D, G, R and N; substitutions at position 107 including A, L, V, Y, G, F, T, S and A; substitutions at position 109 including S, K, R, A, N and D; substitutions at position 126 including A, F, I, V and G; substitutions at position 128 including G, L and A; substitutions at position 135 including A, F, I, S and V; substitutions at position 156 including D, E, A, G, Q and K; substitutions at position 166 including all nineteen naturally-occurring amino acids; substitutions at position 195 including E; substitutions at position 197 including E; substitutions at position 204 including A, G, C, S and D; substitutions at position 206 including L, Y, N, D and E; substitutions at position 210 including L, I, S, C and F; substitutions at position 216 including V, E, T and K; substitutions at position 217 including all nineteen naturally-occurring amino acids; substitutions at position 218 including S, A, G, T and V; substitutions at position 222 including all nineteen naturally-occurring amino acids; substitutions at position 260 including P, N, G, A, S, C, K and D; substitutions at position including N, G, A, S, C, K, Y and H; and substitutions at position 274 including A and S. The specifically preferred amino acid(s) to be substituted at each such position are designated below in Table I. Although specific amino acids are shown in Table I, it should be understood that any amino acid may be substituted at the identified residues.

TABLE I

| Amino Acid Residue | Preferred Amino Acid to be Substituted/Inserted |
|---|---|
| +76 | D, H |
| +99 | D, T, N, G |
| +101 | R, G, D, K, L, A, E |
| +103 | A, Q, T, D, E, Y, K, G, R |
| +104 | I, Y, S, L, A, T, G, F, M, W, D, V, N |
| +107 | V, L, Y, G, F, T, S, A, N |
| +123 | S, T, I |

TABLE I-continued

| Amino Acid Residue | Preferred Amino Acid to be Substituted/Inserted |
|---|---|
| +27 | K |
| +105 | A, D |
| +109 | S, K, R |
| +126 | A, I, V, F |
| +128 | G, L |
| +135 | I, A, S |
| +156 | E, D, Q |
| +166 | D, G, E, K, N, A, F, I, V, L |
| +195 | E |
| +197 | E |
| +204 | A, G, C |
| +206 | L |
| +210 | I, S, C |
| +216 | V |
| +217 | H, I, Y, C, A, G, F, S, N, E, K |
| +218 | S |
| +222 | A, Q, S, C, I, K |
| +260 | P, A, S, N, G |
| +265 | N, A, G, S |
| +274 | A, S |

These protease enzymes containing in vitro mutations in *B. lentus* subtilisin at an amino acid residue equivalent to +76 in *Bacillus amyloliquefaciens* subtilisin produces subtilisin variants exhibiting altered stability (e.g., modified autoproteolytic stability) over precursor subtilisins. (See Tables IV and VI.)

Also, in vitro mutation at residues equivalent to +99, +101, +103, +104, +107, +123, +27, +105, +109, +126, +128, +135, +156, +166, +195, +197, +204, +206, +210, +216, +217, +218, +222, +260, +265, and/or +274 in *Bacillus amyloliquefaciens* subtilisin, alone or in combination with each other and in any combination with +76 mutations, produce subtilisin variants exhibiting altered proteolytic activity, altered thermal stability, altered pH profile, altered substrate specificity and/or altered performance characteristics.

Carbonyl hydrolases are protease enzymes which hydrolyze compounds containing

bonds in which X is oxygen or nitrogen. They include naturally-occurring carbonyl hydrolases and recombinant carbonyl hydrolases. Naturally-occurring carbonyl hydrolases principally include hydrolases, e.g., peptide hydrolases such as subtilisins or metalloproteases. Peptide hydrolases include α-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases.

"Recombinant carbonyl hydrolase" refers to a carbonyl hydrolase in which the DNA sequence encoding the naturally-occurring carbonyl hydrolase is modified to produce a mutant DNA sequence which encodes the substitution, insertion or deletion of one or more amino acids in the carbonyl hydrolase amino acid sequence. Suitable modification methods are disclosed herein, and in U.S. Pat. Nos. 4,760,025 (Re. 34,606), 5,204,015 and 5,185,258, the disclosure of which are incorporated herein by reference.

Figure 3:
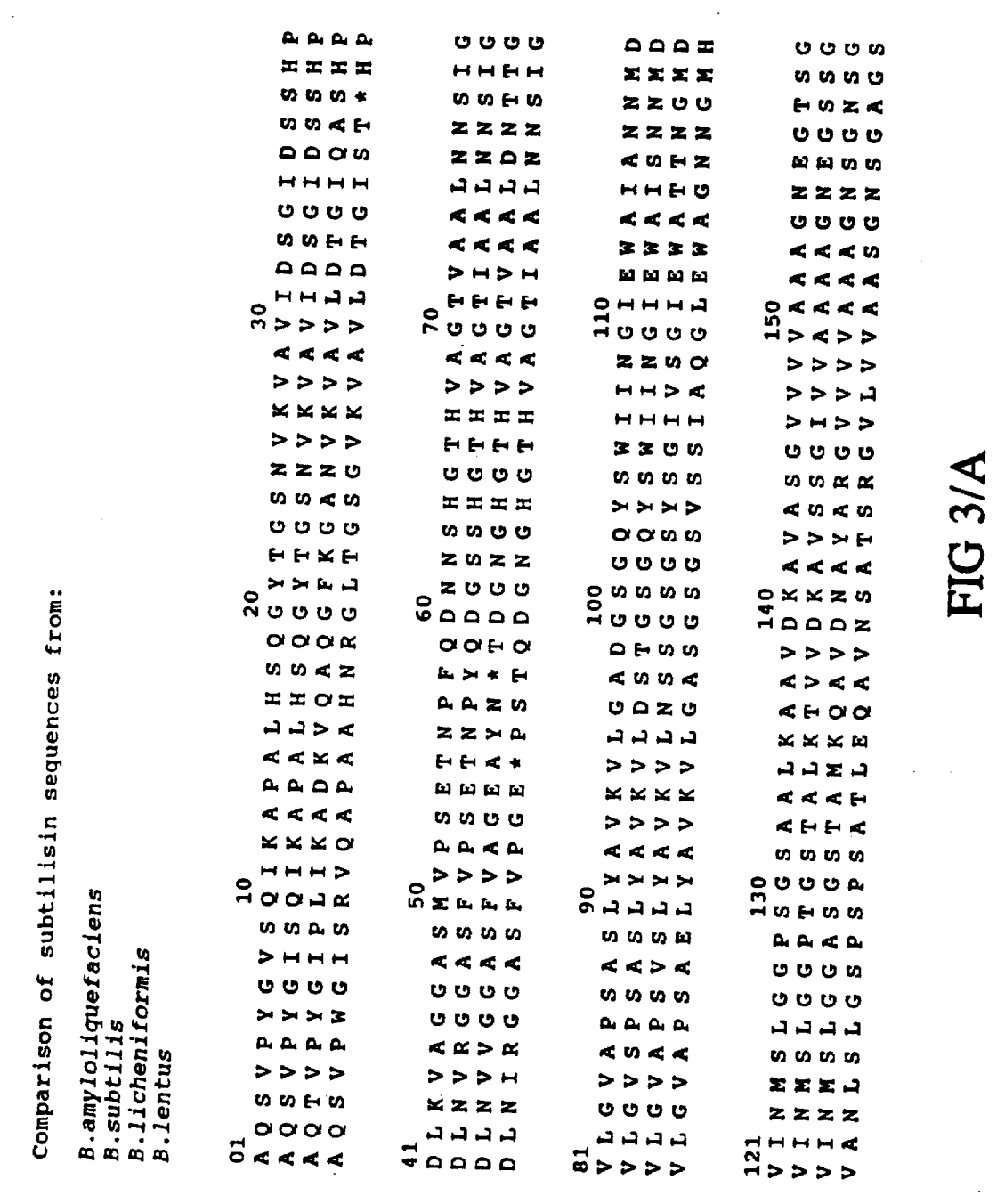

Subtilisins are bacterial or fungal carbonyl hydrolases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus, is aspartate-histidine-serine. In the chymotrypsin related proteases the relative order, however, is histidine-aspartate-serine. Thus, subtilisin herein refers to a serine protease having the catalytic triad of subtilisin related proteases. Examples include but are not limited to the subtilisins identified in FIG. 3 herein.

"Recombinant subtilisin" refers to a subtilisin in which the DNA sequence encoding the subtilisin is modified to produce a variant (or mutant) DNA sequence which encodes the substitution, deletion or insertion of one or more amino acids in the naturally-occurring subtilisin amino acid sequence. Suitable methods to produce such modification, and which may be combined with those disclosed herein, include those disclosed in U.S. Pat. Nos. 4,760,025 (Re. 34,606), 5,204,015 and 5,185,258.

"Non-human carbonyl hydrolases" and the DNA encoding them may be obtained from many procaryotic and eucaryotic organisms. Suitable examples of procaryotic organisms include gram negative organisms such as *E. coli* or *Pseudomonas* and gram positive bacteria such as *Micrococcus* or *Bacillus*. Examples of eucaryotic organisms from which carbonyl hydrolase and their genes may be obtained include yeast such as *Saccharomyces cerevisiae*, fungi such as *Aspergillus sp.* and non-human mammalian sources such as, for example, bovine sp. from which the gene encoding the carbonyl hydrolase chymosin can be obtained. As with subtilisins, a series of carbonyl hydrolases can be obtained from various related species which have amino acid sequences which are not entirely homologous between the members of that series but which nevertheless exhibit the same or similar type of biological activity. Thus, non-human carbonyl hydrolase as used herein has a functional definition which refers to carbonyl hydrolases which are associated, directly or indirectly, with procaryotic and eucaryotic sources.

A "carbonyl hydrolase variant" has an amino acid sequence which is derived from the amino acid sequence of a "precursor carbonyl hydrolase." The precursor carbonyl hydrolases (such as a subtilisin) include naturally-occurring carbonyl hydrolases (subtilisin) and recombinant carbonyl hydrolases (subtilisin). The amino acid sequence of the carbonyl hydrolase variant is "derived" from the precursor hydrolase amino acid sequence by the substitution, deletion or insertion of one or more amino acids of the precursor amino acid sequence. Such modification is of the "precursor DNA sequence" which encodes the amino acid sequence of the precursor carbonyl hydrolase (subtilisin) rather than manipulation of the precursor carbonyl hydrolase (subtilisin) enzyme per se. Suitable methods for such manipulation of the precursor DNA sequence include methods disclosed herein, as well as methods known to those skilled in the art (see, for example, EP 0 328299, WO89/06279 and the US patents and applications already referenced herein).

Specific residues corresponding to position +76 in combination with one or more of the following positions +99, +101, +103, +104, +107, +123, +27, +105, +109, +126, +128, +135, +156, +166, +195, +197, +204, +206, +210, +216, +217, +218, +222, +260, +265 and/or +274 of *Bacillus amyloliquefaciens* subtilisin are identified herein for mutation. Preferably the modified residues are selected from the following combinations: 76/99; 76/101; 76/103; 76/104; 76/107; 76/123; 76/99/101; 76/99/103; 76/99/104; 76/101/103; 76/101/104; 76/103/104; 76/104/107; 76/104/123; 76/107/123; 76/99/101/103; 76/99/101/104; 76/99/103/104; 76/101/103/104; 76/103/104/123; 76/104/107/123; 76/99/101/103/104; 76/99/103/104/123; 76/99/101/103/104/123; 76/103/104/128; 76/103/104/260; 76/103/104/265; 76/103/104/197; 76/103/104/105; 76/103/104/135; 76/103/104/126; 76/103/104/107; 76/103/104/210; 76/103/104/126/265; and/or 76/103/104/222; and most preferably are 76/99; 76/104; 76/99/104; 76/103/104; 76/104/107; 76/101/103/104; 76/99/101/103/104 and 76/101/104. These amino acid position numbers refer to those assigned to the mature *Bacillus amyloliquefaciens* subtilisin sequence presented in FIG. 1. The protease enzymes useful in the present invention, however, are not limited to the mutation of this particular subtilisin but extends to precursor carbonyl hydrolases containing amino acid residues at positions which are "equivalent" to the particular identified residues in *Bacillus amyloliquefaciens* subtilisin. Preferably, the precursor subtilisin is *Bacillus lentus* subtilisin and the substitutions, deletions or insertions are made at the equivalent amino acid residue in *B. lentus* corresponding to those listed above.

A residue (amino acid) of a precursor carbonyl hydrolase is equivalent to a residue of *Bacillus amyloliquefaciens* subtilisin if it is either homologous (i.e., corresponding in position in either primary or tertiary structure) or analogous to a specific residue or portion of that residue in *Bacillus amyloliquefaciens* subtilisin (i.e., having the same or similar functional capacity to combine, react, or interact chemically).

In order to establish homology to primary structure, the amino acid sequence of a precursor carbonyl hydrolase is directly compared to the *Bacillus amyloliquefaciens* subtilisin primary sequence and particularly to a set of residues known to be invariant in subtilisins for which sequence is known. FIG. 2 herein shows the conserved residues as between amyloliquefaciens subtilisin and *B. lentus* subtilisin. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *Bacillus amyloliquefaciens* subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained.

For example, in FIG. 3 the amino acid sequence of subtilisin from *Bacillus amyloliquefaciens, Bacillus subtilis, Bacillus licheniformis* (*carlsbergensis*) and *Bacillus lentus* are aligned to provide the maximum amount of homology between amino acid sequences. A comparison of these sequences shows that there are a number of conserved residues contained in each sequence. These conserved residues (as between BPN' and *B. lentus*) are identified in FIG. 2.

These conserved residues, thus, may be used to define the corresponding equivalent amino acid residues of *Bacillus amyloliquefaciens* subtilisin in other carbonyl hydrolases such as subtilisin from *Bacillus lentus* (PCT Publication No. W089/06279 published Jul. 13, 1989), the preferred subtilisin precursor enzyme herein, or the subtilisin referred to as PB92 (EP 0 328 299), which is highly homologous to the preferred *Bacillus lentus* subtilisin. The amino acid sequences of certain of these subtilisins are aligned in FIGS. 3A and 3B with the sequence of *Bacillus amyloliquefaciens* subtilisin to produce the maximum homology of conserved residues. As can be seen, there are a number of deletions in the sequence of *Bacillus lentus* as compared to *Bacillus amyloliquefaciens* subtilisin. Thus, for example, the equivalent amino acid for Val 165 in *Bacillus amyloliquefaciens* subtilisin in the other subtilisins is isoleucine for *B. lentus* and *B. licheniformis*.

Thus, for example, the amino acid at position +76 is asparagine (N) in both *B. amyloliquefaciens* and *B. lentus* subtilisins. In the preferred subtilisin variant useful in the invention, however, the amino acid equivalent to +76 in *Bacillus amyloliquefaciens* subtilisin is substituted with aspartate (D). A comparison of all the amino acid residues identified herein for substitution versus the preferred substitution for each such position is provided in Table II for illustrative purposes.

TABLE II

| | +76 | +99 | +101 | +103 | +104 | +107 | +123 |
|---|---|---|---|---|---|---|---|
| *B. amyloliquefaciens* (wild-type) | N | D | S | Q | Y | I | N |
| *B. lentus* (wild-type) | N | S | S | S | V | I | N |
| Most Preferred Substitution | D | D | R | A | I/Y | V | S |

Equivalent residues may also be defined by determining homology at the level of tertiary structure for a precursor carbonyl hydrolase whose tertiary structure has been determined by x-ray crystallography. Equivalent residues are defined as those for which the atomic coordinates of two or more of the main chain atoms of a particular amino acid residue of the precursor carbonyl hydrolase and *Bacillus amyloliquefadens* subtilisin (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the carbonyl hydrolase in question to the *Bacillus amyloliquefaciens* subtilisin. The best model is the crystallographic model giving the lowest R factor for experimental diffraction data at the highest resolution available.

$$R\ \text{factor} = \frac{\Sigma_h |Fo(h)| - |Fc(h)|}{\Sigma_h |Fo(h)|}$$

Equivalent residues which are functionally analogous to a specific residue of *Bacillus amyloliquefaciens* subtilisin are defined as those amino acids of the precursor carbonyl hydrolases which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor carbonyl hydrolase (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Bacillus amyloliquefaciens* subtilisin. The coordinates of the three dimensional structure of *Bacillus amyloliquefaciens* subtilisin are set forth in EPO Publication No. 0 251 446 (equivalent to U.S. patent application Ser. No. 081212,291, the disclosure of which is incorporated herein by reference) and can be used as outlined above to determine equivalent residues on the level of tertiary structure.

Some of the residues identified for substitution, insertion or deletion are conserved residues whereas others are not. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. The carbonyl hydrolase variants useful in the present invention include the mature forms of carbonyl hydrolase variants, as well as the pro- and prepro-forms of such hydrolase variants. The prepro-forms are the preferred construction since this facilitates the expression, secretion and maturation of the carbonyl hydrolase variants.

"Prosequence" refers to a sequence of amino acids bound to the N-terminal portion of the mature form of a carbonyl hydrolase which when removed results in the appearance of the "mature" form of the carbonyl hydrolase. Many proteolytic enzymes are found in nature as translational proenzyme products and, in the absence of post-translational processing, are expressed in this fashion. A preferred prosequence for producing carbonyl hydrolase variants, specifically subtilisin variants, is the putative prosequence of *Bacillus amyloliquefaciens* subtilisin, although other subtilisin prosequences may be used. In the Examples, the putative prosequence from the subtilisin from *Bacillus lentus* (ATCC 21536) is used.

A "signal sequence" or "presequence" refers to any sequence of amino acids bound to the N-terminal portion of a carbonyl hydrolase or to the N-terminal portion of a prohydrolase which may participate in the secretion of the mature or pro forms of the hydrolase. This definition of signal sequence is a functional one, meant to include all those amino acid sequences encoded by the N-terminal portion of the subtilisin gene or other secretable carbonyl hydrolases which participate in the effectuation of the secretion of subtilisin or other carbonyl hydrolases under native conditions. The protease enzymes useful for the present invention utilize such sequences to effect the secretion of the carbonyl hydrolase variants as described herein. A preferred signal sequence used in the Examples comprises the first seven amino acid residues of the signal sequence from *Bacillus subtilis* subtilisin fused to the remainder of the signal sequence of the subtilisin from *Bacillus lentus* (ATCC 21536).

A "prepro" form of a carbonyl hydrolase variant consists of the mature form of the hydrolase having a prosequence operably linked to the amino terminus of the hydrolase and a "pre" or "signal" sequence operably linked to the amino terminus of the prosequence.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, included herein are such other forms of expression vectors which serve equivalent functions and which are, or become, known in the art.

The "host cells" used in the present invention generally are procaryotic or eucaryotic hosts which preferably have been manipulated by the methods disclosed in U.S. Pat. No. 4,760,025 (Re. 34,606) to render them incapable of secreting enzymatically active endoprotease. A preferred host cell for expressing subtilisin is the Bacillus strain BG2036 which is deficient in enzymatically active neutral protease and alkaline protease (subtilisin). The construction of strain BG2036 is described in detail in U.S. Pat. No. 5,264,366. Other host cells for expressing subtilisin include *Bacillus subtilis* I168 (also described in U.S. Pat. Nos. 4,760,025 (Re. 34,606) and 5,264,366, the disclosure of which are incorporated herein by reference), as well as any suitable Bacillus strain such as *B. licheniformis, B. lentus*, etc.

Host cells are transformed or transfected with vectors constructed using recombinant DNA techniques. Such transformed host cells are capable of either replicating vectors encoding the carbonyl hydrolase variants or expressing the desired carbonyl hydrolase variant. In the case of vectors which encode the pre- or prepro-form of the carbonyl hydrolase variant, such variants, when expressed, are typically secreted from the host cell into the host cell medium.

"Operably linked," when describing the relationship between two DNA regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor carbonyl hydrolase may be obtained in accord with the general methods known to those skilled in the art. The methods generally comprise synthesizing labeled probes having putative sequences encoding regions of the hydrolase of interest, preparing genomic libraries from organisms expressing the hydrolase, and screening the libraries for the gene of interest by hybridization to the probes. Positively hybridizing clones are then mapped and sequenced. The *B. lentus* gene used in the Examples is cloned as described in Example 1 of U.S. Pat. No. 5,185,258, the disclosure of which is incorporated herein. The BPN' gene used in the Examples is cloned as described in Example 1 in U.S. Pat. No. Re. 34,606, the disclosure of which is incorporated herein.

The cloned carbonyl hydrolase is then used to transform a host cell in order to express the hydrolase. The hydrolase gene is then ligated into a high copy number plasmid. This plasmid replicates in hosts in the sense that it contains the well-known elements necessary for plasmid replication: a promoter operably linked to the gene in question (which may be supplied as the gene's own homologous promotor if it is recognized, i.e., transcribed, by the host), a transcription termination and polyadenylation region (necessary for stability of the MRNA transcribed by the host from the hydrolase gene in certain eucaryotic host cells) which is exogenous or is supplied by the endogenous terminator region of the hydrolase gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the hydrolase gene into host genome. This is facilitated by procaryotic and eucaryotic organisms which are particularly susceptible to homologous recombination.

The genes used in the present examples are a natural *B. lentus* gene and a natural *B. amyloliquefaciens* gene. Alternatively, a synthetic gene encoding a naturally-occurring or mutant precursor carbonyl hydrolase (subtilisin) may be produced. In such an approach, the DNA and/or amino acid sequence of the precursor hydrolase (subtilisin) is determined. Multiple, overlapping synthetic single-stranded DNA fragments are thereafter synthesized, which upon hybridization and ligation produce a synthetic DNA encoding the precursor hydrolase. An example of synthetic gene construction is set forth in Example 3 of U.S. Pat. No. 5,204,015, the disclosure of which is incorporated herein by reference.

Once the naturally-occurring or synthetic precursor carbonyl hydrolase gene has been cloned, a number of modifications are undertaken to enhance the use of the gene beyond synthesis of the naturally-occurring precursor carbonyl hydrolase. Such modifications include the production of recombinant carbonyl hydrolases as disclosed in U.S. Pat. Nos. 4,760,025 (Re. 34,606) and EPO Publication No. 0 251 446 and the production of carbonyl hydrolase variants described herein.

The following cassette mutagenesis method may be used to facilitate the construction and identification of the carbonyl hydrolase variants useful in the present invention, although other methods including site-directed mutagenesis may be used. First, the naturally-occurring gene encoding the hydrolase is obtained and sequenced in whole or in part. Then the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which when expressed will encode various mutants. Such restriction sites are preferably unique sites within the hydrolase gene so as to facilitate the replacement of the gene segment. However, any convenient restriction site which is not overly redundant in the hydrolase gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, proteolytic activity is defined as the rate of hydrolysis of peptide bonds per milligram of active enzyme. Many well known procedures exist for measuring proteolytic activity (K. M. Kalisz, "Microbial Proteinases," *Advances in Biochemical Engineering/Biotechnology*, A. Fiechter ed., 1988). In addition to or as an alternative to modified proteolytic activity, the variant enzymes of the present invention may have other modified properties such as $K_m$, $K_{cat}$, $K_{cat}/K_m$ ratio and/or modified substrate specificity and/or modified pH activity profile. These enzymes can be tailored for the particular substrate which is anticipated to be present, for example, for hydrolytic processes such as laundry uses.

One objective can be to secure a variant carbonyl hydrolase having altered proteolytic activity as compared to the precursor carbonyl hydrolase, since increasing such activity (numerically larger) enables the use of the enzyme to more efficiently act on a target substrate. Also of interest are variant enzymes having altered thermal stability and/or altered substrate specificity as compared to the precursor. Preferably the carbonyl hydrolase to be mutated is a subtilisin. Specific amino acids useful to obtain such results in subtilisin-type carbonyl hydrolases at residues equivalent to +76, +99, +101, +103, +104, +107, +123, +27, +105, +109, +126, +128, +135, +156, +166, +195, +197, +204, +206, +210, +216, +217, +218, +222, +260, +265 and/or +274 or any combination thereof in *Bacillus amyloliquefaciens* subtilisin are presented in the Examples. In some instances, lower proteolytic activity may be desirable. Conversely, in some instances it may be desirable to increase the proteolytic activity of the variant enzyme versus its precursor. Additionally, increases or decreases (alteration) of the stability of the variant, whether alkaline or thermal stability, may be desirable. Increases or decreases in $K_{cat}$, $K_m$ or $K_{cat}/K_m$ are specific to the substrate used to determine these kinetic parameters.

Also, it has been determined that residues equivalent to +76 in combination with a number of other modifications in subtilisin are important in modulating overall stability and/or proteolytic activity of the enzyme. Thus, as set forth in the Examples, the Asparagine (N) in Bacillus lentus subtilisin at equivalent position +76 can be substituted with Aspartate (D) in the preferred protease enzymes in combination with modification of one or more of the following amino acid residues +99, +101, +103, +104, +107, +123, +27, +105, +109, +126, +128, +135, +156, +166, +195, +197, +204, +206, +210, +216, +217, +218, +222, +260, +265 and/or +274 to produce enhanced stability and/or enhanced activity of the resulting mutant enzyme.

The most preferred protease enzymes useful in this invention are set forth in the Examples. These include the following specific combinations of substituted residues: N76D/S99D; N76D/V104I1; N76D/S99D/V104I; N76D/S103A/V104I; N76V/N104I/I107V; N76DV/104Y/I107V and N76D/S101R/S103A/VN104I. These substitutions am preferably made in *Bacillus lentus* (recombinant or native-type) subtilisin, although the substitutions may be made in any Bacillus subtilisin.

Based on the results obtained with this and other variant subtilisins, it is apparent that residues in carbonyl hydrolases (preferably subtilisin) equivalent to positions +76, +99, +101, +103, +104, +107, +123, +27, +105, +109, +126, +128, +135, +156, +166, +195, +197, +204, +206, +210, +216, +217, +218, +222, +260, +265 and/or +274 in *Bacillus amyloliquefaciens* are important to the proteolytic activity, performance and/or stability of these enzymes and the cleaning or wash performance of such variant enzymes.

The following is presented by way of example for manufacturing protease enzymes useful in the present invention compositions.

Protease Manufacture Example

Construction for the Expression of GG36 Gene in *B. subtilis*

The cloning and the construction for expression of the subtilisin gene from *B. lentus* is performed essentially the same as that described in U.S. Pat. No. 5,185,258. The plasmid GGA274 (described in FIG. 4 herein) is further modified in the following manner, as shown in FIG. 5. The PstI site that is introduced during the construction of the GGA274 plasmid is removed by the oligonucleotide directed mutagenesis described below, with an oligonucleotide having the following sequence: 5' GAAGCTGCA ACTCGTTAAA 3'(Seq. ID No. 1 ). The underlined "A" residue eliminates the recognition sequence of restriction enzyme PstI and changes the corresponding amino acid residue from alanine to threonine at position 274. Threonine at position 274 is the wild-type residue originally found in the cloned *B. lentus* subtilisin gene sequences. The DNA segment encoding subtilisin is excised from the plasmid GGA274 or its derivatives (GGT274 shown in FIG. 5) by EcoRI and BamHI digest. The DNA fragment is subcloned back into Bacteriophage M13-based vectors, such as MP19, for mutagenesis. After mutagenesis, the EcoRI and HindIII digest, followed by cloning, are performed to move the mutated subtilisin gene back into an expression plasmid like GGA274 for the expression and the recovery of mutated subtilisin proteins.

Oligonucleotide-Directed Mutagenesis

Oligonucleotide-directed mutagenesis is performed as described in Zoller, M. et al. (1983), *Methods Enzymol.*, 100:468–500. As an example, a synthetic oligonucleotide of the sequence 5' GCTGCTCTAGACAATTCG 3' (Seq. ID No.2) is used to change the amino acid residue at position 76 from asparagine (N) to aspartic acid (D), or N76D. The underlined "G" and "C" residues denote changes from the wild-type gene sequence. The CA keeps the leucine at position +75 and changes the amino acid sequence to introduce an XbaI recognition site of the XbaI restriction enzyme (TCTAGA), while the change at GAC changes asparagine at +76 to aspartate.

For mutagenesis at positions 99, 101, 103 and 104, different oligonucleotides can be used depending on the combination of mutations desired. For example, an oligonucleotide of the sequence 5' GTATTAGGGGCG GACGGTCGAGGCGCCATCAGCTCGATT 3' (Seq. ID No.3) is used to simultaneously make the following changes: S99D; S101 R; S103A and V104I in a single subtilisin molecule. Similarly, oligonucleotides of the sequence 5' TCAGGTTCGGTCTCGAGC GTTGCCCAAGGATTG 3' (Seq. ID No.4) and 5' CACGT-TGCTAGCTTGAGTTTAG 3' (Seq. ID No.5) are utilized to generate I107V and N123S, respectively. Again, the underlined residues denote changes from wild-type sequences which produce desired changes either in amino acid sequences or restriction enzyme recognition sequences.

Proteolytic Activity of Subtilisin Variants

Following the methods of Oligonucleotide-Directed Mutagenesis hereinbefore, the variants listed in Table III are made. Proteolytic activity of each of these subtilisin variants is shown in Table III. The kinetic parameters $k_{cat}$, $K_M$, and $k_{cat}/K_M$ are measured for hydrolysis of the synthetic peptide substrate succinyl-L-Ala-L-Ala-L-Pro-L-Phe-p-nitroanilide using the method described in P. Bonneau et al. (1991) *J. Am. Chem. Soc.*, Vol. 113, No. 3, p. 1030. Briefly, a small aliquot of subtilisin variant stock solution is added to a 1 cm cuvette containing substrate dissolved in 0.1M Tris-HCL buffer, pH 8.6, and thermostated at 25° C. The reaction progress is followed spectrophotometrically by monitoring the absorbance of the reaction product p-nitroaniline at 410 nm. Kinetic parameters are obtained by using a non-linear regression algorithm to fit the reaction velocity and product concentration for each reaction to the Michaelis-Menten equation.

TABLE III

Kinetic Parameters $k_{cat}$, $K_M$ and $k_{cat}/K_M$
Measured for *Bacillus lentus* Subtilisin and Variants

| Protease # | Enzyme Variants | $k_{cat}$ (s$^{-1}$) | $K_M$ (M) | $k_{cat}/K_M$ (s$^{-1}$M$^{-1}$) |
|---|---|---|---|---|
| — | *B. lentus* Subtilisin | 170 | 0.00078 | 2.18 × 10$^5$ |
| — | N76D | 219 | 0.0008 | 2.74 × 10$^5$ |
| 1 | N76D/S99D | 88 | 0.00061 | 1.44 × 10$^5$ |
| 2 | N76D/S101R | 371 | 0.0013 | 2.85 × 10$^5$ |
| 3 | N76D/S103A | 400 | 0.0014 | 2.86 × 10$^5$ |
| 4 | N76D/V104I | 459 | 0.0011 | 4.17 × 10$^5$ |
| 5 | N76D/I107V | 219 | 0.0011 | 1.99 × 10$^5$ |
| 6 | N76D/N123S | 115 | 0.0018 | 6.40 × 10$^4$ |
| 7 | N76D/S99D/S101R | 146 | 0.00038 | 3.84 × 10$^5$ |
| 8 | N76D/S99D/S103A | 157 | 0.0012 | 1.31 × 10$^5$ |
| 9 | N76D/S99D/V104I | 247 | 0.00097 | 2.55 × 10$^5$ |
| 10 | N76D/S101R/S103A | 405 | 0.00069 | 5.90 × 10$^5$ |
| 11 | N76D/S101R/V104I | 540 | 0.00049 | 1.10 × 10$^6$ |
| 12 | N76D/S103A/V104I | 832 | 0.0016 | 5.20 × 10$^5$ |
| 13 | N76D/V104I/I107V | 497 | 0.00045 | 1.10 × 10$^6$ |
| 14 | N76D/V104Y/I107V | 330 | 0.00017 | 1.90 × 10$^6$ |
| 15 | N76D/V104I/N123S | 251 | 0.0026 | 9.65 × 10$^4$ |
| 16 | N76D/I107V/N123S | 147 | 0.0035 | 4.20 × 10$^4$ |
| 17 | N76D/S99D/S101R/S103A | 242 | 0.00074 | 3.27 × 10$^5$ |
| 18 | N76D/S99D/S101R/V104I | 403 | 0.00072 | 5.60 × 10$^5$ |
| 19 | N76D/S99D/S103A/V104I | 420 | 0.0016 | 2.62 × 10$^5$ |
| 20 | N76D/S101R/S103A/V104I | 731 | 0.00065 | 1.12 × 10$^6$ |
| 21 | N76D/S103A/V104I/N123S | 321 | 0.0026 | 1.23 × 10$^5$ |
| 22 | N76D/V104I/I107V/N123S | 231 | 0.003 | 7.70 × 10$^4$ |
| 23 | N76D/S99D/S101R/S103A/V104I | 624 | 0.00098 | 6.37 × 10$^5$ |
| 24 | N76D/S99D/S103A/V104I/N123S | 194 | 0.0043 | 4.51 × 10$^4$ |
| 25 | N76D/S99D/S101R/S103A/V104I/N123S | 311 | 0.0023 | 1.35 × 10$^5$ |

The results listed in Table III indicate that all of the subtilisin variants tested retain proteolytic activity. Further, detailed analysis of the data reveal that proteolytic activity is significantly altered for *Bacillus lentus* subtilisin by the various combinations of substitutions at amino acid residues equivalent to positions 76, 99, 101, 103, 104, 107 and 123 in *Bacillus amyloliquefaciens*.

Thermal Stability of Subtilisin Variants

A comparison of thermal stability observed for *Bacillus lentus* subtilisin and the variants of the present invention made by the process of Oligonucleotide-Directed Mutagenesis hereinbefore is shown in Table IV. Purified enzyme, 15 ug/ml in 0.1M glycine 0.01% Tween-80 pH 10.0, with or without 50 mM CaCl$_2$, is aliquotted into small tubes and incubated at 10° C. for 5 minutes, 10° C. to 60° C. over 1 minute, and 60° C. for 20 minutes. Tubes are then placed on ice for 10 minutes. Aliquots from the tubes are assayed for enzyme activity by addition to 1 cm cuvettes containing 1.2 mM of the synthetic peptide substrate succinyl-L-ala-L-Ala-L-Pro-L-Phe-p-nitroanilide dissolved in 0.1M tris-HCL buffer, pH 8.6, thermostatted at 25° C. The initial linear reaction velocity is followed spectrophotometrically by monitoring the absorbance of the reaction product p-nitroaniline at 410 nm as a function of time. Data are presented as percent activity prior to heating. The results listed in Table IV indicate that a vast majority of variants exhibit thermal stability comparable to Bacillus lentus subtilisin (24 out of 26) in the test condition with 50 mm CaCl$_2$ added. In the test condition without 50 mM CaCl$_2$ added, a vast majority of variants (19 out of 26) are significantly more stable than *Bacillus lentus* subtilisin. Further, the variants N76D/S99D, N76D/V104I, N76D/S99D/V104I, N76D/S103A/V104I, N76D/V104I/VI107V, N76D/V104Y/I107V and N76D/S101R/S103A/V104I are significantly more stable than the single substitution variant N76D in the test condition without 50mM CaCl$_2$ added.

TABLE IV

Thermal Stability Measured for *Bacillus lentus* Subtilisin and Variants At pH 10, 60° C., +/− 50 mM CaCl$_2$ Added

| Enzyme | % Initial Activity Remaining | |
|---|---|---|
| | −CaCl$_2$ | +CaCl$_2$ |
| *B. lentus* Subtilisin | 2 | 96 |
| N76D | 34 | 97 |
| N76D/S99D | 49 | 98 |
| N76D/S101R | 0 | 82 |
| N76D/S103A | 26 | 92 |
| N76D/V104I | 58 | 98 |
| N76D/I107V | 32 | 96 |
| N76D/N123S | 0 | 97 |
| N76D/S99D/S101R | 30 | 100 |
| N76D/S99D/S103A | 36 | 100 |
| N76D/S99D/V104I | 48 | 97 |
| N76D/S101R/S103A | 26 | 100 |
| N76D/S101R/V104I | 38 | 100 |
| N76D/S103A/V104I | 58 | 100 |
| N76D/V104I/I107V | 60 | 97 |
| N76D/V104Y/I107V | 48 | 74 |
| N76D/V104I/N123S | 0 | 98 |
| N76D/I107V/N123S | 16 | 100 |
| N76D/S99D/S101R/S103A | 38 | 100 |
| N76D/S99D/S101R/V104I | 33 | 100 |
| N76D/S99D/S103A/V104I | 38 | 98 |
| N76D/S101R/S103A/V104I | 40 | 99 |
| N76D/S103A/V104I/N123S | 1 | 98 |
| N76D/V104I/I107V/N123S | 3 | 99 |
| N76D/S99D/S101R/S103A/V104I | 36 | 99 |
| N76D/S99D/S103A/V104I/N123S | 2 | 95 |
| N76D/S99D/S101R/S103A/V104I/N123S | 0 | 100 |

Oligonucleotide-Directed Mutagenesis with Single-Stranded DNA Template Generated from Phagemid

A. Construction of *B. lentus* Variants

The mutagenesis protocol is essentially the same as described above in Oligonucleotide-Directed Mutagenesis. The single-stranded DNA template is generated by phagemid method. To construct the phagemid vector for generating the single-stranded DNA template we first construct the vector pBCDAICAT. The flow chart of vector construction is outlined in FIG. 8. First, the ClaI to ClaI fragment encoding the CAT gene from pC194 plasmid (Horinouchi, S. and Weisblum, B., *J. Bacteriol.*, 150:8–15, 1982) is cloned into the AccI site of polylinker region of pUC19 (New England BioLabs, Beverly, Mass.) to make plasmid pUCCHL and the EcoRI-DraI 0.6 KB fragment from the 5' end of the GG36DAI encoding DNA is cloned into the EcoRI and EcoRV sites of pBSKS plasmid (Stratagene, Inc., San Diego, Calif.) to make pBC2SK5. The single EcoRI site of the plasmid pBC2SK5 is eliminated by EcoRI digestion, followed by filling in catalyzed-by-T4 DNA polymerase, and religation to generate the plasmid pBC2SK-5R which does not have the EcoRI site. The EcoRI-DraI fragment which is cloned into pBCSK-5R is isolated as a PstI-HindIII fragment and cloned into the PstI-HindIII site of the pUCCHL (part of the polylinker of pUC19) to generate plasmid pUCCHL5R. The encoding sequence of GG36DAI gene is excised as an EcoRI-BamHI fragment and cloned into the EcoRI-BamHI sites of pUCC HL5R to make pUCCAT. The large EcoRI-HindIII fragment of pUCCAT is then cloned into the EcoRI and Hind/I/sites of BS2KS+ to generate the plasmid pBCDAICAT.

To generate single-stranded DNA, *E. coli*-containing pBCDAICAT are infected with phage R408 (obtained from Stratagene, San Diego, Calif.) following the protocol described in Russel, M., Kidd, S. and Kelley, M. R., GENE 45:333–338, 1986. Once the single-stranded DNA template is available, standard mutagenesis methods as described above in Oligonucleotide-Directed Mutogenesis are carried out. The construction of certain mutants is detailed below for illustrative purposes.

For the construction of *B. lentus* (GG36) N76D/S103A/V104I/L217H, an EcoRI-BamHI DNA fragment encoding GG36 N76D/S103A/V104I is used in the construction of pUCCAT (see FIG. 8) to generate the plasmid pBCDAICAT. After the single-stranded DNA template is made following the protocol described above, a mutagenesis primer with the following sequence

```
* *** **   x ClaI   5'TAT GCC AGC CAC AAC      (Seq. ID No. 13)
                    GGT ACT TCG ATG GCT 3'
``` is used to make the L217H. As before, the underlined residues denote the nucleotide changes that are made and the x ClaI indicates that the existing ClaI site is eliminated after the mutagenesis. The mutagenesis protocol is as described in Oligonucleotide-Directed Mutagenesis hereinbefore. After the mutagenesis, plasmid DNA is first screened for the elimination of the ClaI site and those clones missing the ClaI site are subjected to DNA sequence analysis to verify the DNA sequence which made the L to H change at the 217th amino acid residue.

B. Construction of BPN' Variants and their Expression in *B. subtilis*

The construction of *B. amyloliquefaciens* (BPN') N76D/Q103A/Y104I/Y217L is done in a similar fashion except in two consecutive steps. N76D is first introduced into BPN' Y217L to make BPN' N76D/Y217L and a second mutagenesis is done to convert BPN' N76D/Y217L to BPN' N76D/Q103A/Y104I/Y217L. To generate the single-stranded DNA template for the first mutagenesis, an EcoRI-BamHI fragment encoding BPN' Y217L subtilisin (derived from the Y217L plasmid described in Wells, J., et al., *PNAS*, 84, 5167, 1087) is used to construct a plasmid pUCCATFNA (see FIG. 9). The pUCCATFNA plasmid containing BPN' Y217L is used to construct the pBCFNACAT plasmid (FIG. 9). Single-stranded DNA is generated as described above. To generate BPN' N76D/Y217L, an oligonucleotide primer with the sequence

| | | | |
|---|---|---|---|
| * *  | XbaI | 5' C ACA GTT GCG GCT CTA GAT AAC TCA ATC GGT G 3' | (Seq. ID No. 14) | is used to generate the change N76D. Single-stranded DNA is then prepared from the pBCFNACAT plasmid containing the BPN' N76D/Y217L (the pBCFNACAT plasmid after N76D mutagenesis) and mutagenized with another oligonucleotide with the sequence

| | | | |
|---|---|---|---|
| * *** * | x PvuII | 5' GCT GAC GGT TCC GGC GCT ATT AGT TGG ATC ATT 3' | (Seq. ID No. 15) | to obtain BPN' N76D/Q103A/Y104I/Y217L. All steps involved in the cloning, the single-stranded DNA preparation, the mutagenesis, and the screening for mutants are carried out as described above. Expression of the BPN' gene and its variants are achieved by integrating plasmid DNA (pBCFNACAT containing the different variants' BPN' gene) directly into a protease-deficient strain of *Bacillus subtilis* as described in Re. 34,606.

Numerous variants are made as per the teachings of these Protease Manufacture Examples. Kinetics data and stability data are generated for such variants. The kinetics data are generated using the methods described hereinbefore and are provided in Table V. The stability data are generated as detailed herein. Results are shown in Table VI.

Thermal Stability Assay Procedure

Purified enzyme is buffer-exchanged into 0.1M glycine pH 10.0, 0.01% Tween-80 by applying the enzyme to a column consisting of Sephadex G-25 equilibrated with this buffer and eluting the enzyme from the column using the same buffer.

To a tube containing 0.1M glycine, 0.01% Tween-80 pH 10.0 thermostatted at 60° C., the buffer-exchanged enzyme is added to give a final enzyme concentration of 15 ug/ml.

Aliquots are removed from the 60° C. incubation at various times and immediately assayed for enzyme activity by addition to a 1 cm cuvette containing 1.2 mM of the synthetic peptide substrate Ala-L-Ala-L-PAla-L-Ala-L-Pro-L-Phe-p-nitroanilide dissolved in 0.1M tris-HCL buffer, pH 8.6, thermostatted at 25° C. The initial linear reaction velocity is followed spectrophotometrically by monitoring the absorbance of the reaction product p-nitroaniline at 410 nm as a function of time.

Half-life, which is the length of time required for 50% enzyme inactivation, is determined from the first-order plot of reaction velocity as a function of the time of incubation at 60° C.

The data are presented in Table VI as percent of the half-life determined for *Bacillus lentus* subtilisin (GG36) under identical conditions.

TABLE V

| Enzyme | kcat (s$^{-1}$) | KM (mM) | kcat/KM (s$^{-1}$M$^{-1}$) |
|---|---|---|---|
| *B. lentus* subtilisin | 170 | 0.78 | 2.20E+05 |
| N76D/S103G/V104I* | 380 | 1.4 | 2.70E+05 |
| N76D/S103A/V104F | 730 | 0.33 | 2.20E+06 |
| N76D/S103A/V104N | 790 | 2.8 | 2.80E+05 |
| N76D/S103A/V104S | 170 | 0.83 | 2.00E+05 |
| N76D/S103A/V104T | 370 | 1.9 | 2.00E+05 |
| N76D/S103A/V104W | 880 | 0.31 | 2.80E+06 |
| N76D/S103A/V104Y | 690 | 0.5 | 1.40E+06 |
| K27R/N76D/V104Y/N123S | 500 | 1.2 | 4.20E+05 |
| N76D/S101G/S103A/V104I* | 620 | 1.3 | 4.80E+05 |
| N76D/S103A/V104I/S105A* | 550 | 1.3 | 4.20E+05 |
| N76D/S103A/V104I/S105D* | 440 | 1.7 | 2.60E+05 |
| N76D/S103A/V104T/I107A* | 120 | 5.7 | 2.10E+04 |
| N76D/S103A/V104T/I107L* | 310 | 3.2 | 9.70E+04 |
| N76D/S103A/V104I/L126A | 90 | 2.2 | 4.10E+04 |
| N76D/S103A/V104I/L126F | 180 | 1.9 | 9.50E+04 |
| N76D/S103A/V104I/L126I | 100 | 2.4 | 4.20E+04 |
| N76D/S103A/V104I/L126V | 64 | 3.2 | 2.00E+04 |
| N76D/S103A/V104I/S128G* | 560 | 1.7 | 3.30E+05 |
| N76D/S103A/V104I/S128L* | 430 | 3.8 | 1.10E+05 |
| N76D/S103A/V104I/L135A | 140 | 0.76 | 1.80E+05 |
| N76D/S103A/V104I/L135F | 390 | 0.69 | 5.70E+05 |
| N76D/S103A/V104I/L135I | 110 | 0.73 | 1.50E+05 |
| N76D/S103A/V104I/L135V | 140 | 0.86 | 1.60E+05 |
| N76D/8103A/V104I/S156E* | 170 | 2.6 | 6.50E+04 |
| N76D/S103A/V104I/S166D* | 160 | 3.5 | 4.60E+04 |
| N76D/S103A/V104I/D197E | 510 | 1.4 | 3.60E+05 |
| N76D/S103A/V104I/N204A* | 530 | 1.1 | 4.80E+05 |
| N76D/S103A/V104I/N204G* | 580 | 1.4 | 4.10E+05 |
| N76D/S103A/V104I/N204C* | 370 | 1.3 | 2.90E+05 |
| N76D/S103A/V104I/P210I* | 500 | 1.2 | 4.20E+05 |
| N76D/S103A/V104I/L217H* | 80 | 0.63 | 1.30E+05 |
| N76D/S103A/V104I/M222A | 70 | 3.1 | 2.30E+04 |
| N76D/S103A/V104I/M222S | 80 | 3.1 | 2.60E+04 |
| N76D/S103A/V104I/T260P | 660 | 1.5 | 4.40E+05 |
| N76D/S103A/V104I/S265N | 590 | 1.3 | 4.50E+05 |
| K27R/N76D/V104Y/I107V/N123S | 220 | 1.4 | 1.60E+05 |
| K27R/N76D/V104Y/N123S/D197E | 430 | 1.1 | 3.90E+05 |
| K27R/N76D/V104Y/N123S/N204C | 400 | 1.1 | 3.60E+05 |
| K27R/N76D/V104Y/N123S/Q206L | 440 | 1.2 | 3.70E+05 |
| K27R/N76D/V104Y/N123S/S216V | 440 | 1.2 | 3.70E+05 |
| K27R/N76D/V104Y/N123S/N218S | 760 | 0.98 | 7.80E+05 |
| K27R/N76D/V104Y/N123S/T260P | 410 | 1.2 | 3.40E+05 |
| K27R/N76D/V104Y/N123S/T274A | 390 | 1 | 3.90E+05 |
| N76D/S103A/V104I/L126F/S265N | 170 | 2.1 | 8.10E+04 |
| N76D/S103A/V104I/S156E/S166D* | 40 | 6.3 | 6.40E+03 |
| K27R/N76D/V104Y/N123S/G195E/G197E | 410 | 0.98 | 4.20E+05 |
| K27R/N76D/V104Y/N123S/G195E/N218S | 540 | 0.66 | 8.20E+05 |
| K27R/N76D/V104Y/N123S/D197E/N218S | 770 | 0.79 | 9.80E+05 |
| K27R/N76D/V104Y/N123S/N204C/N218S | 610 | 0.99 | 6.20E+05 |
| K27R/N76D/V104Y/N123S/Q206L/N218S | 580 | 0.78 | 7.40E+05 |
| K27R/N76D/V104Y/N123S/N218S/T260P | 660 | 1 | 6.60E+05 |
| K27R/N76D/V104Y/N123S/N218S/T274A | 590 | 0.89 | 6.60E+05 |
| K27R/N76D/V104Y/Q109S/N123S/N218S/T274A | 520 | 1 | 5.20E+05 |
| K27R/N76D/V104Y/N123S/G195E/D197E/N218S | 460 | 0.65 | 7.10E+05 |
| *B. amyloliquefaciens* subtilisin (BPN') | 50 | 0.14 | 3.60E+05 |
| BPN'-N76D/Y217L* | 380 | 0.46 | 8.30E+05 |

*These mutants are made as per Oligonucleotide-Directed Mutagenesis with Single-Stranded DNA Template Generated from Phagemid, all others made as per Oligonucleotide-Directed Mutagenesis, hereinbefore.

TABLE VI

| Enzyme | Thermal Stability (% half-life of native enzyme) |
|---|---|
| *B. lentus* subtilisin | 100 |
| N76D | 590 |
| N76D/S99D | 840 |
| N76D/S103A | 390 |
| N76D/V104I | 660 |

TABLE VI-continued

| Enzyme | Thermal Stability (% half-life of native enzyme) |
|---|---|
| N76D/I107V | 710 |
| N76D/N123S | 70 |
| N76D/S99D/S101R | 610 |
| N76D/S99D/S103A | 590 |
| N76D/S99D/V104I | 910 |
| N76D/S101R/S103A | 930 |
| N76D/S101R/V104I | 500 |
| N76D/S103A/V104I | 460 |
| N76D/S103G/V104I* | 370 |
| N76D/S103A/V104F | 480 |
| N76D/S103A/V104N | 230 |
| N76D/S103A/V104S | 230 |
| N76D/S103A/V104T | 370 |
| N76D/S103A/V104W | 280 |
| N76D/S103A/V104Y | 400 |
| N76D/V104I/I107V | 940 |
| N76D/V104Y/I107V | 820 |
| N76D/V104I/N123S | 80 |
| N76D/I107V/N123S | 150 |
| K27R/N76D/V104Y/N123S | 100 |
| N76D/S99D/S101R/S103A | 570 |
| N76D/S99D/S101R/V104I | 1000 |
| N76D/S99D/S103A/V104I | 680 |
| N76D/S101G/S103A/V104I | 390 |
| N76D/S101R/S103A/V104I | 470 |
| N76D/S103A/V104I/S105A* | 360 |
| N76D/S103A/V104I/S105D* | 370 |
| N76D/S103A/V104T/I107A* | 270 |
| N76D/S103A/V104T/I107L* | 230 |
| N76D/S103A/V104I/N123S | 110 |
| N76D/V104I/I107V/N123S | 220 |
| N76D/S103A/V104I/L126A | 270 |
| N76D/S103A/V104I/L126F | 950 |
| N76D/S103A/V104I/L126I | 410 |
| N76D/S103A/V104I/L126V | 320 |
| N76D/S103A/V104I/S128G* | 640 |
| N76D/S103A/V104I/S128L* | 760 |
| N76D/S103A/V104I/L135A | 230 |
| N76D/S103A/V104I/L135F | 200 |
| N76D/S103A/V104I/L135I | 510 |
| N76D/S103A/V104I/L135V | 500 |
| N76D/S103A/V104I/S156E* | 120 |
| N76D/S103A/V104I/S166D* | 590 |
| N76D/S103A/V104I/D197E | 460 |
| N76D/S103A/V104I/N204A* | 230 |
| N76D/S103A/V104I/N204G* | 240 |
| N76D/S103A/V104I/N204C* | 500 |
| N76D/S103A/V104I/P210I* | 1370 |
| N76D/S103A/V104I/L217H* | 60 |
| N76D/S103A/V104I/M222A | 520 |
| N76D/S103A/V104I/M222S | 490 |
| N76D/S103A/V104I/T260P | 490 |
| N76D/S103A/V104I/S265N | 360 |
| K27R/N76D/V104Y/I107V/N123S | 210 |
| K27R/N76D/V104Y/N123S/D197E | 120 |
| K27R/N76D/N104Y/N123S/N204C | 110 |
| K27R/N76D/V104Y/N123S/Q206L | 380 |
| K27R/N76D/N104Y/N123S/S216V | 140 |
| K27R/N76D/V104Y/N123S/N218S | 270 |
| K27R/N76D/V104Y/N123S/T260P | 40 |
| K27R/N76D/V104Y/N123S/T274A | 60 |
| N76D/S99D/S101R/S103A/V104I | 590 |
| N76D/S99D/S103A/V104I/N123S | 110 |
| N76D/S103A/V104I/L126F/S265N | 810 |
| N76D/S103A/V104I/S156E/S166D* | 220 |
| K27R/N76D/V104Y/N123S/G195E/G197E | 90 |
| K27R/N76D/V104Y/N123S/G195E/N218S | 250 |
| K27R/N76D/V104Y/N123S/D197E/N218S | 270 |
| K27R/N76D/V104Y/N123S/N204C/N218S | 460 |
| K27R/N76D/V104Y/N123S/Q206L/N218S | 1400 |
| K27R/N76D/V104Y/N123S/N218S/T260P | 310 |
| K27R/N76D/V104Y/N123S/N218S/T274A | 180 |
| N76D/S99D/S101R/S103A/V104I/N123S | 90 |
| K27R/N76D/N104Y/Q109S/N123S/N218S/T274 | 230 |
| K27R/N76D/V104Y/N123S/G195E/D197E/N21 | 240 |
| B. amyloliquefaciens subtilisin (BPN') | 100 |
| BPN'-N76D/Y217L* | 420 |

*These mutants are made as per Oligonucleotide-Directed Mutagenesis with Single-Stranded DNA Template Generated from Phagemid, all others made as per Oligonucleotide-Directed Mutagenesis, hereinbefore.

(3) Cleaning Composition Materials:

The cleaning compositions of the present invention also comprise, in addition to the bleaching agent and protease enzyme described hereinbefore, one or more cleaning composition materials compatible with the protease enzyme. The term "cleaning composition materials", as used herein, means any liquid, solid or gaseous material selected for the particular type of cleaning composition desired and the form of the product (e.g., liquid; granule; spray composition),- which materials are also compatible with the protease enzyme used in the composition. The specific selection of cleaning composition materials are readily made by considering the surface, item or fabric to be cleaned, and the desired form of the composition for the cleaning conditions during use (e.g., through the wash detergent use). The term "compatible", as used herein, means the cleaning composition materials do not reduce the proteolytic activity of the protease enzyme to such an extent that the protease is not effective as desired during normal use situations. Specific cleaning composition materials are exemplified in detail hereinafter.

An effective amount of one or more protease enzymes described above are included in compositions useful for cleaning a variety of surfaces in need of proteinaceous stain removal. Such cleaning compositions include detergent compositions for cleaning hard surfaces, unlimited in form (e.g., liquid and granular); detergent compositions for cleaning fabrics, unlimited in form (e.g., granular, liquid and bar formulations); dishwashing compositions (unlimited in form); oral cleaning compositions, unlimited in form (e.g., dentifrice, toothpaste and mouthwash formulations); and denture cleaning compositions, unlimited in form (e.g., liquid, tablet). As used herein, "effective amount of protease enzyme" refers to the quantity of protease enzyme described hereinbefore necessary to achieve the enzymatic activity necessary in the specific cleaning composition. Such effective amounts are readily ascertained by one of ordinary skill in the art and is based on many factors, such as the particular enzyme variant used, the cleaning application, the specific composition of the cleaning composition, and whether a liquid or dry (e.g., granular, bar) composition is required, and the like.

Preferably the cleaning compositions of the present invention comprise from about 0.0001% to about 10% of one or more protease enzymes, more preferably from about 0.001% to about 1%, more preferably still from about 0.001% to about 0.1%. Also preferably the protease enzyme is present in the compositions in an amount sufficient to provide a ratio of mg of active protease per 100 grams of composition to ppm theoretical Available $O_2$ ("Av$O_2$") from the peroxyacid in the wash liquor, referred to herein as the Enzyme to Bleach ratio (E/B ratio), ranging from about 1:1 to about 20:1. Several examples of various cleaning compositions wherein the protease enzymes may be employed are discussed in further detail below. All parts, percentages and ratios used herein are by weight unless otherwise specified.

(i) Optional Detersive Enzymes

The compositions and methods herein are effective with all manner of detersive enzymes in addition to the specified protease enzymes. Optional detersive enzymes useful in the present invention may be included for a wide variety of fabric laundering purposes, including removal of protein-based, carbohydrate-based, or triglyceride-based stains, for example, and for the prevention of fugitive dye transfer. The enzymes to be incorporated include other proteases, amylases, lipases, cellulases, and peroxidases, as well as mixtures thereof. Other types of enzymes may also be included. They may be of any suitable origin, such as vegetable, animal, bacterial, fungal and yeast origin. However, their choice is governed by several factors such as pH-activity and/or stability optima, thermostability, stability versus active detergents, builders and so on. In this respect bacterial or fungal enzymes are preferred, such as bacterial amylases and proteases, and fungal cellulases.

Enzymes are normally incorporated at levels sufficient to provide up to about 50 mg by weight, more typically about 0.01 mg to about 10 mg, of active enzyme per gram of detergent composition. Stated otherwise, an effective amount of the optional enzymes employed in the present invention will typically comprise at least about 0.001%, preferably from about 0.001% to about 5%, more preferably from about 0.001% to about 1%, most preferably from about 0.01% to about 1%, by weight of detergent composition.

Suitable examples of optional proteases are the subtilisins which are obtained from particular strains of *B.subtilis* and *B.licheniformis*. Another suitable protease is a modified bacterial serine protease enzyme obtained from *Bacillus subtilis* or *Bacillus licheniformis*, having maximum activity throughout the pH range of 8–12, developed and sold by Novo Industries A/S under the registered trade name ESPE-RASE. The preparation of this enzyme and analogous enzymes is described in British Patent Specification No. 1,243,784 of Novo. Other proteolytic enzymes that am commercially available include those sold under the tradenames ALCALASE and SAVINASE by Novo Industries A/S (Denmark) and MAXATASE by International Bio-Synthetics, Inc. (The Netherlands). Still other proteases include Protease A (see European Patent Application 130, 756, published Jan. 9, 1985) and Protease B (see European Patent Application Serial No. 87303761.8, filed Apr. 28, 1987, and European Patent Application 130,756, Bott et al, published Jan. 9, 1985), and what is called herein "Protease C", which is a triple variant of an alkaline serine protease from Bacillus in which tyrosine replaced valine at position 104, serine replaced asparagine at position 123, and alanine replaced threonine at position 274. Protease C is described in EP 90915958.4, corresponding to WO 91/06637, published May 16, 1991, which is incorporated herein by reference. Genetically modified variants, particularly of Protease C, are also included herein.

Amylases include, for example, a-amylases described in British Patent Specification No. 1,296,839 (Novo), RAPIDASE, International Bio-Synthetics, Inc. and TERMAMYL, Novo Industries.

The cellulases usable in the present invention include both bacterial or fungal cellulase. Preferably, they will have a pH optimum of between 5 and 9.5. Suitable cellulases are disclosed in U.S. Pat. No. 4,435,307, Barbesgoard et al, issued Mar. 6, 1984, which discloses fungal cellulase produced from *Humicola insolens* and Humicola strain DSM1800 or a cellulase 212-producing fungus belonging to the genus Aeromonas, and cellulase extracted from the hepatopancreas of a marine mollusk (*Dolabella Auricula Solander*). Suitable cellulases are also disclosed in GB-A-2.075.028; GB-A-2.095.275 and DE-OS-2.247.832.

Suitable lipase enzymes for detergent usage include those produced by microorganisms of the Pseudomonas group, such as *Pseudomonas stutzeri* ATCC 19.154, as disclosed in British Patent 1,372,034. See also lipases in Japanese Patent Application 53-20487, laid open to public inspection on Feb. 24, 1978. This lipase is available from Amano Pharmaceutical Co. Ltd., Nagoya, Japan, under the trade name Lipase P "Amano," hereinafter referred to as "Amano-P." Other commercial lipases include Amano-CES, lipases ex *Chromobacter viscosum*, e.g. *Chromobacter viscosum* var. *lipolyticum* NRRLB 3673, commercially available from Toyo Jozo Co., Tagata, Japan; and further *Chromobacter viscosum* lipases from U.S. Biochemical Corp., U.S.A. and Disoynth Co., The Netherlands, and lipases ex *Pseudomonas gladioli*. The LIPOLASE enzyme, derived from the fungus *Humicola lanuginosa* and expressed in *Aspergillus oryzae* as host and commercially available from Novo (see also E.P. Patent 341,947) is a preferred lipase for use herein.

Peroxidase enzymes are used in combination with oxygen sources, e.g., percarbonate, perborate, persulfate, hydrogen peroxide, etc. They are used for "solution bleaching," i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813, published Oct. 19, 1989, by O. Kirk, assigned to Novo Industries A/S.

A wide range of enzyme materials and means for their incorporation into synthetic detergent granules is also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985, both. Enzyme materials useful for liquid detergent formulations, and their incorporation into such formulations, are disclosed in U.S. Pat. No. 4,261,868, Hora et al, issued Apr. 14, 1981. Enzymes for use in detergents can be stabilized by various techniques. Enzyme stabilization techniques are disclosed and exemplified in U.S. Pat. No. 4,261,868, issued Apr. 14, 1981 to Horn, et al, U.S. Pat. No. 3,600,319, issued Aug. 17, 1971 to Gedge, et al, and European Patent Application Publication No. 0199405, Application No. 86200586.5, published Oct. 29, 1986, Venegas. Enzyme stabilization systems are also described, for example, in U.S. Pat. Nos. 4,261,868, 3,600,319, and 3,519,570.

(ii) Enzyme Stabilizers

The enzymes employed herein can be stabilized by the presence of water-soluble sources of calcium ions in the finished compositions which provide calcium ions to the enzymes. Additional stability can be provided by the presence of various other ad-disclosed stabilizers, especially borate species: see Severson, U.S. Pat. No. 4,537,706, cited above. Typical detergents, especially liquids, will comprise from about 1 to about 30, preferably from about 2 to about 20, more preferably from about 5 to about 15, and most preferably from about 8 to about 12, millimoles of calcium ion per liter of finished composition. This can vary somewhat, depending on the amount of enzyme present and its response to the calcium ions. The level of calcium ion should be selected so that there is always some minimum level available for the enzyme, after allowing for complexation with builders, fatty acids, etc., in the composition. Any water-soluble calcium salt can be used as the source of calcium ion, including, but not limited to, calcium chloride, calcium sulfate, calcium malate, calcium hydroxide, calcium formate, and calcium acetate. A small amount of calcium ion, generally from about 0.05 to about 0.4 millimoles per liter, is often also present in the composition due to calcium in the enzyme slurry and formula water. In solid detergent compositions the formulation may include a sufficient quantity of a water-soluble calcium ion source to provide such amounts in the laundry liquor. In the alternative, natural water hardness may suffice.

The compositions herein may also optionally, but preferably, contain various additional stabilizers including silicate coatings and, especially borate-type stabilizers. Typically, such stabilizers will be used at levels in the compositions from about 0.25% to about 10%, preferably from about 0.5% to about 5%, more preferably from about 0.75% to about 3%, by weight of boric acid or other borate compound capable of forming boric acid in the composition (calculated on the basis of boric acid). Boric acid is preferred, although other compounds such as boric oxide, borax and other alkali metal borates (e.g., sodium ortho-, meta- and pyroborate, and sodium pentaborate) are suitable. Substituted boric acids (e.g., phenylboronic acid, butane boronic acid, and p-bromo phenylboronic acid) can also be used in place of boric acid.

(iii) Detersive Surfactant

The amount of detersive surfactant included in the fully-formulated detergent compositions afforded by the present invention can vary from about 1% to about 99.8% depending upon the particular surfactants used and the effects desired. Preferably, the detersive surfactants comprise from about 5% to about 80% by weight of the detergent ingredients.

The detersive surfactant can be nonionic, anionic, ampholytic, zwitterionic, or cationic. Mixtures of these surfactants can also be used. Preferred detergent compositions comprise anionic detersive surfactants or mixtures of anionic surfactants with other surfactants, especially nonionic surfactants.

Nonlimiting examples of surfactants useful herein include the conventional $C_{11}$–$C_{18}$ alkyl benzene sulfonates and primary, secondary, and random alkyl sulfates, the $C_{10}$–$C_{18}$ alkyl alkoxy sulfates, the $C_{10}$–$C_{18}$ alkyl polyglycosides and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, $C_8$–$C_{24}$ sarcosinates (especially oleoyl sarcosinate) and the like. Other conventional useful surfactants are listed in standard texts.

One particular class of adjunct nonionic surfactants especially useful herein comprises the polyhydroxy fatty acid amides of the formula:

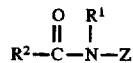

wherein: $R^1$ is H, $C_1$–$C_8$ hydrocarbyl, 2-hydroxyethyl, 2-hydroxypropyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{32}$ hydrocarbyl moiety, preferably straight chain $C_7$–$C_{19}$ alkyl or alkenyl, more preferably straight chain $C_9$–$C_{17}$ alkyl or alkenyl, most preferably straight chain $C_{11}$–$C_{19}$ alkyl or alkenyl, or mixture thereof; and Z is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —CH($CH_2OH$)—$(CHOH)_{n-1}$—$CH_2OH$, —$CH_2$—$(CHOH)_2$(CHOR')($CHOH$)—$CH_2OH$, where n is an integer from 1 to 5, inclusive, and R' is H or a cyclic mono- or polysaccharide, and alkoxylated derivatives thereof. Most preferred are glycityls wherein n is 4, particularly —$CH_2$—$(CHOH)_4CH_2OH$.

In Formula (I), $R^1$ can be, for example, N-methyl, N-ethyl, N-propyl, N-isopropyl, N-butyl, N-isobutyl, N-2-hydroxy ethyl, or N-2-hydroxy propyl. For highest sudsing, $R^1$ is preferably methyl or hydroxyalkyl. If lower sudsing is desired, $R^1$ is preferably $C_2$–$C_8$ alkyl, especially n-propyl, iso-propyl, n-butyl, iso-butyl, pentyl, hexyl and 2-ethyl hexyl.

$R^2$—CO—N< can be, for example, cocamide, stearamide, oleamide, lauramide, myristamide, capricamide, palmitamide, tallowamide, etc.

Another class of nonionic surfactants particularly useful in the present invention are condensates of ethylene oxide with a hydrophobic moiety to provide a surfactant having an average hydrophilic-lipophilic balance (HLB) in the range from 5 to 17, preferably from 6 to 14, more preferably from 7 to 12. The hydrophobic (lipophilic) moiety may be aliphatic or aromatic in nature and the length of the polyoxyethylene group which is condensed with any particular hydrophobic group can be readily adjusted to yield a water-soluble compound having the desired degree of balance between hydrophilic and hydrophobic elements.

Especially preferred nonionic surfactants of this type are the $C_9$–$C_{15}$ primary alcohol ethoxylates containing 3–8 moles of ethylene oxide per mole of alcohol, particularly the $C_{14}$–$C_{15}$ primary alcohols containing 6–8 moles of ethylene oxide per mole of alcohol, the $C_{12}$–$C_{15}$ primary alcohols containing 3–5 moles of ethylene oxide per mole of alcohol, and mixtures thereof.

(iv) Detersive Builders

Optional detergent ingredients employed in the present invention contain inorganic and/or organic detersive builders to assist in mineral hardness control. If used, these builders comprise from about 5% to about 80% by weight of the detergent compositions.

Inorganic detersive builders include, but are not limited to, the alkali metal, ammonium and alkanolammonium salts of polyphosphates (exemplified by the tri-polyphosphates, pyrophosphates, and glassy polymeric meta-phosphates), phos-phonates, phytic acid, silicates, carbonates (including bicarbonates and sesqui-carbonates), sulphates, and aluminosilicates. However, nonphosphate builders are required in some locales.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,664,839, issued May 12, 1987 to H. P. Rieck, available from Hoechst under the trademark "SKS"; SKS-6 is an especially preferred layered silicate builder.

Carbonate builders, especially a finely ground calcium carbonate with surface area greater than 10 m²/g, are preferred builders that can be used in granular compositions. The density of such alkali metal carbonate built detergents can be in the range of 450–850 g/l with the moisture content preferably below 4%.

Examples of carbonate builders are the alkaline earth and alkali metal carbonates as disclosed in German Patent Application No. 2,321,001 published on Nov. 15, 1973.

Aluminosilicate builders are especially useful in the present invention. Preferred aluminosilicates are zeolite builders which have the formula:

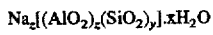

$$Na_z[(AlO_2)_z(SiO_2)_y]\cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. Methods for producing aluminosilicate ion exchange materials are disclosed in U.S. Pat. No. 3,985,669, Krummel, et al, issued Oct. 12, 1976, and U.S. Pat. No. 4,605,509, Corkill, et al, issued Aug. 12, 1986. Preferred synthetic crystalline aluminosilicate ion exchange materials useful herein are available under the designations Zeolite A, Zeolite P (B) (including those disclosed in EPO 384,070), and Zeolite X. Preferably, the aluminosilicate has a particle size of about 0.1–10 microns in diameter.

Organic detersive builders suitable for the purposes of the present invention include, but are not restricted to, a wide variety of polycarboxylate compounds, such as ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/DS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detersive builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are preferred polycarboxylate builders that can also be used in granular compositions, especially in combination with zeolite and/or layered silicate builders.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

(v) Optional Detersive Adjuncts

As a preferred embodiment, the conventional detergent ingredients employed herein can be selected from typical detergent composition components such as detersive surfactants and detersive builders. Optionally, the detergent ingredients can include one or more other detersive adjuncts or other materials for assisting or enhancing cleaning performance, treatment of the substrate to be cleaned, or to modify the aesthetics of the detergent composition. Usual detersive adjuncts of detergent compositions include the ingredients set forth in U.S. Pat. No. 3,936,537, Baskerville et al, are incorporated herein by reference. Such adjuncts which can be included in detergent compositions employed in the present invention, in their conventional art-established levels for use (generally from 0% to about 20% of the detergent ingredients, preferably from about 0.5% to about 10%), include color speckles, suds boosters, suds suppressors, antitarnish and/or anticorrosion agents, soil-suspending agents, soil release agents, dyes, fillers, optical brighteners, germicides, alkalinity sources, hydrotropes, antioxidants, perfumes, solvents, solubilizing agents, clay soil removal/anti-redeposition agents, polymeric dispersing agents, processing aids, fabric softening components (e.g., smectite clays), dye transfer inhibiting agents (e.g., polyvinyl pyrrolidone), static control agents, etc.

Bleach systems optionally, but preferably, will also comprise a chelant which not only enhances bleach stability by scavenging heavy metal ions which tend to decompose bleaches, but also assists in the removal of polyphenolic stains such as tea stains, and the like. Various chelants, including the aminophosphonates, available as DEQUEST from Monsanto, the nitrilotriacetates, the hydroxyethyl-ethylenediamine triacetates, and the like, are known for such use. Preferred biodegradable, non-phosphorus chelants include ethylene-diamine disuccinate ("EDDS"; see U.S. Pat. No. 4,704,233, Hartman and Perkins), ethylenediamine-N,N'-diglutamate (EDDG) and 2-hydroxypropylenediamine-N,N'-disuccinate (HPDDS) compounds. Such chelants can be used in their alkali or alkaline earth metal salts, typically at levels from about 0.1% to about 10% of the present compositions.

The present invention compositions are especially useful as conventional laundry detergent compositions such as those typically found in granular detergents or laundry bars. U.S. Pat. No. 3,178,370, Okenfuss, issued Apr. 13, 1965, describes laundry detergent bars and processes for making them. Philippine Patent 13,778, Anderson, issued Sep. 23, 1980, describes synthetic detergent laundry bars. Methods for making laundry detergent bars by various extrusion methods are well known in the art.

The following examples are given to further illustrate the present invention, but are not intended to be limiting thereof.

EXAMPLE 1

A granular detergent composition is prepared comprising the following ingredients.

| Component | Weight % |
| --- | --- |
| $C_{12}$ linear alkyl benzene sulfonate | 22 |
| Phosphate (as sodium tripolyphosphate) | 30 |
| Sodium carbonate | 14 |
| Sodium silicate | 3 |
| Protease 12 | 0.3 |
| Sodium percarbonate | 5 |
| Ethylenediamine disuccinate chelant (EDDS) | 0.4 |
| Sodium sulfate | 5.5 |
| Nonanoyl caprolactam | 5 |
| Filler* and water | Balance to 100% |

*Can be selected from convenient materials such as $CaCO_3$, talc, clay, silicates, and the like.

Aqueous Crutcher mixes of heat and alkali stable components of the detergent compositions are prepared and spray-dried and the other ingredients are admixed so that they contain the ingredients tabulated at the levels shown.

In this example the Protease #'s 1-11 and 13-25 recited in Table III, among others including the additional proteases useful in the present invention described in Tables V and VI, are substituted for Protease #12, with substantially similar results. Also in this example, any combination of the proteases useful in the present invention recited in Tables III, V and VI among others, are substituted for Protease #12 with substantially similar results.

EXAMPLE 2

A granular detergent composition is prepared comprising the following ingredients.

| Component | Weight % |
| --- | --- |
| Anionic alkyl sulfate | 7 |
| Nonionic surfactant | 5 |
| Zeolite (0.1–10 micron) | 10 |
| Trisodium citrate | 2 |
| SKS-6 silicate builder | 10 |
| Acrylate maleate polymer | 4 |
| Nonanoyl caprolactam | 5 |
| Sodium percarbonate* | 15 |
| Sodium carbonate | 5 |
| Ethylenediamine disuccinate chelant (EDDS) | 0.4 |
| Suds suppressor | 2 |
| Protease 12 | 0.3 |
| Lipase | 0.3 |
| Soil release agent | 0.2 |
| Minors, filler** and water | Balance to 100% |

*Average particle size of 400 to 1200 microns.
**Can be selected from convenient materials such as $CaCO_3$, talc, clay, silicates, and the like.

Aqueous crutcher mixes of heat and alkali stable components of the detergent composition are prepared and spray-dried, and the other ingredients are admixed so that they contain the ingredients tabulated at the levels shown.

In this example the Protease #'s 1-11 and 13-25 recited in Table III, among others including the additional proteases useful in the present invention described in Tables V and VI, are substituted for Protease #12, with substantially similar results. Also in this example, any combination of the proteases useful in the present invention recited in Tables III, V and VI among others, are substituted for Protease #12 with substantially similar results.

EXAMPLE 3

A detergent composition is prepared by a procedure identical to that of Example 2, with the exceptions that 15% of a 1:1:1 mixture of benzoyl caprolactam, nonanoyl caprolactam and (6-Nonanamidocaproyl)oxybenzenesulfonate is substituted for the nonanoyl caprolactam and the amount of sodium percarbonate is 30%.

In this example the Protease #'s 1-11 and 13-25 recited in Table III, among others including the additional proteases useful in the present invention described in Tables V and VI, are substituted for Protease #12, with substantially similar results. Also in this example, any combination of the proteases useful in the present invention recited in Tables III, V and VI among others, are substituted for Protease #12 with substantially similar results.

EXAMPLE 4

A detergent composition is prepared by a procedure identical to that of Example 1, with the exceptions that 20% of a 1:1 mixture of benzoyl caprolactam and (6-Nonanamidocaproyl)oxybenzenesulfonate is substituted for the nonanoyl caprolactam, the amount of sodium percarbonate is 20%, and the amount of phosphate is 0%.

In this example the Protease #'s 1-11 and 13-25 recited in Table III, among others including the additional proteases useful in the present invention described in Tables V and VI, are substituted for Protease #12, with substantially similar results. Also in this example, any combination of the proteases useful in the present invention recited in Tables III, V and VI among others, are substituted for Protease #12 with substantially similar results.

EXAMPLE 5

A detergent composition is prepared by a procedure identical to that of Example 2, with the single exception that an equivalent amount of a benzoxazin-type activator is substituted for the nonanoyl caprolactam.

In this example the Protease #'s 1-11 and 13-25 recited in Table III, among others including the additional proteases useful in the present invention described in Tables V and VI, are substituted for Protease #12, with substantially similar results. Also in this example, any combination of the proteases useful in the present invention recited in Tables III, V and VI among others, are substituted for Protease #12 with substantially similar results.

EXAMPLE 6

A detergent composition is prepared by a procedure identical to that of Example 2, with the exceptions that 10% of a 1:1 mixture of a benzoxazin-type activator and tetraacetyl ethylene diamine is substituted for the nonanoyl caprolactam and the amount of sodium percarbonate is 25%.

In this example the Protease #'s 1-11 and 13-25 recited in Table III, among others including the additional proteases useful in the present invention described in Tables V and VI, are substituted for Protease #12, with substantially similar results. Also in this example, any combination of the proteases useful in the present invention recited in Tables III, V and VI among others, are substituted for Protease #12 with substantially similar results.

EXAMPLE 7

A laundry bar suitable for hand-washing soiled fabrics is prepared by standard extrusion processes and comprises the following:

| Component | Weight % |
|---|---|
| $C_{12}$ linear alkyl benzene sulfonate | 30 |
| Phosphate (as sodium tripolyphosphate) | 7 |
| Sodium carbonate | 25 |
| Sodium pyrophosphate | 7 |
| Coconut monoethanolamide | 2 |
| Zeolite A (0.1–10 micron) | 5 |
| Carboxymethylcellulose | 0.2 |
| Polyacrylate (m.w. 1400) | 0.2 |
| (6-Nonanamidocaproyl)oxybenzenesulfonate | 5 |
| Sodium percarbonate | 5 |
| Brightener, perfume | 0.2 |
| Protease 12 | 0.3** |
| Lipase | 0.3 |
| $CaSO_4$ | 1 |
| $MgSO_4$ | 1 |
| Water | 4 |
| Filler* | Balance to 100% |

*Can be selected from convenient materials such as $CaCO_3$, talc, clay, silicates, and the like.
**Denotes mg of active enzyme per gram of composition.

The detergent laundry bars are processed in conventional soap or detergent bar making equipment as commonly used in the art.

In this example the Protease #'s 1-11 and 13-25 recited in Table III, among others including the additional proteases useful in the present invention described in Tables V and VI, are substituted for Protease #12, with substantially similar results. Also in this example, any combination of the proteases useful in the present invention recited in Tables III, V and VI among others, are substituted for Protease #12 with substantially similar results.

EXAMPLE 8

A detergent composition is prepared by a procedure identical to that of Example 7, with the single exception that an equivalent amount of benzoyl caprolactam is substituted for the (6-Nonanamidocaproyl)oxybenzenesulfonate.

In this example the Protease #'s 1-11 and 13-25 recited in Table III, among others including the additional proteases useful in the present invention described in Tables V and VI, are substituted for Protease #12, with substantially similar results. Also in this example, any combination of the proteases useful in the present invention recited in Tables III, V and VI among others, are substituted for Protease #12 with substantially similar results.

EXAMPLE 9

A detergent composition is prepared by a procedure identical to that of Example 7, with the single exception that an equivalent amount of nonanoyl caprolactam is substituted for the (6-Nonanamidocaproyl)oxybenzenesulfonate.

In this example the Protease #'s 1-11 and 13-25 recited in Table III, among others including the additional proteases useful in the present invention described in Tables V and VI, are substituted for Protease #12, with substantially similar results. Also in this example, any combination of the proteases useful in the present invention recited in Tables III, V and VI among others, are substituted for Protease #12 with substantially similar results.

EXAMPLE 10

A granular detergent composition is prepared comprising the following ingredients.

| Component | Weight % |
|---|---|
| Anionic alkyl sulfate | 7 |
| Nonionic surfactant | 5 |
| Zeolite (0.1–10 micron) | 10 |
| Trisodium citrate | 2 |
| SKS-6 silicate builder | 10 |
| Acrylate maleate polymer | 4 |
| Nonanoyl caprolactam | 5 |
| Sodium percarbonate* | 15 |
| Sodium carbonate | 5 |
| Ethylenediamine disuccinate chelant (EDDS) | 0.4 |
| Suds suppressor | 2 |
| Protease 12 | 0.5 |
| Soil release agent | 0.2 |
| Minors, filler** and water | Balance to 100% |

*Average particle size of 400 to 1200 microns.
**Can be selected from convenient materials such as $CaCO_3$, talc, clay, silicates, and the like.

Aqueous crutcher mixes of heat and alkali stable components of the detergent composition are prepared and spray-dried, and the other ingredients are admixed so that they contain the ingredients tabulated at the levels shown.

In this example the Protease #'s 1-11 and 13-25 recited in Table III, among others including the additional proteases useful in the present invention described in Tables V and VI, are substituted for Protease #12, with substantially similar results. Also in this example, any combination of the proteases useful in the present invention recited in Tables III, V and VI among others, are substituted for Protease #12 with substantially similar results.

EXAMPLE 11

A detergent composition is prepared by a procedure identical to that of Example 10, with the single exception that an equivalent amount of benzoyl caprolactam is substituted for the nonanoyl caprolactam.

In this example the Protease #'s 1-11 and 13-25 recited in Table III, among others including the additional proteases useful in the present invention described in Tables V and VI, are substituted for Protease #12, with substantially similar results. Also in this example, any combination of the proteases useful in the present invention recited in Tables III, V and VI among others, are substituted for Protease #12 with substantially similar results.

EXAMPLE 12

A detergent composition is prepared by a procedure identical to that of Example 10, with the exceptions that 15%, by weight, of (6-Nonanamido-caproyl) oxybenzenesulfonate is substituted for the nonanoyl caprolactam and the amount of sodium percarbonate is 30%.

In this example the Protease #'s 1-11 and 13-25 recited in Table III, among others including the additional proteases useful in the present invention described in Tables V and VI, are substituted for Protease #12, with substantially similar results. Also in this example, any combination of the proteases useful in the present invention recited in Tables III, V and VI among others, are substituted for Protease #12 with substantially similar results.

EXAMPLE 13

A detergent composition is prepared by a procedure identical to that of Example 10, with the exceptions that 15%, by weight, of a benzoxazin-type activator is substituted for the nonanoyl caprolactam and the amount of sodium percarbonate is 30%.

In this example the Protease #'s 1-11 and 13-25 recited in Table III, among others including the additional proteases useful in the present invention described in Tables V and VI, are substituted for Protease #12, with substantially similar results. Also in this example, any combination of the proteases useful in the present invention recited in Tables III, V and VI among others, are substituted for Protease #12 with substantially similar results.

EXAMPLE 14

Wash Performance Test

The wash performance of the variants useful in the present invention compositions is evaluated by measuring the removal of stain from EMPA 116 (blood/milk/carbon black on cotton) cloth swatches (Testfabrics, Inc., Middlesex, N.J. 07030).

Six EMPA 116 swatches, cut to 3×4½ inches with pinked edges, are placed in each pot of a Model 7243S Terg-O-Tometer (United States Testing Co., Inc., Hoboken, N.J.) containing 1000 ml of water, 15 gpg hardness ($Ca^{++}:Mg^{++}$ ::3:1::w:w), 7 g of detergent, and enzyme as appropriate. The detergent base is WFK1 detergent from wfk-Testgewebe GmbH, Adlerstrasse 42, Postfach 13 07 62, D-47759 Krefeld, Germany:

| Component | % of Final Formulation |
| --- | --- |
| Zeolite A | 25% |
| Sodiu sulfate | 25% |
| Soda Ash | 10% |
| Linear alkylbenzenesulfonate | 8.8% |
| Alcohol ethoxylate (7–8 EO) | 4.5% |
| Sodium soap | 3% |
| Sodium silicate ($SiO_2:Na_2O$::3.3:1) | 3% |

To this base detergent, the following additions are made:

| Component | % of Final Formulation |
| --- | --- |
| Sodium perborate monohydrate | 13% |
| Copolymer (Sokalan CP5) | 4% |
| TAED (Mykon ATC Green) | 3% |
| Enzyme | 0.5% |
| Brightener (Tinopal AMS-GX) | 0.2% |

Sodium perborate monohydrate is obtained from Degussa Corporation, Ridgefield-Park, N.J. 07660. Sokalan CP5 is obtained from BASF Corporation, Parsippany, N.J. 07054. Mykon ATC Green (TAED, tetraacetylethylenediamine) is obtained from Warwick International, Limited, Mostyn, Holywell, Clwyd CH8 9HE, England. Tinopal AMS GX is obtained from Ciba-Geigy Corporation, Greensboro, N.C. 27419.

Six EMPA 116 swatches are washed in detergent with enzyme for 30 min at 60° C. and are subsequently rinsed twice for 5 minutes each time in 1000 ml water. Enzymes are added at final concentrations of 0.05 to 1 ppm for standard curves, and 0.25 ppm for routine analyses. Swatches are dried and pressed, and the reflectance from the swatches is measured using the L value on the L*a*b* scale of a Minolta Chroma Meter, Model CR-200 (Minolta Corporation, Ramsey, N.J. 07446). Performance is reported as a percentage of the performance of B. lentus (GG36) protease and is calculated by dividing the amount of B. lentus (GG36) protease by the amount of variant protease that is needed to provide the same stain removal performance X 100. The data are shown in Table VII.

TABLE VII

| Enzyme | Wash Performance |
| --- | --- |
| B. lentus subtilisin | 100 |
| N76D | 310 |
| N76D/S103A | 230 |
| N76D/V104I | 130 |
| N76D/V107V | 160 |
| N76D/S99D/S101R | 370 |
| N76D/S99D/S103A | 290 |
| N76D/S101R/S103A | 130 |
| N76D/S101R/V104I | 300 |
| N76D/S103A/V104I | 320 |
| N76D/S103G/V104I | 160 |
| N76D/S103A/V104F | 210 |
| N76D/S103A/V104N | 110 |
| N76D/S103A/V104T | 170 |
| N76D/S104A/V107V | 210 |
| N76D/S99D/S101R/S103A | 220 |
| N76D/S99D/S101R/V104I | 140 |
| N76D/S101O/S103A/V104I | 170 |
| N76D/S101R/S103A/V104I | 150 |
| N76D/S103A/V104I/S104/ 105A | 170 |
| N76D/S103A/V104T/I107A | 120 |
| N76D/S103A/V104T/I107L | 110 |
| N76D/S103A/V104I/L126F | 110 |
| N76D/S103A/V104I/S128G | 280 |
| N76D/S103A/V104I/L135I | 160 |
| N76D/S103A/V104I/L135V | 160 |
| N76D/S103A/V104I/D197E | 170 |
| N76D/S103A/V104I/N204A | 160 |
| N76D/S103A/V104I/N204G | 150 |
| N76D/S103A/V104I/P210I | 470 |
| N76D/S103A/V104I/M222A | 100 |
| N76D/S103A/V104I/T260P | 280 |
| N76D/S103A/V104I/S265N | 190 |

What is claimed is:

1. A fabric cleaning composition comprising:
   (a) from about 0.0001% to about 10% protease enzyme which is an N76D/S103A/V104I subtilisin variant derived from *Bacillus lentus* subtilisin;
   (b) from about 0.5% to about 20% of a bleaching system comprising at least about 0.1% by weight of a peroxygen bleaching compound capable of yielding hydrogen peroxide in an aqueous liquor and at least 0.1% by weight of one or more bleach activators, wherein said bleach activators are members selected from the group consisting of:
   i) a bleach activator of the general formula:

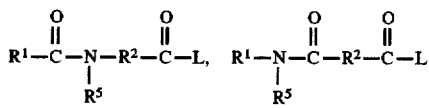

or mixtures thereof, wherein $R^1$ is an alkyl, aryl, or alkaryl group containing from about 1 to about 14 carbon atoms, $R^2$ is an alkylene, arylene or alkarylene group containing from about 1 to about 14 carbon atoms, $R^5$ is H or an alkyl, aryl, or alkaryl group containing from about 1 to about 10 carbon atoms, and L is a leaving group;
   ii) a benzoxazin-type bleach activator of the formula:

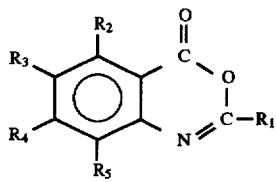

wherein $R_1$ is H, alkyl, alkaryl, aryl, arylalkyl, and wherein $R_2$, $R_3$, $R_4$, and $R_5$ may be the same or different substituents selected from H, halogen, alkyl, alkenyl, aryl, hydroxyl, alkoxyl, amino, alkylamino, —$COOR_6$, wherein $R_6$ is H or an alkyl group and carbonyl functions;
   iii) a N-acyl caprolactam bleach activator of the formula:

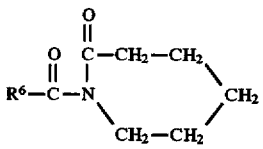

wherein $R^6$ is H or an alkyl, aryl, alkoxyaryl, or alkaryl group containing from 1 to 12 carbons; and
   iv) mixtures of i), ii) and iii);
   (c) at least about 5% surfactant;
   (d) at least about 5% builder; and
   (e) optionally, one or more cleaning composition materials compatible with the protease enzyme and bleaching system selected from the group consisting of solvents, buffers, enzymes, soil release agents, clay soil removal agents, dispersing agents, brighteners, suds suppressors, fabric softeners, suds boosters, enzyme stabilizers, dyes, perfumes, and mixtures thereof.

2. The fabric cleaning composition according to claim 1 wherein the surfactant is selected from the group consisting of alkyl benzene sulfonates, primary alkyl sulfates, secondary alkyl sulfates, alkyl alkoxy sulfates, alkyl alkoxy carboxylates, alkyl polyglycosides and their corresponding sulfated polyglycosides, alpha-sulfonated farry acid esters, alkyl and alkyl phenol alkoxylates, betaines and sulfobetaines, amine oxides, N-methyl glucamides, nonionic primary alcohol ethoxylates, nonionic primary/alcohol mixed ethoxy/propoxy, and mixtures thereof; and wherein further the builder is selected from the group consisting of zeolites, polycarboxylates, layered silicates, phosphates, and mixtures thereof.

3. A composition according to claim 2 further comprising at least about 0.001%, by weight of said cleaning composition, of at least one enzyme selected from the group consisting of proteases, amylases, lipases, cellulases, peroxidases and mixtures thereof.

4. A composition according to claim 1 wherein said bleach activator is selected from the group consisting of benzoyl caprolactam, nonanoyl caprolactam, (6-nonanamidocaproyl)oxybenzenesulfonate, and mixtures thereof.

5. A composition according to claim 1 wherein the peroxygen bleaching compound is selected from the group consisting of sodium perborate monohydrate, sodium perborate tetrahydrate, sodium pyrophosphate peroxyhydrate, urea peroxyhydrate, sodium percarbonate, sodium peroxide and mixtures thereof.

6. A composition according to claim 5 wherein the molar ratio of hydrogen peroxide to bleach activator is greater than about 1.0.

7. A composition according to claim 1 wherein $R^1$ is an alkyl group containing from about 6 to about 12 carbon atoms, $R^2$ contains from about 1 to about 8 carbon atoms, and $R^5$ is H or methyl.

8. A composition according to claim 1 wherein $R^1$ is an alkyl group containing from about 7 to about 10 carbon atoms and $R^2$ contains from about 4 to about 5 carbon atoms, and wherein L is selected from the group consisting of:

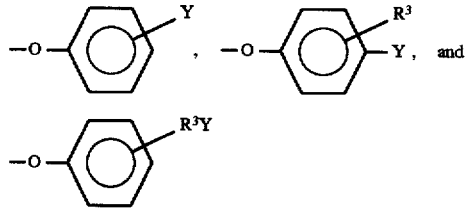

wherein $R^3$ is an alkyl chain containing from about 1 to about 8 carbon atoms, and Y is —$SO_3$—$M^+$ or —$CO_2$—$M^+$ wherein M is sodium or potassium.

9. A composition according to claim 1 comprising an N-acyl caprolactam selected from the group consisting of benzoyl caprolactam, octanoyl caprolactam, nonanoyl caprolactam, 3,5,5-trimethylhexanoyl capro-lactam, decanoyl caprolactam, undecenoyl caprolactam, and mixtures thereof.

10. A method for cleaning fabric, said method comprising contacting a fabric in need of cleaning with a wash solution containing an effective amount of a composition according to claim 1.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GAAGCTGCAA CTCGTTAAA                                                    19

( 2 ) INFORMATION FOR SEQ ID NO:2:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

GCTGCTCTAG ACAATTCG                                                     18

( 2 ) INFORMATION FOR SEQ ID NO:3:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

GTATTAGGGG CGGACGGTCG AGGCGCCATC AGCTCGATT                              39

( 2 ) INFORMATION FOR SEQ ID NO:4:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

TCAGGTTCGG TCTCGAGCGT TGCCCAAGGA TTG                                    33

( 2 ) INFORMATION FOR SEQ ID NO:5:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

```
CACGTTGCTA GCTTGAGTTT AG                                                    22
```

( 2 ) INFORMATION FOR SEQ ID NO:6:

( i ) SEQUENCE CHARACTERISTICS:
        ( A ) LENGTH: 1497 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
GGTCTACTAA AATATTATTC CATACTATAC AATTAATACA CAGAATAATC TGTCTATTGG         60
TTATTCTGCA AATGAAAAAA AGGAGAGGAT AAAGAGTGAG AGGCAAAAAA GTATGGATCA        120
GTTTGCTGTT TGCTTTAGCG TTAATCTTTA CGATGGCGTT CGGCAGCACA TCCTCTGCCC        180
AGGCGGCAGG GAAATCAAAC GGGGAAAAGA AATATATTGT CGGGTTTAAA CAGACAATGA        240
GCACGATGAG CGCCGCTAAG AAGAAAGATG TCATTTCTGA AAAAGGCGGG AAAGTGCAAA        300
AGCAATTCAA ATATGTAGAC GCAGCTTCAG TCACATTAAA CGAAAAAGCT GTAAAAGAAT        360
TGAAAAAAGA CCCGAGCGTC GCTTACGTTG AAGAAGATCA CGTAGCACAT GCGTACGCGC        420
AGTCCGTGCC TTACGGCGTA TCACAAATTA AAGCCCCTGC TCTGCACTCT CAAGGCTACA        480
CTGGATCAAA TGTTAAAGTA GCGGTTATCG ACAGCGGTAT CGATTCTTCT CATCCTGATT        540
TAAAGGTAGC AAGCGGAGCC AGCATGGTTC CTTCTGAAAC AAATCCTTTC CAAGACAACA        600
ACTCTCACGG AACTCACGTT GCCGGCACAG TTGCGGCTCT TAATAACTCA ATCGGTGTAT        660
TAGGCGTTGC GCCAAGCGCA TCACTTTACG CTGTAAAAGT TCTCGGTGCT GACGGTTCCG        720
GCCAATACAG CTGGATCATT AACGGAATCG AGTGGGCGAT CGCAAACAAT ATGGACGTTA        780
TTAACATGAG CCTCGGCGGA CCTTCTGGTT CTGCTGCTTT AAAAGCGGCA GTTGATAAAG        840
CCGTTGCATC CGGCGTCGTA GTCGTTGCGG CAGCCGGTAA CGAAGGCACT TCCGGCAGCT        900
CAAGCACAGT GGGCTACCCT GGTAAATACC CTTCTGTCAT TGCAGTAGGC GCTGTTGACA        960
GCAGCAACCA AAGAGCATCT TTCTCAAGCG TAGGACCTGA GCTTGATGTC ATGGCACCTG       1020
GCGTATCTAT CCAAAGCACG CTTCCTGGAA ACAAATACGG GGCGTACAAC GGTACGTCAA       1080
TGGCATCTCC GCACGTTGCC GGAGCGGCTG CTTTGATTCT TTCTAAGCAC CCGAACTGGA       1140
CAAACACTCA AGTCCGCAGC AGTTTAGAAA ACACCACTAC AAAACTTGGT GATTCTTTGT       1200
ACTATGGAAA AGGGCTGATC AACGTACAAG CGGCAGCTCA GTAAAACATA AAAAACCGGC       1260
CTTGGCCCCG CCGGTTTTTT ATTATTTTTC TTCCTCCGCA TGTTCAATCC GCTCCATAAT       1320
CGACGGATGG CTCCCTCTGA AAATTTAAC GAGAAACGGC GGGTTGACCC GGCTCAGTCC        1380
CGTAACGGCC AACTCCTGAA ACGTCTCAAT CGCCGCTTCC CGGTTTCCGG TCAGCTCAAT       1440
GCCATAACGG TCGGCGGCGT TTTCCTGATA CCGGGAGACG GCATTCGTAA TCGGATC         1497
```

( 2 ) INFORMATION FOR SEQ ID NO:7:

( i ) SEQUENCE CHARACTERISTICS:
        ( A ) LENGTH: 275 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Ala Gln Ser Val Pro Tyr Gly Val Ser Gln Ile Lys Ala Pro Ala Leu
 1               5                  10                  15
```

```
His  Ser  Gln  Gly  Tyr  Thr  Gly  Ser  Asn  Val  Lys  Val  Ala  Val  Ile  Asp
               20                      25                     30

Ser  Gly  Ile  Asp  Ser  Ser  His  Pro  Asp  Leu  Lys  Val  Ala  Gly  Gly  Ala
          35                      40                     45

Ser  Met  Val  Pro  Ser  Glu  Thr  Asn  Pro  Phe  Gln  Asp  Asn  Asn  Ser  His
     50                       55                      60

Gly  Thr  His  Val  Ala  Gly  Thr  Val  Ala  Ala  Leu  Asn  Asn  Ser  Ile  Gly
65                       70                      75                           80

Val  Leu  Gly  Val  Ala  Pro  Ser  Ala  Ser  Leu  Tyr  Ala  Val  Lys  Val  Leu
                    85                      90                     95

Gly  Ala  Asp  Gly  Ser  Gly  Gln  Tyr  Ser  Trp  Ile  Ile  Asn  Gly  Ile  Glu
               100                     105                     110

Trp  Ala  Ile  Ala  Asn  Asn  Met  Asp  Val  Ile  Asn  Met  Ser  Leu  Gly  Gly
          115                     120                     125

Pro  Ser  Gly  Ser  Ala  Ala  Leu  Lys  Ala  Ala  Val  Asp  Lys  Ala  Val  Ala
     130                     135                     140

Ser  Gly  Val  Val  Val  Ala  Ala  Ala  Gly  Asn  Glu  Gly  Thr  Ser  Gly
145                      150                     155                          160

Ser  Ser  Ser  Thr  Val  Gly  Tyr  Pro  Gly  Lys  Tyr  Pro  Ser  Val  Ile  Ala
               165                     170                     175

Val  Gly  Ala  Val  Asp  Ser  Ser  Asn  Gln  Arg  Ala  Ser  Phe  Ser  Ser  Val
               180                     185                     190

Gly  Pro  Glu  Leu  Asp  Val  Met  Ala  Pro  Gly  Val  Ser  Ile  Gln  Ser  Thr
          195                     200                     205

Leu  Pro  Gly  Asn  Lys  Tyr  Gly  Ala  Tyr  Asn  Gly  Thr  Ser  Met  Ala  Ser
     210                     215                     220

Pro  His  Val  Ala  Gly  Ala  Ala  Leu  Ile  Leu  Ser  Lys  His  Pro  Asn
225                      230                     235                          240

Trp  Thr  Asn  Thr  Gln  Val  Arg  Ser  Ser  Leu  Glu  Asn  Thr  Thr  Thr  Lys
               245                     250                     255

Leu  Gly  Asp  Ser  Phe  Tyr  Tyr  Gly  Lys  Gly  Leu  Ile  Asn  Val  Gln  Ala
               260                     265                     270

Ala  Ala  Gln
          275
```

( 2 ) INFORMATION FOR SEQ ID NO:8:

( i ) SEQUENCE CHARACTERISTICS:
        ( A ) LENGTH: 275 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Ala  Gln  Ser  Val  Pro  Tyr  Gly  Ile  Ser  Gln  Ile  Lys  Ala  Pro  Ala  Leu
1                   5                       10                     15

His  Ser  Gln  Gly  Tyr  Thr  Gly  Ser  Asn  Val  Lys  Val  Ala  Val  Ile  Asp
               20                      25                     30

Ser  Gly  Ile  Asp  Ser  Ser  His  Pro  Asp  Leu  Asn  Val  Arg  Gly  Gly  Ala
          35                      40                     45

Ser  Phe  Val  Pro  Ser  Glu  Thr  Asn  Pro  Tyr  Gln  Asp  Gly  Ser  Ser  His
     50                       55                      60

Gly  Thr  His  Val  Ala  Gly  Thr  Ile  Ala  Ala  Leu  Asn  Asn  Ser  Ile  Gly
65                       70                      75                           80
```

```
Val  Leu  Gly  Val  Ser  Pro  Ser  Ala  Ser  Leu  Tyr  Ala  Val  Lys  Val  Leu
               85                  90                       95

Asp  Ser  Thr  Gly  Ser  Gly  Gln  Tyr  Ser  Trp  Ile  Ile  Asn  Gly  Ile  Glu
               100                 105                      110

Trp  Ala  Ile  Ser  Asn  Asn  Met  Asp  Val  Ile  Asn  Met  Ser  Leu  Gly  Gly
               115                 120                      125

Pro  Thr  Gly  Ser  Thr  Ala  Leu  Lys  Thr  Val  Val  Asp  Lys  Ala  Val  Ser
               130                 135                      140

Ser  Gly  Ile  Val  Val  Ala  Ala  Ala  Gly  Asn  Glu  Gly  Ser  Ser  Gly
145                           150                 155                      160

Ser  Thr  Ser  Thr  Val  Gly  Tyr  Pro  Ala  Lys  Tyr  Pro  Ser  Thr  Ile  Ala
               165                 170                      175

Val  Gly  Ala  Val  Asn  Ser  Ser  Asn  Gln  Arg  Ala  Ser  Phe  Ser  Ser  Ala
               180                 185                      190

Gly  Ser  Glu  Leu  Asp  Val  Met  Ala  Pro  Gly  Val  Ser  Ile  Gln  Ser  Thr
               195                 200                      205

Leu  Pro  Gly  Gly  Thr  Tyr  Gly  Ala  Tyr  Asn  Gly  Thr  Ser  Met  Ala  Thr
               210                 215                      220

Pro  His  Val  Ala  Gly  Ala  Ala  Ala  Leu  Ile  Leu  Ser  Lys  His  Pro  Thr
225                           230                 235                      240

Trp  Thr  Asn  Ala  Gln  Val  Arg  Asp  Arg  Leu  Glu  Ser  Thr  Ala  Thr  Tyr
               245                 250                      255

Leu  Gly  Asn  Ser  Phe  Tyr  Tyr  Gly  Lys  Gly  Leu  Ile  Asn  Val  Gln  Ala
               260                 265                      270

Ala  Ala  Gln
275
```

( 2 ) INFORMATION FOR SEQ ID NO:9:

( i ) SEQUENCE CHARACTERISTICS:
        ( A ) LENGTH: 274 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Ala  Gln  Thr  Val  Pro  Tyr  Gly  Ile  Pro  Leu  Ile  Lys  Ala  Asp  Lys  Val
1              5                   10                       15

Gln  Ala  Gln  Gly  Phe  Lys  Gly  Ala  Asn  Val  Lys  Val  Ala  Val  Leu  Asp
               20                  25                       30

Thr  Gly  Ile  Gln  Ala  Ser  His  Pro  Asp  Leu  Asn  Val  Val  Gly  Gly  Ala
               35                  40                       45

Ser  Phe  Val  Ala  Gly  Glu  Ala  Tyr  Asn  Thr  Asp  Gly  Asn  Gly  His  Gly
     50                       55                  60

Thr  His  Val  Ala  Gly  Thr  Val  Ala  Ala  Leu  Asp  Asn  Thr  Thr  Gly  Val
65                       70                       75                       80

Leu  Gly  Val  Ala  Pro  Ser  Val  Ser  Leu  Tyr  Ala  Val  Lys  Val  Leu  Asn
               85                  90                       95

Ser  Ser  Gly  Ser  Gly  Ser  Tyr  Ser  Gly  Ile  Val  Ser  Gly  Ile  Glu  Trp
               100                 105                      110

Ala  Thr  Thr  Asn  Gly  Met  Asp  Val  Ile  Asn  Met  Ser  Leu  Gly  Gly  Ala
               115                 120                      125

Ser  Gly  Ser  Thr  Ala  Met  Lys  Gln  Ala  Val  Asp  Asn  Ala  Tyr  Ala  Arg
               130                 135                      140

Gly  Val  Val  Val  Val  Ala  Ala  Ala  Gly  Asn  Ser  Gly  Asn  Ser  Gly  Ser
```

```
                145                    150                   155                    160
Thr  Asn  Thr  Ile  Gly  Tyr  Pro  Ala  Lys  Tyr  Asp  Ser  Val  Ile  Ala  Val
                    165                      170                 175

Gly  Ala  Val  Asp  Ser  Asn  Ser  Asn  Arg  Ala  Ser  Phe  Ser  Ser  Val  Gly
               180                      185                 190

Ala  Glu  Leu  Glu  Val  Met  Ala  Pro  Gly  Ala  Gly  Val  Tyr  Ser  Thr  Tyr
          195                      200                 205

Pro  Thr  Asn  Thr  Tyr  Ala  Thr  Leu  Asn  Gly  Thr  Ser  Met  Ala  Ser  Pro
     210                      215                 220

His  Val  Ala  Gly  Ala  Ala  Ala  Leu  Ile  Leu  Ser  Lys  His  Pro  Asn  Leu
225                      230                 235                           240

Ser  Ala  Ser  Gln  Val  Arg  Asn  Arg  Leu  Ser  Ser  Thr  Ala  Thr  Tyr  Leu
               245                      250                 255

Gly  Ser  Ser  Phe  Tyr  Tyr  Gly  Lys  Gly  Leu  Ile  Asn  Val  Glu  Ala  Ala
               260                      265                 270

Ala  Gln
```

( 2 ) INFORMATION FOR SEQ ID NO:10:

( i ) SEQUENCE CHARACTERISTICS:
( A ) LENGTH: 269 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:10:

```
Ala  Gln  Ser  Val  Pro  Trp  Gly  Ile  Ser  Arg  Val  Gln  Ala  Pro  Ala  Ala
1                   5                        10                      15

His  Asn  Arg  Gly  Leu  Thr  Gly  Ser  Gly  Val  Lys  Val  Ala  Val  Leu  Asp
               20                       25                      30

Thr  Gly  Ile  Ser  Thr  His  Pro  Asp  Leu  Asn  Ile  Arg  Gly  Gly  Ala  Ser
          35                       40                      45

Phe  Val  Pro  Gly  Glu  Pro  Ser  Thr  Gln  Asp  Gly  Asn  Gly  His  Gly  Thr
     50                       55                      60

His  Val  Ala  Gly  Thr  Ile  Ala  Ala  Leu  Asn  Asn  Ser  Ile  Gly  Val  Leu
65                       70                       75                      80

Gly  Val  Ala  Pro  Ser  Ala  Glu  Leu  Tyr  Ala  Val  Lys  Val  Leu  Gly  Ala
               85                       90                      95

Ser  Gly  Ser  Gly  Ser  Val  Ser  Ser  Ile  Ala  Gln  Gly  Leu  Glu  Trp  Ala
               100                      105                     110

Gly  Asn  Asn  Gly  Met  His  Val  Ala  Asn  Leu  Ser  Leu  Gly  Ser  Pro  Ser
               115                      120                     125

Pro  Ser  Ala  Thr  Leu  Glu  Gln  Ala  Val  Asn  Ser  Ala  Thr  Ser  Arg  Gly
     130                      135                      140

Val  Leu  Val  Val  Ala  Ala  Ser  Gly  Asn  Ser  Gly  Ala  Gly  Ser  Ile  Ser
145                      150                      155                     160

Tyr  Pro  Ala  Arg  Tyr  Ala  Asn  Ala  Met  Ala  Val  Gly  Ala  Thr  Asp  Gln
               165                      170                     175

Asn  Asn  Asn  Arg  Ala  Ser  Phe  Ser  Gln  Tyr  Gly  Ala  Gly  Leu  Asp  Ile
               180                      185                     190

Val  Ala  Pro  Gly  Val  Asn  Val  Gln  Ser  Thr  Tyr  Pro  Gly  Ser  Thr  Tyr
          195                      200                      205

Ala  Ser  Leu  Asn  Gly  Thr  Ser  Met  Ala  Thr  Pro  His  Val  Ala  Gly  Ala
     210                      215                      220
```

|  Ala | Ala | Leu | Val | Lys | Gln | Lys | Asn | Pro | Ser | Trp | Ser | Asn | Val | Gln | Ile |
|---|---|---|---|---|---|---|---|---|---|---|---|---|---|---|---|
| 225 |  |  |  |  | 230 |  |  |  |  | 235 |  |  |  |  | 240 |

|  Arg | Asn | His | Leu | Lys | Asn | Thr | Ala | Thr | Ser | Leu | Gly | Ser | Thr | Asn | Leu |
|---|---|---|---|---|---|---|---|---|---|---|---|---|---|---|---|
|  |  |  |  | 245 |  |  |  | 250 |  |  |  |  | 255 |  |  |

|  Tyr | Gly | Ser | Gly | Leu | Val | Asn | Ala | Glu | Ala | Ala | Thr | Arg |
|---|---|---|---|---|---|---|---|---|---|---|---|---|
|  |  |  | 260 |  |  |  |  | 265 |  |  |  |  |

( 2 ) INFORMATION FOR SEQ ID NO:11:

( i ) SEQUENCE CHARACTERISTICS:
        ( A ) LENGTH: 1140 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
ATGAAGAAAC CGTTGGGGAA AATTGTCGCA AGCACCGCAC TACTCATTTC TGTTGCTTTT    60
AGTTCATCGA TCGCATCGGC TGCTGAAGAA GCAAAGAAA  AATATTTAAT TGGCTTTAAT   120
GAGCAGGAAG CTGTCAGTGA GTTTGTAGAA CAAGTAGAGG CAAATGACGA GGTCGCCATT   180
CTCTCTGAGG AAGAGGAAGT CGAAATTGAA TTGCTTCATG AATTTGAAAC GATTCCTGTT   240
TTATCCGTTG AGTTAAGCCC AGAAGATGTG GACGCGCTTG AACTCGATCC AGCGATTTCT   300
TATATTGAAG AGGATGCAGA AGTAACGACA ATGGCGCAAT CAGTGCCATG GGAATTAGC    360
CGTGTGCAAG CCCCAGCTGC CCATAACCGT GGATTGACAG GTTCTGGTGT AAAAGTTGCT   420
GTCCTCGATA CAGGTATTTC CACTCATCCA GACTTAAATA TTCGTGGTGG CGCTAGCTTT   480
GTACCAGGGG AACCATCCAC TCAAGATGGG AATGGGCATG GCACGCATGT GGCCGGGACG   540
ATTGCTGCTT TAAACAATTC GATTGGCGTT CTTGGCGTAG CGCCGAGCGC GGAACTATAC   600
GCTGTTAAAG TATTAGGGGC GAGCGGTTCA GGTTCGGTCA GCTCGATTGC CCAAGGATTG   660
GAATGGGCAG GGAACAATGG CATGCACGTT GCTAATTTGA GTTAGGAAG  CCCTTCGCCA   720
AGTGCCACAC TTGAGCAAGC TGTTAATAGC GCGACTTCTA GAGGCGTTCT TGTTGTAGCG   780
GCATCTGGGA ATTCAGGTGC AGGCTCAATC AGCTATCCGG CCCGTTATGC GAACGCAATG   840
GCAGTCGGAG CTACTGACCA AAACAACAAC CGCGCCAGCT TTTCACAGTA TGGCGCAGGG   900
CTTGACATTG TCGCACCAGG TGTAAACGTG CAGAGCACAT ACCCAGGTTC AACGTATGCC   960
AGCTTAAACG GTACATCGAT GGCTACTCCT CATGTTGCAG GTGCAGCAGC CCTTGTTAAA  1020
CAAAAGAACC CATCTTGGTC CAATGTACAA ATCCGCAATC ATCTAAAGAA TACGGCAACG  1080
AGCTTAGGAA GCACGAACTT GTATGGAAGC GGACTTGTCA ATGCAGAAGC GGCAACACGC  1140
```

( 2 ) INFORMATION FOR SEQ ID NO:12:

( i ) SEQUENCE CHARACTERISTICS:
        ( A ) LENGTH: 1140 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
ATGAAGAAAC CGTTGGGGAA AATTGTCGCA AGCACCGCAC TACTCATTTC TGTTGCTTTT    60
AGTTCATCGA TCGCATCGGC TGCTGAAGAA GCAAAAGAAA AATATTTAAT TGGCTTTAAT   120
GAGCAGGAAG CTGTCAGTGA GTTTGTAGAA CAAGTAGAGG CAAATGACGA GGTCGCCATT   180
CTCTCTGAGG AAGAGGAAGT CGAAATTGAA TTGCTTCATG AATTTGAAAC GATTCCTGTT   240
```

| | | | | | |
|---|---|---|---|---|---|
| TTATCCGTTG | AGTTAAGCCC | AGAAGATGTG | GACGCGCTTG | AACTCGATCC | AGCGATTTCT | 300 |
| TATATTGAAG | AGGATGCAGA | AGTAACGACA | ATGGCGCAAT | CAGTGCCATG | GGGAATTAGC | 360 |
| CGTGTGCAAG | CCCCAGCTGC | CCATAACCGT | GGATTGACAG | GTTCTGGTGT | AAAAGTTGCT | 420 |
| GTCCTCGATA | CAGGTATTTC | CACTCATCCA | GACTTAAATA | TTCGTGGTGG | CGCTAGCTTT | 480 |
| GTACCAGGGG | AACCATCCAC | TCAAGATGGG | AATGGGCATG | GCACGCATGT | GGCCGGGACG | 540 |
| ATTGCTGCTT | TAGACAACTC | GATTGGCGTT | CTTGGCGTAG | CGCCGAGCGC | GGAACTATAC | 600 |
| GCTGTTAAAG | TATTAGGGGC | GAGCGGTTCA | GGCGCCATCA | GCTCGATTGC | CCAAGGATTG | 660 |
| GAATGGGCAG | GGAACAATGG | CATGCACGTT | GCTAATTTGA | GTTAGGAAG | CCCTTCGCCA | 720 |
| AGTGCCACAC | TTGAGCAAGC | TGTTAATAGC | GCGACTTCTA | GAGGCGTTCT | TGTTGTAGCG | 780 |
| GCATCTGGGA | ATTCAGGTGC | AGGCTCAATC | AGCTATCCGG | CCCGTTATGC | GAACGCAATG | 840 |
| GCAGTCGGAG | CTACTGACCA | AACAACAAC | CGCGCCAGCT | TTCACAGTA | TGGCGCAGGG | 900 |
| CTTGACATTG | TCGCACCAGG | TGTAAACGTG | CAGAGCACAT | ACCCAGGTTC | AACGTATGCC | 960 |
| AGCTTAAACG | GTACATCGAT | GGCTACTCCT | CATGTTGCAG | GTGCAGCAGC | CCTTGTTAAA | 1020 |
| CAAAAGAACC | CATCTTGGTC | CAATGTACAA | ATCCGCAATC | ATCTAAAGAA | TACGGCAACG | 1080 |
| AGCTTAGGAA | GCACGAACTT | GTATGGAAGC | GGACTTGTCA | ATGCAGAAGC | GGCAACACGC | 1140 |

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

TATGCCAGCC ACAACGGTAC TTCGATGGCT         30

( 2 ) INFORMATION FOR SEQ ID NO:14:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CACAGTTGCG GCTCTAGATA ACTCAATCGG T         31

( 2 ) INFORMATION FOR SEQ ID NO:15:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GCTGACGGTT CCGGCGCTAT TAGTTGGATC ATT         33